United States Patent
Riley et al.

(10) Patent No.: US 7,754,482 B2
(45) Date of Patent: Jul. 13, 2010

(54) ARTIFICIAL ANTIGEN PRESENTING CELLS AND USES THEREFOR

(75) Inventors: James L. Riley, Downingtown, PA (US); Carl H. June, Merion Station, PA (US); Robert H. Vonderheide, Merion Station, PA (US); Nicole Aqui, Philadelphia, PA (US); Megan M. Suhoski, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1129 days.

(21) Appl. No.: 11/137,807

(22) Filed: May 25, 2005

(65) Prior Publication Data

US 2006/0034810 A1    Feb. 16, 2006

Related U.S. Application Data

(60) Provisional application No. 60/575,712, filed on May 27, 2004.

(51) Int. Cl.
C12N 5/00 (2006.01)
(52) U.S. Cl. .................. 435/375; 435/373; 435/377; 424/93.2
(58) Field of Classification Search .................. None
See application file for complete search history.

(56) References Cited

U.S. PATENT DOCUMENTS

| | | | |
|---|---|---|---|
| 5,166,320 A | 11/1992 | Wu et al. |
| 5,190,878 A | 3/1993 | Wilhelm |
| 5,529,921 A | 6/1996 | Peterson et al. |
| 5,827,642 A | 10/1998 | Riddell et al. |
| 5,858,358 A | 1/1999 | June et al. |
| 5,888,807 A | 3/1999 | Palsson et al. |
| 5,962,320 A | 10/1999 | Robinson |
| 5,985,653 A | 11/1999 | Armstrong et al. |
| 6,001,365 A | 12/1999 | Peterson et al. |
| 6,096,532 A | 8/2000 | Armstrong et al. |
| 6,352,694 B1 | 3/2002 | June et al. |
| 6,355,479 B1 | 3/2002 | Webb et al. |
| 6,464,973 B1 | 10/2002 | Levitsky et al. |
| 6,534,055 B1 | 3/2003 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,890,753 B2 | 5/2005 | Flyer et al. |
| 6,905,681 B1 | 6/2005 | June et al. |
| 6,905,874 B2 | 6/2005 | Berenson et al. |
| 7,175,843 B2 | 2/2007 | June et al. |
| 2003/0147869 A1 | 8/2003 | Riley et al. |
| 2003/0224520 A1 | 12/2003 | June et al. |
| 2004/0101519 A1 | 5/2004 | June et al. |
| 2004/0110290 A1 | 6/2004 | June et al. |
| 2004/0191235 A1 | 9/2004 | Groux et al. |
| 2004/0241162 A1 | 12/2004 | Berenson et al. |
| 2005/0003484 A1 | 1/2005 | Hirano et al. |
| 2006/0121005 A1 | 6/2006 | Berenson et al. |

FOREIGN PATENT DOCUMENTS

| | | |
|---|---|---|
| WO | 94/17810 A1 | 8/1994 |
| WO | 94/23744 A1 | 10/1994 |
| WO | WO95/00642 | 1/1995 |
| WO | WO95/03408 | 2/1995 |
| WO | WO95/33823 | 12/1995 |
| WO | WO99/36093 | 7/1999 |
| WO | WO00/25813 | 5/2000 |
| WO | WO03/006632 | 1/2003 |
| WO | 03/057171 A2 | 7/2003 |
| WO | WO 03/057171 | 7/2003 |
| WO | WO03/065977 | 8/2003 |

OTHER PUBLICATIONS

Sakaguchi, Nat Immunol 2005;6:345-52.*
Viguier et al. J Immunol 2004;173:1444-53.*
Salomon, Immunity 2000;12:431-40.*
Curiel, Nat Med 2004;10:942-9. Epub Aug. 22, 2004.*
Hoffmann et al. Blood 2004;104:895-903.*
Dietz et al. Cytother 2001;3:97-105.*
Alexander-Miller, M. A. et al., "Selective Expansion of High- or Low-Avidity Cytotoxic T Lymphocytes and efficacy for Adoptive Immunotherapy," *Proc. Natl. Acad. Sci. USA*, vol. 93, pp. 4102-4107, 1996.
Assoian, R. K. et al., "Expression and Secretion of Type β Transforming Growth Factor by Activated Human Macrophages," *Pro. Natl. Acad. Sci. USA*, vol. 84, pp. 6020-6024, 1987.
Britten, C. M. et al., "The Use of HLA-A*0201-Transferred K562 as Standard Antigen-Presenting Cells for CD8(+) T Lymphocytes in IFN-Gamma ELISPOT Assays," *J. Immunol. Methods*, vol. 259, pp. 95-110, 2002.
Brodie, S. J. et al., "In Vivo and Function of Transferred HIV-1-Specific Cytotoxic T Cells," *Nature Med.*, vol. 5, pp. 34-41, 1999.
Carroll, R. G. et al., "Differential Regulation of HIV-1 Fusion Cofactor Expression by CD28 Costimulation of CD4+ T Cells," *Science*, vol. 276, pp. 273-276, 1997.
Coyle, A. J. et al., "The CD28-Related Molecule ICOS is Required for Effective T Cell-Dependent Immune Responses," *Immunity*, vol. 13, pp. 95-105, 2000.

(Continued)

*Primary Examiner*—Q. Janice Li
(74) *Attorney, Agent, or Firm*—Drinker Biddle & Reath LLP

(57) ABSTRACT

The invention relates to novel artificial antigen presenting cells (aAPCs). The aAPC comprises at least one stimulatory ligand and at least one co-stimulatory ligand where the ligands each specifically bind with a cognate molecule on a T cell of interest, thereby mediating expansion of the T cell. The aAPC of the invention can further comprise additional molecules useful for expanding a T cell of interest. The aAPC of the invention can be used as an "off the shelf" APC that can be readily designed to expand a T cell of interest. Also, the aAPC of the invention can be used identify the stimulatory, co-stimulatory, and any other factors that mediate growth and expansion of a T cell of interest. Thus, the present invention provides powerful tools for development of novel therapeutics where activation and expansion of a T cell can provide a benefit.

2 Claims, 22 Drawing Sheets

OTHER PUBLICATIONS

Deeks, S. G. et al., "A Phase II Randomized Study of HIV-Specific T-Cell Gene Therapy in Subjects With Undetectable Plasma Viremia on Combination Antiretroviral Therapy," *Mol. Ther.*, vol. 5, pp. 788-797, 2002.

Deeths, M. J. et al., "CD8+ T Cells Become Nonresponsive (Anergic) Following Activation in the Presence of Costimulation," *Journal of Immunology*, vol. 163, pp. 102-110, 1999.

Dull, T. et al., "A Third-Generation Lentivirus Vector With a Conditional Packaging System," *Journal of Virology*, vol. 72, pp. 8463-8471, 1998.

Flamand, L. et al., "Activation of CD8+ T Lymphocytes Through the T Cell Receptor Turns on CD4 Gene Expression: Implications for HIV Pathogenesis," *Proc. Natl. Acad. Sci. USA.*, vol. 95, pp. 3111-3116, 1998.

Gonzalo, J. A. et al., "ICOS is Critical for T Helper Cell-Mediated Lung Mucosal Inflammatory Responses," *Nature Immunol.*, vol. 2, pp. 597-604, 2001.

Gupta, S. K. et al., "Modulation of CXCR4 Expression and SDF-1α Functional Activity During Differentiation of Human Monocytes and Macrophages," *J. Leukoc. Biol.*, vol. 66, pp. 135-143, 1999.

Heslop, H. E. et al., "Long-Term Restoration of Immunity Against Epstein-Barr Virus Infection by Adoptive Transfer of Gene-Modified Virus-Specific T Lymphocytes," *Nature Med.*, vol. 2, pp. 551-555, 1996.

Hutloff, A. et al., "ICOS is an Inducible T-Cell Costimulator Structurally and Functionally Related to CD28," *Nature*, vol. 397, pp. 263-266, 1999.

Imlach, S. et al., "Activated Peripheral CD8 Lymphocytes Express CD4 in Vivo and Are Targets for Infection by Human Immunodeficiency Virus Type 1," *Journal of Virology*, vol. 75, pp. 11555-11564, 2001.

Kahl, C. A. et al., "Human Immunodeficiency Virus Type 1-Derived Lentivirus Vectors Pseudotyped with Envelope Glycoproteins Derived from Ross River Virus and Semliki Forest Virus," *Journal of Virology*, vol. 78, pp. 1421-1430, 2004.

Koenig, S. et al, "Transfer of HIV-1-Specific Cytotoxic T Lymphocytes to an AIDS Patient Leads to Selection for Mutant HIV Variants and Subsequent Disease Progression," *Nature Med.*, vol. 1, pp. 330-336, 1995.

Lee, A. W. et al., "A Clinical Grade Cocktail of Cytokines and $PGE_2$ Results in Uniform Maturation of Human Monocyte-Derived Dendritic Cells: Implications for Immunotherapy," *Vaccine*, vol. 20, pp. A8-A22, 2002.

Levine, B. L. et al., "Antiviral Effect and Ex Vivo CD4+ Cell Proliferation in HIV-Positive Patients as a Result of CD28 Costimulation," *Science*, vol. 272, p. 1939-1943, 1996.

Levine, B. L. et al., "Effects of CD28 Costimulation on Long-Term Proliferation of CD4+ T Cells in the Absence of Exogenous Feeder Cells," *J. Immunol.* vol. 159, pp. 5921-5930, 1997.

Levine, B. L. et al., "Adoptive Transfer of Costimulated CD4+ T Cells Induces Expansion of Peripheral T Cells and Decreased CCR5 Expression in HIV Infection," *Nature Med.*, vol. 8, pp. 47-53, 2002.

Lieberman, J. et al., "Safety of Autologous, Ex Vivo-Expanded Human Immunodeficiency Virus (HIV)-Specific Cytotoxic T-Lymphocyte Infusion in HIV-Infected Patients," *Blood*, vol. 90, pp. 2196-2206, 1997.

Lozzio, C. B. et al., "Human Chronic Myelogenous Leukemia Cell-Line With Positive Philadelphia Chromosome," *Blood*, vol. 45, pp. 321-334, 1975.

Maus, M. V. et al., "Ex Vivo Expansion of Polyclonal and Antigen-Specific Cytotoxic T Lymphocytes by Artificial APCs Expressing Ligands for the T-Cell Receptor, CD28 and 4-1BB," *Nature Biotechnology.*, vol. 20, pp. 143-148, 2002.

Maus, M. V. et al., "HLA Tetramer-Based Artificial Antigen-Presenting Cells for Stimulation of CD4+ T Cells," *Clin. Immunol.*, vol. 106, pp. 16-22, 2003.

Mitsuyasu, R. T. et al., "Prolonged Survival and Tissue Trafficking Following Adoptive Transfer of CD4ζ Gene-Modified Autologous CD4+ and CD8+ T Cells in Human Immunodeficiency Virus-Infected Subjects," *Blood*, vol. 96, pp. 785-793, 2000.

O'Doherty, U. et al., "Human Immunodeficiency Virus Type 1 Spinoculation Enhances Infection Through Virus Binding," *Journal of Virology*, vol. 74, pp. 10074-10080, 2000.

Oh, S. et al., "Selective induction of High Avidity CTL by Altering the Balance of Signals from APC," *Journal of Immunology*, vol. 170, pp. 2523-2530, 2003.

Parry, R. V. et al., "CD28 and Inducible Costimulatory Protein Sre Homology 2 Binding Domains Show Distinct Regulation of Phosphatidylinositol 2-Kinase, Bcl-$x_L$, ad IL-2 Expression in Primary Human CD4 T Lymphocytes," *Journal of Immunology*, vol. 171, pp. 166-174, 2003.

Ranga, U. et al., "Enhanced T Cell Engraftment After Retroviral Delivery of an Antiviral Gene in HIV-Infected Individuals," *Proc. Natl. Acad. Sci. U.S.A.*, vol. 95, pp. 1201-1206, 1998.

Riddell, S. R. et al., "Restoration of Viral Immunity in Immunodeficient Humans by the Adoptive Transfer of T Cell Clones," *Science*, vol. 257, pp. 238-241, 1992.

Riddell, S. R. et al., "T-Cell Mediated Rejection of Gene-Modified HIV-Specific Cytotoxic T Lymphocytes in HIV-Infected Patients," *Nature Med.*, vol. 2, pp. 216-223, 1996.

Riddell, S. R. et al., "Immunotherapy of Human Viral and Malignant Diseases With Genetically Modified T-Cell Clones," *Cancer Journal*, vol. 6, pp. S250-S258, 2000.

Riley, J. L. et al., "Intrinsic Resistance to T Cell Infection With HIV Type 1 Induced by CD28 Costimulation," *J. Immunol.*, vol. 158, pp. 5545-5553, 1997.

Rooney, C. M. et al., "Use of Gene-Modified Virus-Specific T Lymphocytes to Control Epstein-Barr-Virus-Related Lymphoproliferation," *Lancet*, vol. 345, pp. 9-13, 1995.

Rosenberg, S. A. et al., "Gene Transfer Into Humans—Immunotherapy of Patients With Advanced Melanoma, Using Tumor-Infiltrating Lymphocytes Modified by Retroviral Gene Transduction," *N. Engl. J. Med.*, vol. 323, pp. 570-578, 1990.

Schlienger, K. et al., Efficient Priming of Protein Antigen-Specific Human CD4+ T Cells by Monocyte-Derived Dendritic Cells, *Blood*, vol. 9, pp. 3490-3498, 2000.

Scholler, N. et al., "CD83 Is a Sialic Acid-Binding Ig-Like Lectin (Siglec) Adhesion Receptor That Binds Monocytes and a Subset of Activated CD8+ Cells," *Journal of Immunology*, vol. 166, pp. 3865-3872, 2001.

Scholler, N. et al., "Cutting Edge: CD83 Regulates the Development of Cellular Immunity" *Journal of Immunology*, vol. 168, 2599-2602, 2002.

Schwartz, J. C. et al., "Structural Basis for Costimulation by the Human CTLA-4/B7-2 Complex," *Nature*, vol. 410, pp. 604-608, 2001.

Schwartz, J. et al., "Structural Mechanisms of Costimulation," *Nature Immunol.*, vol. 3, pp. 427-434. 2002.

Shedlock, D. J. et al, "Requiremeut for CD4 T Cell Help in Generating Functional CD8 T Cell Memory," *Science*, vol. 300, pp. 337-339, 2003.

Shuford, W. W. et al., "4-1BB Costimulatory Signals Preferentially Induce CD8+ Cell Proliferation and Lead to the Amplification in vivo of Cytotoxic T Cell Responses," *J. Exp. Med.*, vol. 186, pp. 47-55, 1997.

Sun, J. C. et al, "Defective CD8 T Cell Memory Following Acute Infection Without CD4 T Cell Help," *Science*, vol. 300, pp. 339-342, 2003.

Thomas, A. K. et al., "A Cell-Based Artificial Antigen-Presenting Cell Coated With Anti-CD3 and CD28 Antibodies Enables Rapid Expansion and Long-Term Growth of CD4 T Lymphocytes," *Clin. Immunol.*, vol. 105, pp. 259-272, 2002.

Topp, M. S. et al., "Restoration of CD28 Expression in CD28-CD8+ Memory Effector T Cells Reconstitutcs Antigen-indueed II-2 Production," *J. Exp. Med.*, vol. 198, pp. 947-955, 2003.

Vonderheide, R. H. et al., "The Telomerase Catalytic Subunit is a Widely Expressed Tumor-Associated Antigen Recognized by Cytotoxic T Lymphocytes," *Immunity*, vol. 10, pp. 673-679, 1999.

Vonderheide, R. H. et al., "A Translational Bridge to Cancer Immunotherapy: Exploiting Costimulation and Target Antigens for Active and Passive T Cell Immunotherapy," *Immun. Research*, vol. 27, pp. 341-356, 2003.

Vonderheide, R. H. et al., "Vaccination of Cancer Patients Against Telomerase Induces Functional Antitumor CD8+ T Lymphocytes," *Clin. Cancer Res.*, vol. 10, pp. 828-839, 2004.
Walker, R. E. et al., "Long-Term In Vivo Survival of Receptor-Modified Syngeneic T Cells in Patients With Human Immunodeficiency Virus Infection," *Blood*, vol. 96, pp. 467-474, 2000.
Walter, E. A. et al., "Reconstitution of Cellular Immunity Against Cytomegalovirus in Recipients of Allogeneic Bone Marrow by Transfer of T-Cell Clones From the Donor," *N. Engl. J. Med.*, vol. 333, 1038-1044, 1995.
Warrington, J. et al., "CD28 Loss in Senescent CD4+ T Cells: Reversal by Interleukin-12 Stimulation," *Blood*, vol. 101, pp. 3543-3549, 2003.
Wells, A. D. et al., "Following the Fate of Individual T Cells Throughout Activation and Clonal Expansion," *J. Clin. Invest.*, vol. 100, pp. 3173-3183, 1997.
Weng, N. et al., "Regulation of Telomerase RNA Template Expression in Human T Lymphocyte Development and Activation," *J. Immunol.*, vol. 158, pp. 3215-3220, 1997.
Yee, C. et al., "Adoptive T Cell Therapy Using Antigen-Specific CD8+ T Cell Clones for the Treatment of Patients With Metastatic Melanoma: In Vivo Persistence, Migration, and Antitumor Effect of Transferred T Cells," *Proc. Natl. Acad. Sci. USA*, vol. 99, pp. 16168-16173, 2002.
Zajac, A. J. et al., "Viral Immune Evasion Due to Persistence of Activated T Cells Without Effector function," *J. Exp. Med.*, vol. 188, pp. 2205-2213, 1998.
Zhang, X. et al., "Structural and Functional Analysis of the Costimulatory Receptor Programmed Death-1," *Immunity*, vol. 20, pp. 337-347, 2004.
Zufferey, R. et al., "Self-Inactivating Lentivirus Vector for Safe and Efficient In Vivo Gene Delivery," *Journal of Virology*, vol. 72, pp. 9873-9880, 1998.
Abendroth, A. et al., "Infection With an H2 Recombinant Herpes Simplex Virus Vector Results in Expression of MHC Class 1 Antigens on the Surfaces of Human Neuroblastoma Cells In Vitro and Mouse Sensory Neurons In Vivo," *Journal of General Virology*, (2000), vol. 1, pp. 2375-2383.
Esslinger, C. et al., "Efficient Transduction of Dendritic Cells and Induction of a T-Cell Response by Third-Generation Lentivectors," *Human Gene Therapy* (2002), vol. 13, pp. 1091-1100.
Grosenbach, D.W. et al., "A Recombinant Vector Expressing Transgenes for Four T-Cell Costimulatory Molecules (OX40L,. B7-1, ICAM-1, LFA-3) T-Cell Activation, Protection From Apoptosis, and Enhanced Cytokine Production," *Cellular Immunology*, (2003), vol. 222, pp. 45-57.
Niethammer, A.G. et al., "An Oral DNA Vaccine Against Human Carcinoembryonic Antigen (CEA) Prevents Growth and Dissemination of Lewis Lung Carcinoma in CEA Transgenic Mice," *Vaccine*, (2002), vol. 20, pp. 421-429.
Qiao et al., "Construction and Characterization of a Recombinant Adenoviral Vector Expressing Human Interleukin-12," *Cancer Gene Therapy*, (1999), vol. 6, pp. 373-379.
Stripcke et al., 2000 Blood 96: 1317-1326.
Afanasyeva et al., 2001 Circulation 104(25):3145-3151.
Almand, et al., 2000, Clin Cancer Res, 6:1755-1766.
Altman et al., 1996, Science 274(5284):94-96.
ATCC Cell Lines and Hybridomas 1994 8th Edition, p. 129.
Bamford, et al., 1998, J Immuol 160:4418-26.
Brierer et al., 1991, Adv Cancer Research 56:49-76.
Bretscher 1992 Immunol Today 13:74-76.
Byun et al., 1994 J Immunol 153:4862-71.
Chapoval et al., 2001, Nat Immunol 2(3):269-274.
Claret et al., 1997 J Clin Invest 100(4):855-66.
Curtsinger et al., 1998, J Immunol 160(7):3236-3243.
Dahl et al., 2000 J Exp Med 191(12):2031-8.
DeBenedette et al., 1997, J. Immunol 158:551-559.
Deeths et al., 1997 Eur J Immunol 27:598-608.
Dong et al., 1999, Nat Med 5(12):1365-1369.
Dudley et al., 2001, J Immunother 24(4):363-373.
Dunbar et al., 1998, Curr Biol 8(7):413-416.
Fanger et al., 1996, J Immunol 157(2):541-548.
Fraser, et al., 1991 Science 251(4991):313-16.
Freeman at al., 2000, J Exp Med 192(7)1027-1034.
Gett et al., 1998 Proc Nati Acad Sci USA 95(16):9488-93.
Gett et al., 2000, Nature Immunology 1(3):239-244.
Gillis et al., 1977, Nature 268:154-156.
Gimmi et al., 1991 Proc Natl Acad Sci USA 88:6575-6579.
Goodwin, et al., 1993, Eur J. Immunol 23(10):2631:2641.
Groux et al., 1993, Eur J Immunol 23(7):1623-1629.
Guinn et al., 1999, J Immunol 162(8):5003-5010.
Hansen et al., 1980 Immunogenetics 10:247-260.
Harding et al., 1992, Nature 356 (6370):607-609.
Hurtado et al., 1995, J Immunol 155(7):3360-3367.
Hurtado et al., 1997, J Immunol 158(6):2600-2609.
Iezzi et al., 1998, Immunity 8(1):89-95.
Jelley-Gibbs et al., 2000 J. Immunol. 165(9):5017-5026.
Jenkins et al. 1993, Curr Opin Immunol 5(3):361-367.
June et al., 1987 Mol Cell Biol. 7(12):4472-4481.
June et al., 1994, Immunol Today 15(7):321-331.
Kabelitz, et al., 1992 Int Immunol 4(12):1381-1388.
Kato et al., 1998, J Clin invest 101(5):1133-1141.
Kawabe, et al., 1991, Nature, 349(6306):245-248.
Krummel 1996, J Exp Med 183(6)2533-2540.
Ku et al., 2000 Science 288(5466):675-678.
Kung at al., 1979 Science 206(4416):347-349.
Kurys et al., 2000, J Biol Chem 275(2):30653-30659.
Latchman et al., 2001, Nat Immunol 2(3):261-268.
Latouche et al., 2000 Nat Biotechnol 18.405-409.
Laux et al., 2000, Clinical Immunology 96(3):187-197.
Lenschow et al.,1992, Science 257:789-792.
Levine et al., 1995, Inter Immunol 7(6):891-904.
Li, et al. 2001, Nat Med 7(1):114-118.
Liebowitz et al., 1998 Curr Opin Oncol 10(6):533-541.
Lindsten et al., 1989, Science, 244 (4902):339-343.
Linsley et al., 1993, Annu Rev Immunol 11:191-212.
Lord et al., 1998, J Immunol 161(9):4627-4633.
Malefyt et al. 1993, J Immunol 150(11):4754-4765.
Marks-Konczalik et al., 2000, Proc Natl Acad Sci USA 97(21):11445-11450.
Melero et al., 1997, Nat Med, 3(6):682-685.
Melero et al., 1998, Eur J Immunol 28(3):1116-1121.
Melief et al., 1995, Immunol Rev 145:167-177.
Muller et al., 1999, Immunology 97(2):280-286.
Mussy et al., 1999, Blood 93(10):3531-3539.
Pollak et al, 1993, J Immunol 150(3):771-781.
Prakken et al., 2000, Nat Med 6(12):1406-1410.
Rabinovitch, 1983, Proc Natl Acad Sci USA 80(10):2951-2955.
Ranheim et al., 1993, J Exp Med 177(4):925-935.
Refaeli et al., 1998, Immunity 8(5):615-623.
Riddell et al., 1992, Hum Gene Ther 3(3):319-338.
Riddell et al., 1990, J Immunol Methods 128(2):189-201.
Riddell et al., 1995, Annu Rev Immunol 13:545-586.
Riley et al., 2001, J Immunol, 166(8):4943-4948.
Rooney et al., 1998, Blood 92(5):1549-1555.
Rosenberg et al. 1988, N Engl J Med 319(25):1676-1680.
Sagerstrom et al., 1993, Proc Natl Acad Sci USA 90(19):8987-8991.
San Jose et al., 1998, Eur J Immunol 28(1):12-21.
Saouilli et al., 1998, J Exp Med 187(11)1849-1862.
Schwartz, 1990 Science, 248 (4961):1349-1356.
Schwartz, 1992, Cell 71(7)1065-1068.
Shibuya et al., 1999, Arch Otolaryngol Head Neck Surg. 125(11):1229-1234.
Smith et al., 1979 Ann NY Acad Sci 332:423-432.
Springer et al., 1987, Ann Rev Immunol 5:223-252.
Tagaya et al., 1997, Proc Natl Acad Sci USA 94(26):14444-14449.
Takahashi et al., 1999, J Immunol 162(9):5037-5040.
Tan et al., 2000, J Immunol 164(5):2320-2325.
Tan, 2001, J Clin Invest 108(10):1411-1415.
Tseng et al., 2001, J Exp Med 193(7):839-845.
Turka et al., 1992, Proc Natl Aced Sci USA 89(22):11102-11105.
Van de Winkel et al., 1993, Immunol Today 14(5):215-221.
Van Parijs et al., 1999, Immunity 11(3)281-288.
Vieweg et al., 2004 Expert Opin Biot Ther 4(11):1791-1801.
Voltz et al., 1999, N Engl J Med 340(23):1788-1795.

Wakasugi et al., 1983 Proc Natl Acad Sci USA 80(19):6028-6031.
Wang et al., 2000, J Immunol 164(3):1216-1222.
Webb et al., 1990, Cell 63(6):1249-1256.
Wells et al., 2000, J Immunol 165(5):2432-2443.
Yee et al., 1999, J Immunol 162(4):2227-2234.
Yee et al., 2000, J Exp Med 192(11):1637-1644.

Yee et al., 2001, Curr Opin Immunol 13(2):141-146.
Yotnda et al., 1998, J Clin Invest 101(10)2290-2296.
Zamai et al, 1994, Eur J Histochem 38(1):53-60.
Zhu et al., 2001 J Immunol, 167(5):2671-2676.

* cited by examiner

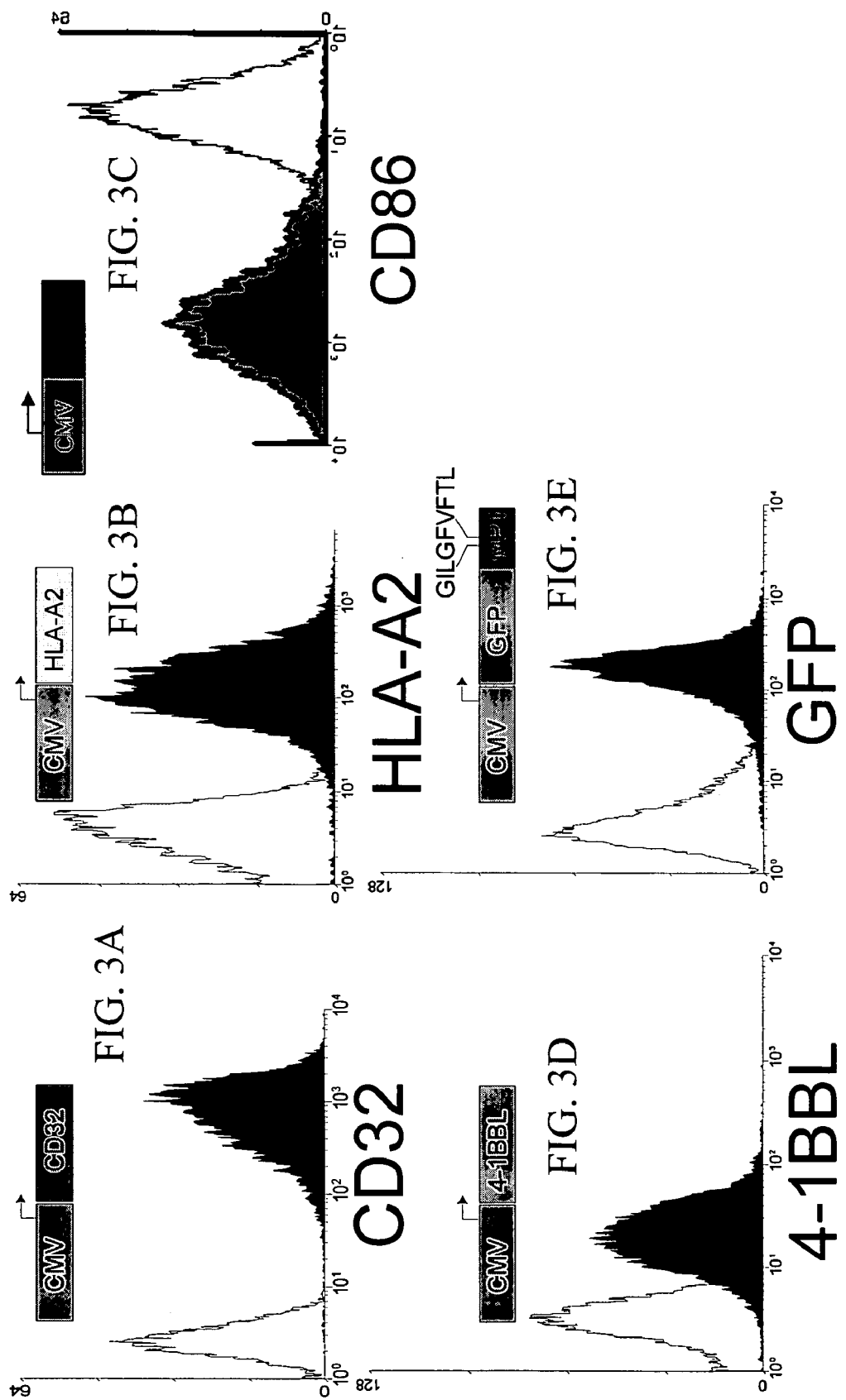

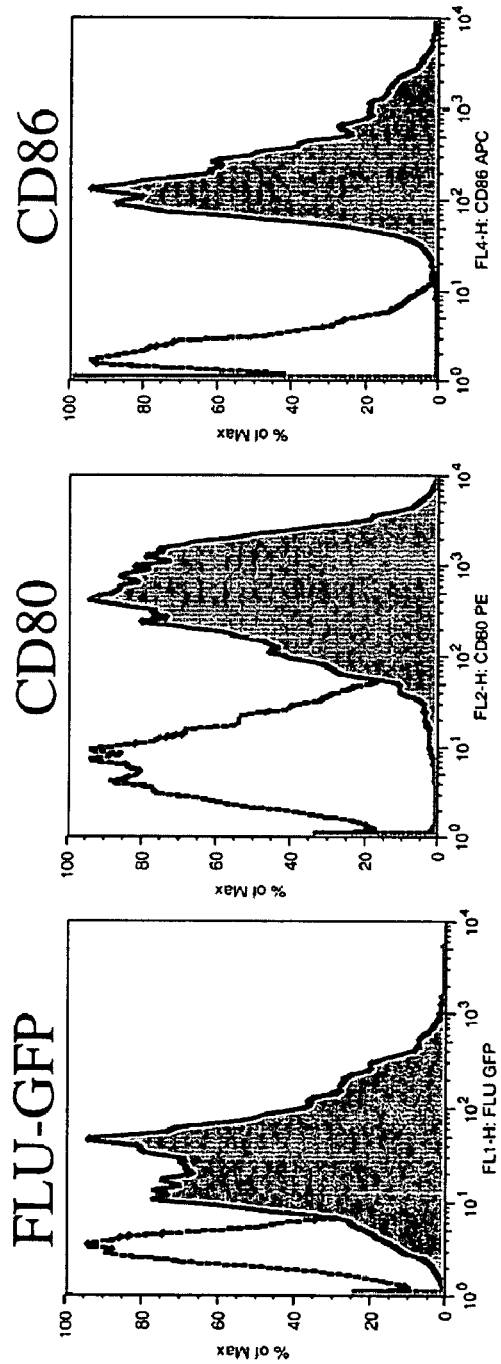
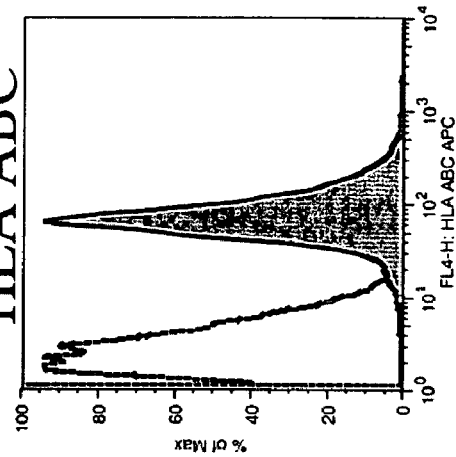
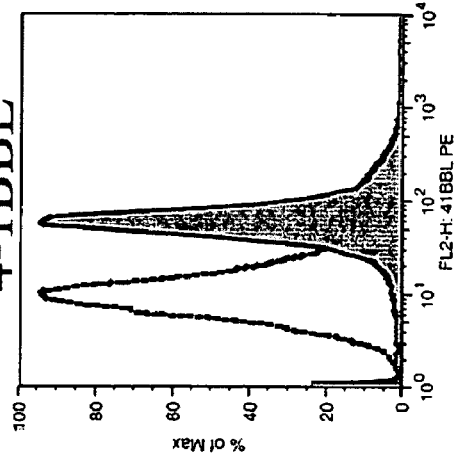
FIG. 8A 4-1BBL
FIG. 8B HLA ABC
FIG. 8C CD86
FIG. 8D
FIG. 8E
*ALSO EXPRESSES CD32, CD83, CD40L
8-THREAT
K562CC PARENT

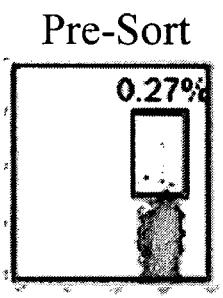 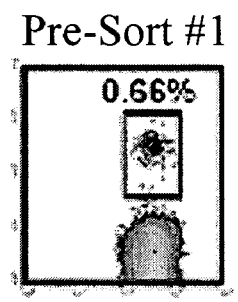 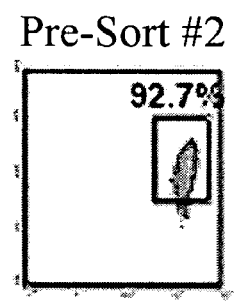
Pre-Sort　　　　　　Pre-Sort #1　　　　　Pre-Sort #2
CD8　　　　　　　　CD8　　　　　　　　CD8
FIG. 10A　　　　　FIG. 10B　　　　　FIG. 10C
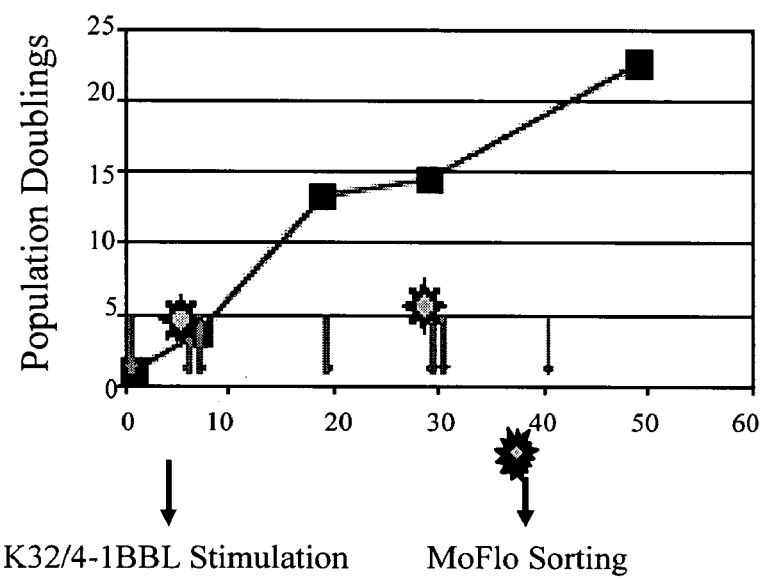
K32/4-1BBL Stimulation　　　MoFlo Sorting
FIG. 10D
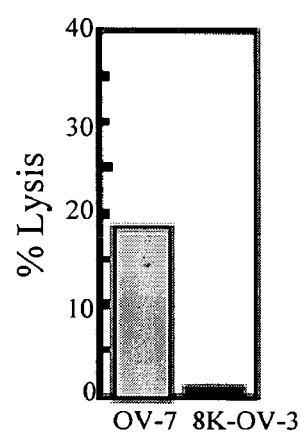
FIG. 10E FIG. 12A
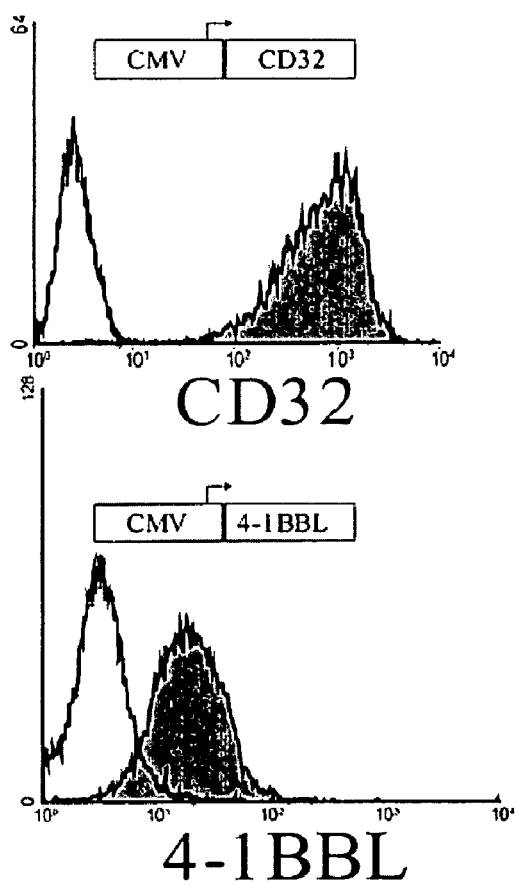
CD32
4-1BBL
FIG. 12C
FIG. 12B
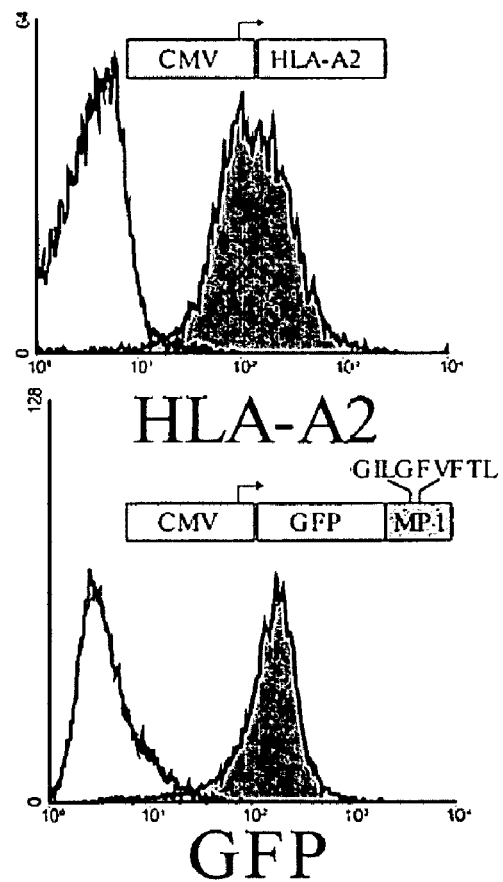
HLA-A2
GFP
FIG. 12D

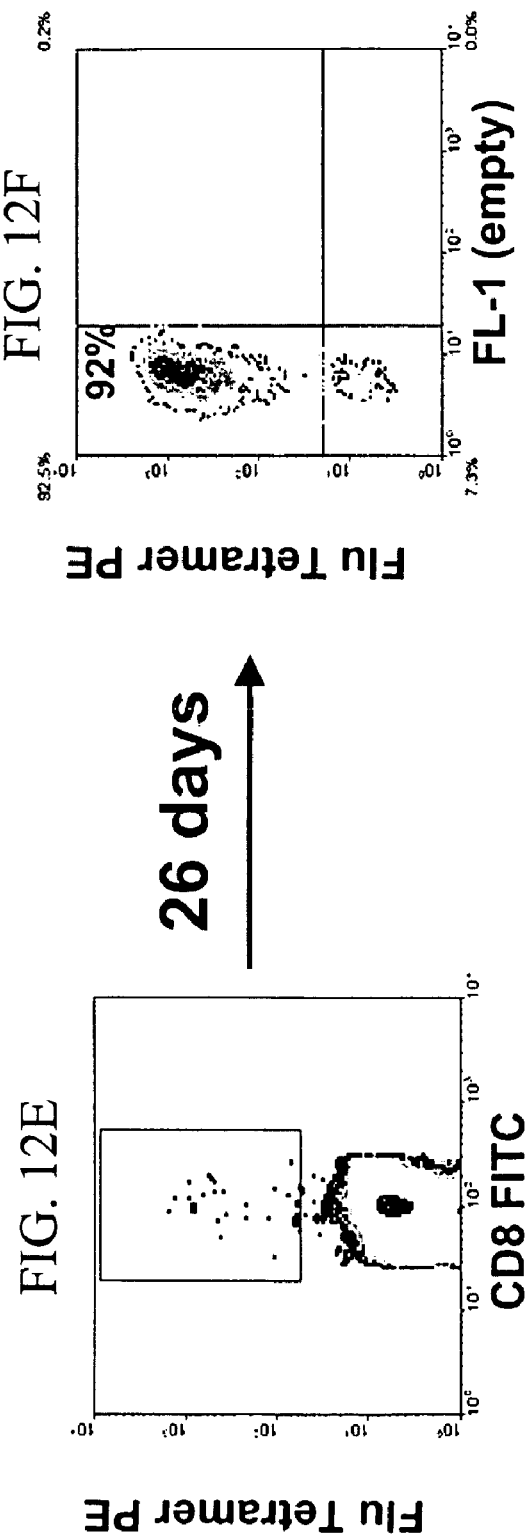

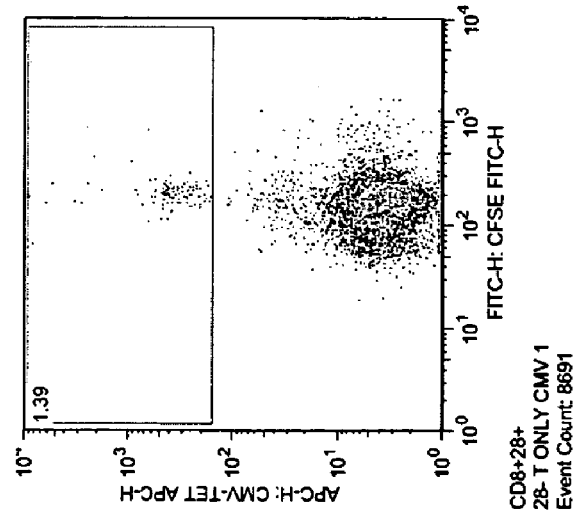
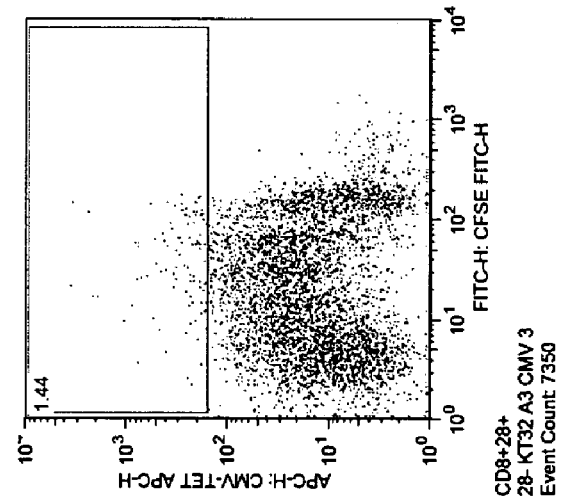
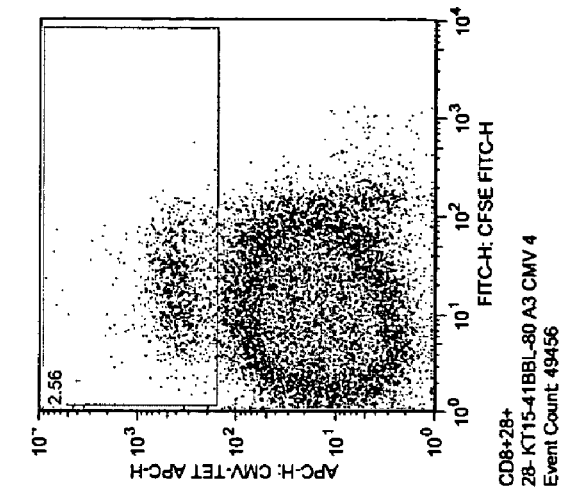
FIG. 21C
FIG. 21B
FIG. 21A

ARTIFICIAL ANTIGEN PRESENTING CELLS AND USES THEREFOR

CROSS-REFERENCE TO RELATED APPLICATIONS

This application is entitled to priority pursuant to 35 U.S.C. §119(e) to U.S. Provisional Patent Application No. 60/575,712, which was filed on May 27, 2004, which is incorporated by reference in its entirety herein.

STATEMENT REGARDING FEDERALLY SUPPORTED RESEARCH OR DEVELOPMENT

This research was supported in part by U.S. Government funds (National Institutes of Health Grants R21 AI060477, R01 CA105216 and R01 AI 057838, and the U.S. Government may therefore have certain rights in the invention.

BACKGROUND OF THE INVENTION

Adoptive transfer is a term coined by Medawar (1954, Proc. Royal Soc. 143:58-80) to study allograft rejection. The term adoptive immunotherapy denotes the transfer of immunocompetent cells for the treatment of cancer or infectious diseases (June, C. H., ed., 2001, In: Cancer Chemotherapy and Biotherapy: Principles and Practice, Lippincott Williams & Wilkins, Baltimore; Vonderheide et al., 2003, Immun. Research 27:1-15). Adoptive therapy can be considered as a strategy aimed at replacing, repairing, or enhancing the biological function of a damaged tissue or system by means of autologous or allogeneic cells. The first successful infusion of ex vivo expanded, HIV infected, polyclonal CD4 T cells that enabled a high degree of engraftment upon infusion, was performed using magnetic beads coated with anti-CD3 and anti-CD28 beads (CD3/28 coated beads) to ex vivo expand the HIV infected individuals T cells. Eight patients were administered 51 infusions of costimulated CD4 cells under this protocol with minimal adverse advents (Levine et al., 2002, Nature Med. 8:47-53).

HIV infection induces a pronounced expansion of HIV-specific CD8 T cells. These CD8 T cells release soluble factors (Walker et al., 1986, Science 234:1563-1566; Zhang et al., 2002, Science 298:995-1000; Cocchi et al., 1995, Science 270:1811-1815) that limit HIV replication as well as directly lyse HIV infected cells (Walker et al., 1987, Nature 328:345-348; Koup et al., 1994, J. Virol. 68:4650-4655). Depletion of CD8 T cells prior to SIV challenge leads to unchecked viral replication and a rapid death, indicating that CD8 T cell activity is necessary to make HIV a chronic disease (Schmitz et al. 1999, Science 283:857-860; Jin et al., 1999, J. Exp. Med. 189:991-998). Yet, CD8 T cells ultimately fail to control HIV infection. HIV-specific T cells have been shown to have highly reduced perforin expression (Zhang et al., 2003, Blood 101:226-235; Appay, et al., 2000, J. Exp. Med. 192:63-75), down-regulation of two key signaling receptors, CD3ζ and CD28 (Trimble et al., 2000, Blood 96:1021-1029), a skewed maturation pattern (Appay et al., 2002, Nature Med. 8, 379-385) and a high sensitivity to Fas induced apoptosis (Mueller et al., 2001, Immunity, 15:871-882). Thus, it is believed that optimal activation of HIV specific CD8 T cells will restore effector functions.

Anti-CD3 and anti-CD28 (CD3/28) coated beads were the first generation of artificial APCs (aAPC) that permitted expansion of HIV-infected CD4 T cells (Levine et al., 1996, Science 272:1939-1943). In addition to delivering the signals needed for T cell activation and growth, CD3/28 bead stimulation renders T cells resistant to R5 infection by down-regulating CCR5 and up-regulating the expression of its ligands, the β-chemokines RANTES, Macrophage Inflammatory Protein-1 alpha (MIP-1α) and MIP-1β (Riley et al., 1997, J. Immunol. 158:5545-5553 Carroll et al., 1997, Science 276:273-276). Several phase I and II trials have demonstrated that infusion of autologous CD4 T cells expanded using CD3/28 coated beads into R5-infected individuals is both safe and feasible (Carroll et al., 1997, Science 276:273-276; Levine et al., 2002, Nature Med. 8:47-53; Walker et al., 2000, Blood 96:467-474; Ranga et al., 1998, Proc. Natl. Acad. Sci. U.S.A 95:1201-1206). More importantly, sustained increases in the total lymphocyte count, the CD4 to CD8 T cell ratio, the fraction of cytokine-secreting T cells, and the ability to respond to recall antigens were observed, suggesting that adoptive T cell immunotherapy can restore at least limited immune function back to HIV infected individuals (Levine et al., 2002, Nature Med. 8:47-53). Despite the success of these initial trials, several limitations were noted, including the difficulty of (1) expanding CD8 T cells, (2) adding additional costimulatory signals that may be required to expand certain subsets of T cells, (3) removing the beads before infusion and (4) generating antigen specific T cells with a high engraftment potential.

Others have used T cell expansion CD3/28 coated beads to introduce gene modified T cells to HIV infected patients. In these studies (Walker et al., 2000, Blood 96:467-474; Mitsuyasu et al., 2000, Blood 96:785-793; Deeks et al., 2002, Mol. Ther. 5:788-797), a chimeric molecule consisting of the extracellular domain of CD4 and the intracellular domain of the CD3 zeta chain (CD4ζ was introduced into CD4 T cells via retroviral transduction). CD4ζ-modified T cells were detected by DNA PCR in the peripheral blood of all patients following infusion, and mean levels of 1-3% of total peripheral blood mononuclear cells (PBMCs) were sustained at all post-infusion time points. In an extended follow-up, CD4ζ was detected in the blood of 17 of 18 patients one year following infusion. These levels of sustained engraftment are several orders of magnitude higher than what has been previously observed for human T cell infusions, perhaps because previous cell culture techniques may have induced susceptibility to apoptosis or replicative senescence (Rosenberg et al., 1990, N. Engl. J. Med. 323:570-578; Yee et al., 2002, Proc. Natl. Acad. Sci. U.S.A. 99:16168-16173; Brodie et al., 1999, Nature Med. 5:34-41; Riddell et al., 1996, Nature Med. 2:216-223; Riddell et al., 2000, Cancer Journal 6:S250-S258). These clinical results indicate that costimulated T cells propagated with bead-based aAPCs are safe and have the capacity for prolonged engraftment. However, due to the limited number of study subjects and length of time required to achieve a clinical endpoint in a HIV therapeutic trial, statistical significance of the clinical benefit of autologous CD4 T cell transfer to HIV infected individuals could not be measured.

While potentially effective in limiting immunodeficiency, polyclonal CD4 T cells are likely to have only a modest effect on the HIV specific response. Immunotherapy of human viral infection using adoptive transfer of antigen-specific CD8 T cells has been studied in the setting of CMV, EBV, and HIV infection. This approach has been evaluated using T cell clones with HLA-restricted antigenic specificity for CMV (Riddell et al., 1992, Science 257:238-241; Walter et al., 1995, N. Engl. J. Med. 333:1038-1044). CMV-specific CD8[+] T cells isolated from MHC-identical bone marrow donors were expanded ex vivo and were administered to 14 allogeneic bone marrow transplant recipients. Recovery of CMV-specific CTL activity was seen in each case and adoptively transferred CTL persisted in vivo for up to 12 weeks. In a similar study, donor-derived EBV-specific CD8+ and CD4+ T cells, genetically marked with the neomycin resistance gene, were administered to 6 recipients of T cell-depleted allogeneic bone marrow allografts (Rooney et al., 1995, Lancet 345:9-13; Heslop et al., 1996, Nature Med. 2:551-555). Gene-marked CD4+ and CD8+ T cells responsive to in vivo or ex vivo challenge with EBV persisted at low frequencies in vivo for as long as 18 months after infusion. Infusion of CD8 T cells with a single specificity to HIV (Nef) (Koenig et al., 1995, Nature Med. 1:330-336) into one patient demonstrated CTL selection of viral variants indicating that infusion of HIV specific T cells against multiple targets may be necessary to control HIV replication. In all of these studies, the inability of the vast majority of these T cells to engraft has limited the study of the long-term effects of antigen specific CD8 T cell immunotherapy. A major challenge in the field is to expand CD8 T cells that will engraft and have potent effector functions on a long-term basis to more effectively fight chronic infections. However, despite the long-term need for sufficient numbers of therapeutic T cells, there are no methods available for expanding these cells.

HIV specific T cells are able to contain but not eradicate HIV. Studies that have removed CD8 T cells prior to, or during, HIV infection have demonstrated unchecked viral replication and a much faster progression to AIDS, indicating that CD8 T cells are important in controlling HIV (Schmitz et al. 1999, Science 283:857-860; Jin et al., 1999, J. Exp. Med. 189:991-998). However, HIV specific T cells in general, lack perforin expression (Gandhi et al., 2002, Annu. Rev. Med. 53:149-172) and other requisite effector functions to eliminate HIV from the host. Studies of long term non-progressors indicated that HIV specific T cells from these individuals are more likely to proliferate and contain perforin, demonstrating that CD8 T cells with enhanced effector functions may delay the progression to AIDS (Migueles et al., 2002, Nature Immunol. 3:1061-1068). Other investigators have demonstrated that two key signaling receptors, CD3ζ and CD28 are down-regulated on HIV specific T cells (Trimble et al., 2000, Blood 96:1021-1029; Trimble et al., 1998, Blood 91:585-594; Trimble et al., 2000, J. Virol. 74:7320-7330), and that HIV-specific T cells are more sensitive to Fas induced apoptosis (Mueller et al., 2001, Immunity, 15:871-882). Appay et al. (2002, Nature Med. 8:379-385) examined the differences between HIV-, EBV-, and CMV-specific CD8 T cells based on CD27 and CD28 expression. Early differentiated T cells expressed both CD27 and CD28 and possessed poor effector functions but excellent proliferative abilities. Intermediate T cells were CD27 positive but CD28 negative, and these cells had limited proliferative and effector functions. The most differentiated T cells lack both CD27 and CD28, and these cells had little proliferative ability but enhanced effector functions. It was observed that most of the HIV-specific T cells had the intermediate phenotype. Therefore, the cells being "stuck" in this intermediate T cell phenotype that lack both proliferative capacity and effector functions may be the contributing factor to the ineffectiveness of HIV-specific T cells (Appay et al., 2002, Nature Med. 8, 379-385). Moreover, CD8 T cell function is highly dependent upon CD4 T cell function (Zajac et al., 1998, J. Exp. Med. 188:2205-2213; Shedlock et al., 2003, Science 300:337-339; Sun et al., 2003, Science 300:339-342) and since HIV targets CD4 T cells, the CD8 T cell defects observed in HIV infection could be the result of a lack of T cell help.

Thus, there exists a long-felt need to provide ways to stimulate T cells to combat various acute and chronic diseases and to promulgate sufficient numbers of therapeutic T cells for adoptive immunotherapy. The present invention meets this and other needs.

BRIEF SUMMARY OF THE INVENTION

The present invention includes an isolated artificial antigen presenting cell (aAPC), said aAPC comprising a K562 cell transduced using a lentiviral vector (LV), wherein said LV comprises a nucleic acid encoding at least one immune stimulatory ligand and at least one co-stimulatory ligand and further wherein said aAPC expresses said stimulatory ligand and said co-stimulatory ligand and can stimulate and expand a T cell contacted with said aAPC.

In one aspect of the present invention, the stimulatory ligand is a polypeptide selected from the group consisting of a major histocompatibility complex Class I (MHC class I) molecule loaded with an antigen, an anti-CD3 antibody, an anti-CD28 antibody, and an anti-CD2 antibody.

In another aspect of the present invention, said co-stimulatory ligand is at least one co-stimulatory ligand selected from the group consisting of CD7, B7-1 (CD80), B7-2 (CD86), PD-L1, PD-L2, 4-1BBL, OX40L, ICOS-L, ICAM, CD30L, CD40, CD70, CD83, HLA-G, MICA, MICB, HVEM, lymphotoxin beta receptor, ILT3, ILT4, 3/TR6, and a ligand that specifically binds with B7-H3.

In yet another aspect of the present invention, said co-stimulatory ligand specifically binds with at least one of a co-stimulatory molecule selected from the group consisting of CD27, CD28, 4-1BB, OX40, CD30, CD40, PD-1, ICOS, LFA-1, CD2, CD7, LIGHT, NKG2C, B7-H3, BTLA, Toll ligand receptor and a ligand that specifically binds with CD83.

In still another aspect of the present invention, said co-stimulatory ligand is an antibody that specifically binds with at least one molecule selected from the group consisting of CD27, CD28, 4-1BB, OX40, CD30, CD40, PD-1, ICOS, LFA-1, CD2, CD7, LIGHT, NKG2C, B7-H3, Toll ligand receptor and a ligand that specifically binds with CD83.

In one aspect of the present invention, said aAPC further comprises Fcγ receptor selected from the group consisting of a CD32 molecule and a CD64 molecule.

In another aspect of the present invention, said LV comprises a nucleic acid encoding at least one antigen selected from the group consisting of a tumor antigen, a viral antigen, a bacterial antigen, a peptide-MHC tetramer, a peptide-MHC trimer, a peptide-MHC dimer, and a peptide-MHC monomer.

In yet another aspect of the present invention, said tumor antigen is selected from the group consisting of MAGE-1, MAGE-2, MAGE-3, MART-1, GP100, CEA, HER-2/Neu, PSA, WT-1, MUC-1, MUC-2, MUC-3, MUC-4, and telomerase.

In still another aspect of the present invention, said LV comprises a nucleic acid encoding at least one peptide selected from a cytokine and a chemokine.

In yet another aspect of the present invention, said cytokine is at least one cytokine selected from the group consisting of IL-2, IL-4, IL-6, IL-7, IL-10, IL-12, IL-15, IL-21, interferon-alpha (IFNα), interferon-beta (IFNβ), interferon-gamma (IFNγ), tumor necrosis factor-alpha (TNFα), tumor necrosis factor-beta (TNFβ), granulocyte macrophage colony stimulating factor (GM-CSF), and granulocyte colony stimulating factor (GCSF).

The present invention includes a method for specifically inducing proliferation of a T cell expressing a known co-stimulatory molecule, said method comprising contacting said T cell with an aAPC of the invention, further wherein said co-stimulatory ligand specifically binds with said known co-stimulatory molecule, thereby specifically inducing proliferation of said T cell.

The present invention includes a method for specifically inducing proliferation of a T cell expressing a known co-stimulatory molecule, said method comprising contacting a population of T cells comprising at least one T cell expressing said known co-stimulatory molecule with an aAPC of the invention, wherein said aAPC expresses at least one co-stimulatory ligand that specifically binds with said known co-stimulatory molecule, wherein binding of said known co-stimulatory molecule with said co-stimulatory ligand induces proliferation of said T cell.

The present invention includes a method of specifically expanding a T cell population subset, said method comprising contacting a population of T cells comprising at least one T cell of said subset with an aAPC of the invention, wherein said aAPC comprises at least one co-stimulatory ligand that specifically binds with a co-stimulatory molecule on said T cell of said subset, wherein binding of said co-stimulatory molecule with said co-stimulatory ligand induces proliferation of said T cell of said subset, thereby specifically expanding a T cell population subset.

The present invention includes a method of identifying a co-stimulatory ligand, or combination thereof, that specifically induces activation of a T cell subset, said method comprising contacting a population of T cells with an aAPC of the invention, and comparing the level of proliferation of said T cell population with the level of proliferation of an otherwise identical population of T cells not contacted with said aAPC, wherein a greater level of proliferation of said T cells contacted with said aAPC compared with the level of proliferation of said otherwise identical population of T cells not contacted with said aAPC, is an indication that said co-stimulatory ligand specifically induces activation of said T cell.

The present invention includes a method for inducing a T cell response to an antigen in a mammal, said method comprising administering to said mammal the aAPC of the invention, wherein said aAPC further comprises an MHC Class I molecule loaded with said antigen, wherein said aAPC induces proliferation of a T cell specific for said antigen, thereby inducing a T cell response to said antigen in said mammal.

The present invention includes a method of inducing a T cell response to an antigen in a mammal in need thereof, said method comprising obtaining a population of cells from said mammal wherein said population comprises T cells, contacting said population of cells with an aAPC of the invention, wherein said aAPC further comprises an MHC Class I complex loaded with said antigen, whereby contacting said cells with said aAPC induces proliferation of an antigen-specific T cell specific for said antigen, isolating said antigen-specific T cell from said population of cells, and administering said antigen-specific T cells to said mammal, thereby inducing a T cell response to said antigen in said mammal.

The present invention includes a method of specifically expanding a population of T regulatory (Treg) cells, the method comprising contacting said population with an aAPC of claim 1, wherein said aAPC further comprises an Fcγ receptor loaded with an anti-CD3 antibody and an anti-CD28 antibody, the method further comprising contacting said population of cells with a cytokine, wherein binding of said anti-CD3 antibody and said anti-CD28 antibody with said Treg cells induces proliferation of said Treg cells, thereby specifically expanding a population of Treg cells.

In one aspect of the invention, said cytokine is interleukin-2.

The present invention includes a kit for specifically inducing proliferation of a T cell expressing a known co-stimulatory molecule, said kit comprising an effective amount of an aAPC, wherein said aAPC comprises a K562 cell transduced using a lentiviral vector (LV), wherein said LV comprises a nucleic acid encoding at least one co-stimulatory ligand that specifically binds said known co-stimulatory molecule, wherein binding of said known co-stimulatory molecule with said co-stimulatory ligand stimulates and expands said T cell, said kit further comprising an applicator and an instructional material for the use of said kit.

The present invention includes a kit for specifically inducing proliferation of a T cell expressing a known stimulatory molecule, said kit comprising an effective amount of an aAPC, wherein said aAPC comprises a K562 cell transduced using a lentiviral vector (LV) wherein said LV comprises a nucleic acid encoding at least one stimulatory ligand that specifically binds said known stimulatory molecule, wherein binding of said known stimulatory molecule with said stimulatory ligand stimulates and expands said T cell, said kit further comprising an applicator and an instructional material for the use of said kit.

The present invention includes a kit for specifically expanding a T cell population subset, said kit comprising an effective amount of an aAPC, wherein said aAPC comprises a K562 cell transduced using a lentiviral vector (LV), wherein said LV comprises a nucleic acid encoding at least one co-stimulatory ligand that specifically binds a co-stimulatory molecule on said T cell population, wherein binding of said co-stimulatory molecule with said co-stimulatory ligand stimulates and expands said T cell population, said kit further comprising an applicator and an instructional material for the use of said kit.

The present invention includes a kit for identifying a co-stimulatory ligand, or combination of said ligands, that specifically induces activation of a T cell subset, said kit comprising a plurality of aAPCs wherein each said aAPC comprises a K562 cell transduced using a lentiviral vector (LV), wherein said LV comprises a nucleic acid encoding at least one known co-stimulatory ligand that specifically binds with a co-stimulatory molecule, said kit further comprising an applicator and an instructional material for the use of said kit.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts an engineered K32/4-1BBL aAPC interacting with a CD8+ T cell.

FIG. 2, comprising FIG. 2A depicts a series of images demonstrating the sorting of CD8 T cells from an HLA-A2 donor who had been exposed to the flu virus. FIG. 2B is a graph demonstrating that these cells were able to be maintained in culture for 70 days. The total number of cells that would have accumulated if no cells have been discarded is depicted as a semi-log plot of total cell number versus days in culture. FIG. 2C demonstrates a chromium release assay using loaded TAP deficient HLA-A2 positive T2 cells with either the flu peptide or leaving them unpulsed at the indicated Effector to Target ratios.

FIG. 3, comprising FIGS. 3A through 3E, illustrates the creation of an aAPC that can be used to expand flu specific T cells. FIG. 3 depicts a series of five (5) images demonstrating FACS analysis for each of the markers CD32 (FIG. 3A), KA2 (FIG. 3B), 4-1BBL (FIG. 3D), and FluGFP (green fluorescence protein, FIG. 3E) by aAPCs and also depicting an isotype control.

Figure 4:
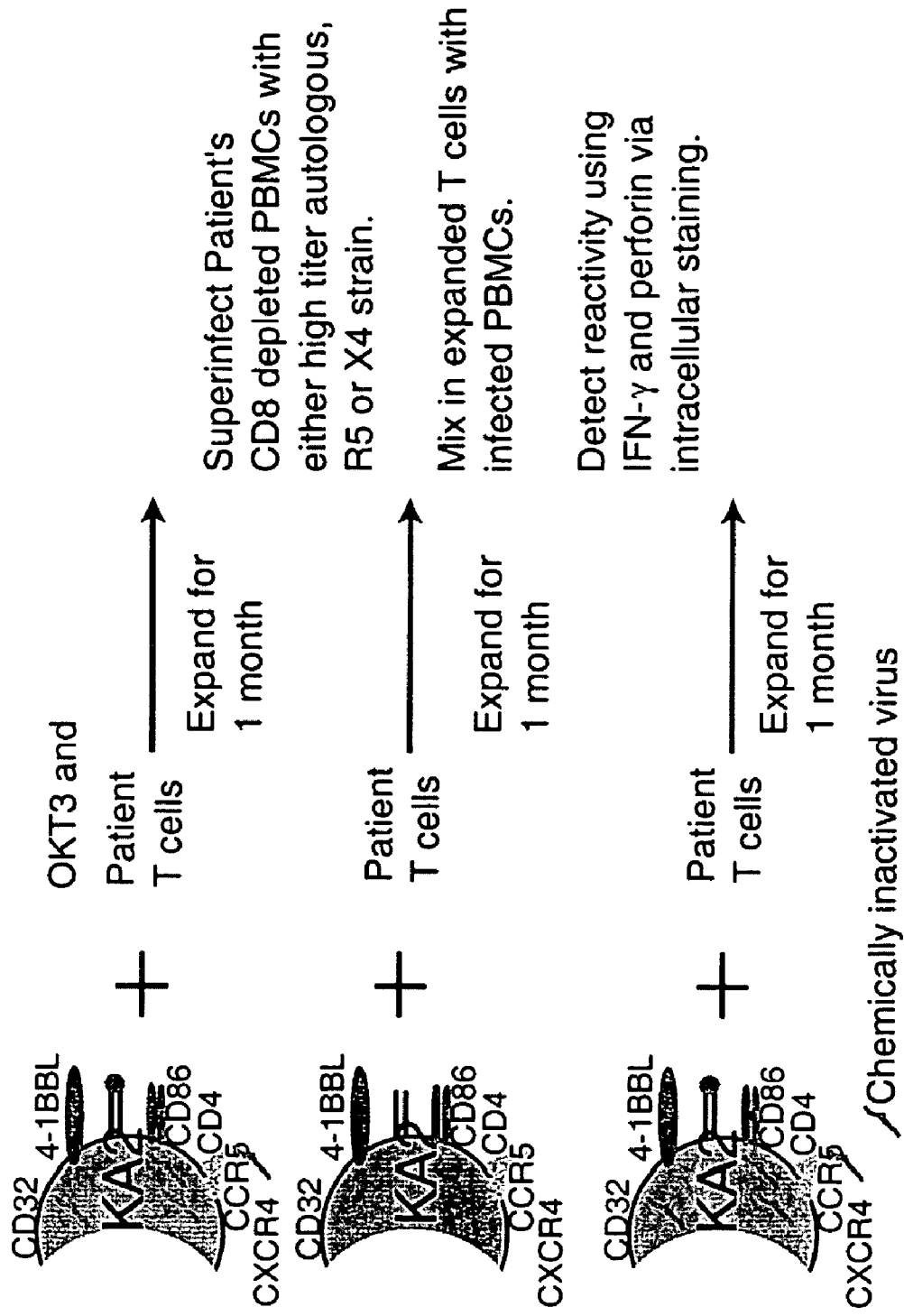

FIG. 4 is a diagram illustrating an experimental model demonstrating methods of expanding HIV specific CD8 T cells with a broad specificity.

Figure 5:
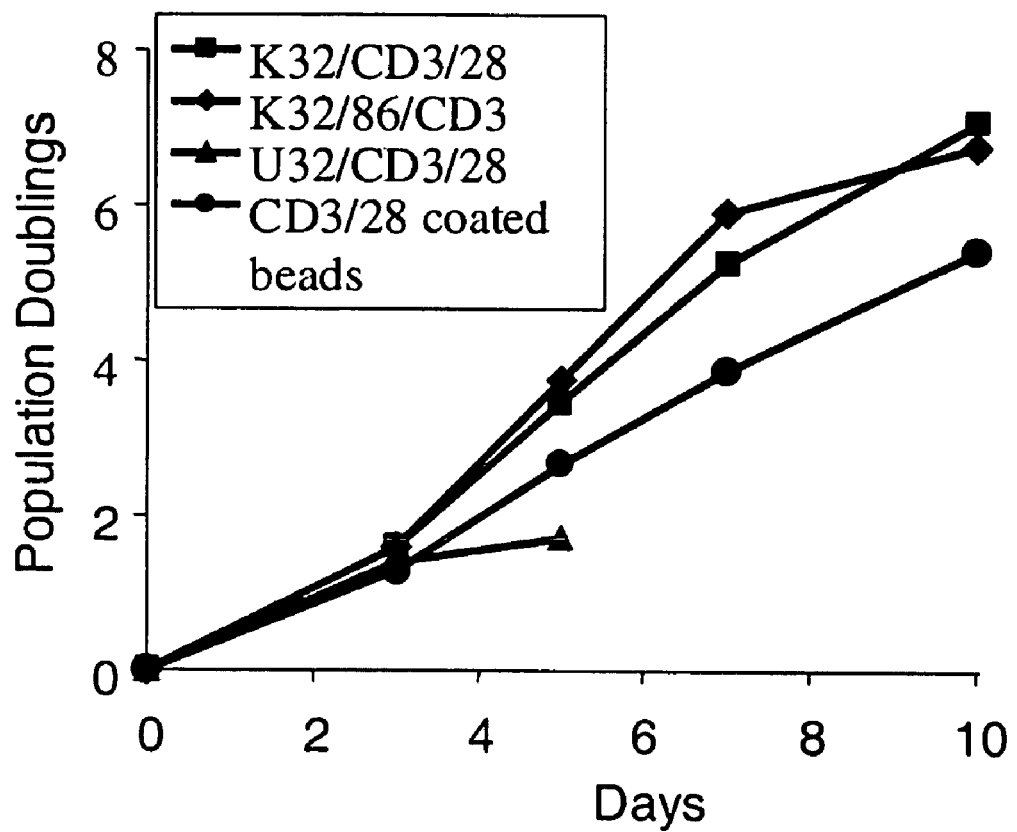

FIG. 5 is a graph demonstrating that K562-based aAPCs (e.g., K32/CD3/28, K32/86/CD3) mediate long-term growth of CD4 T cells and do so more effectively than U937-based aAPCs (U32/CD3/28) or bead-based aAPCs (CD3/28 coated beads).

Figures 6A, 6B:
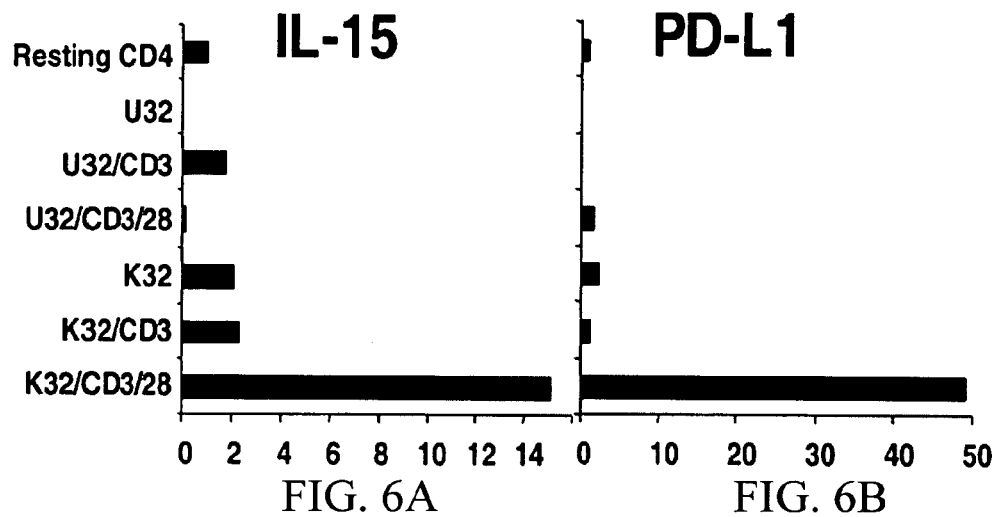
Figures 6C, 6D:
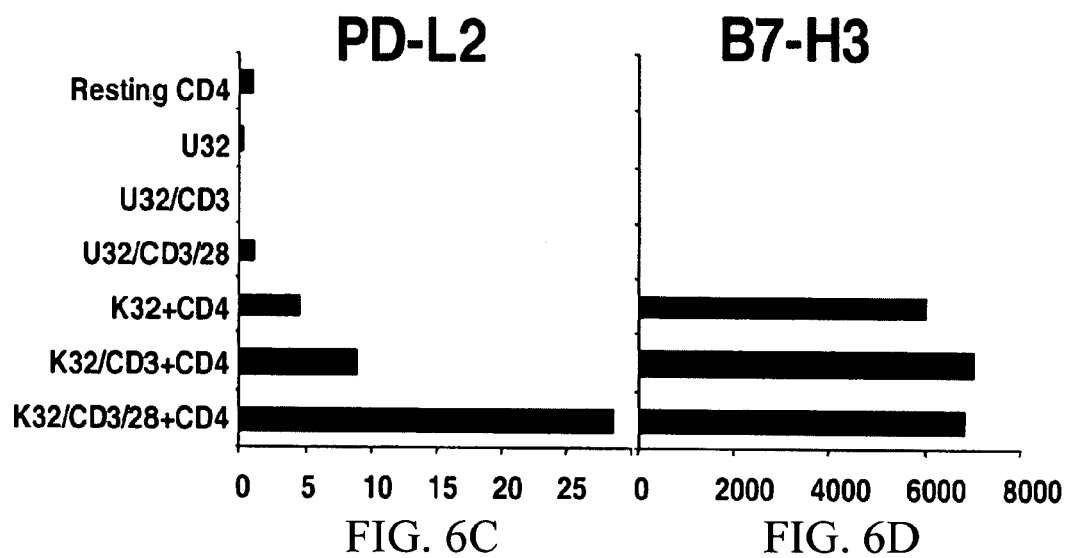

FIG. 6, comprising FIGS. 6A through 6D, is a graph demonstrating induction of cytokine and costimulatory gene expression on K562-based aAPCs but not U937-based aAPCs. FIG. 6A is a graph depicting that the level of induction of interleukin 15 (IL-15) by K32/CD3/28, K32/CD3, K32, U32/CD3/28, U32/CD3, U32, and resting CD4 T cells. FIG. 6B depicts PD-L1 induction in the cells, demonstrating that the K32/CD3/28 aAPCs express substantially higher levels of PD-L1. FIG. 6C is a graph depicting induction of PD-L2 by various aAPCs as described supra. FIG. 6D is a graph depicting induction of B7-H3 by various aAPCs.

Figure 7:
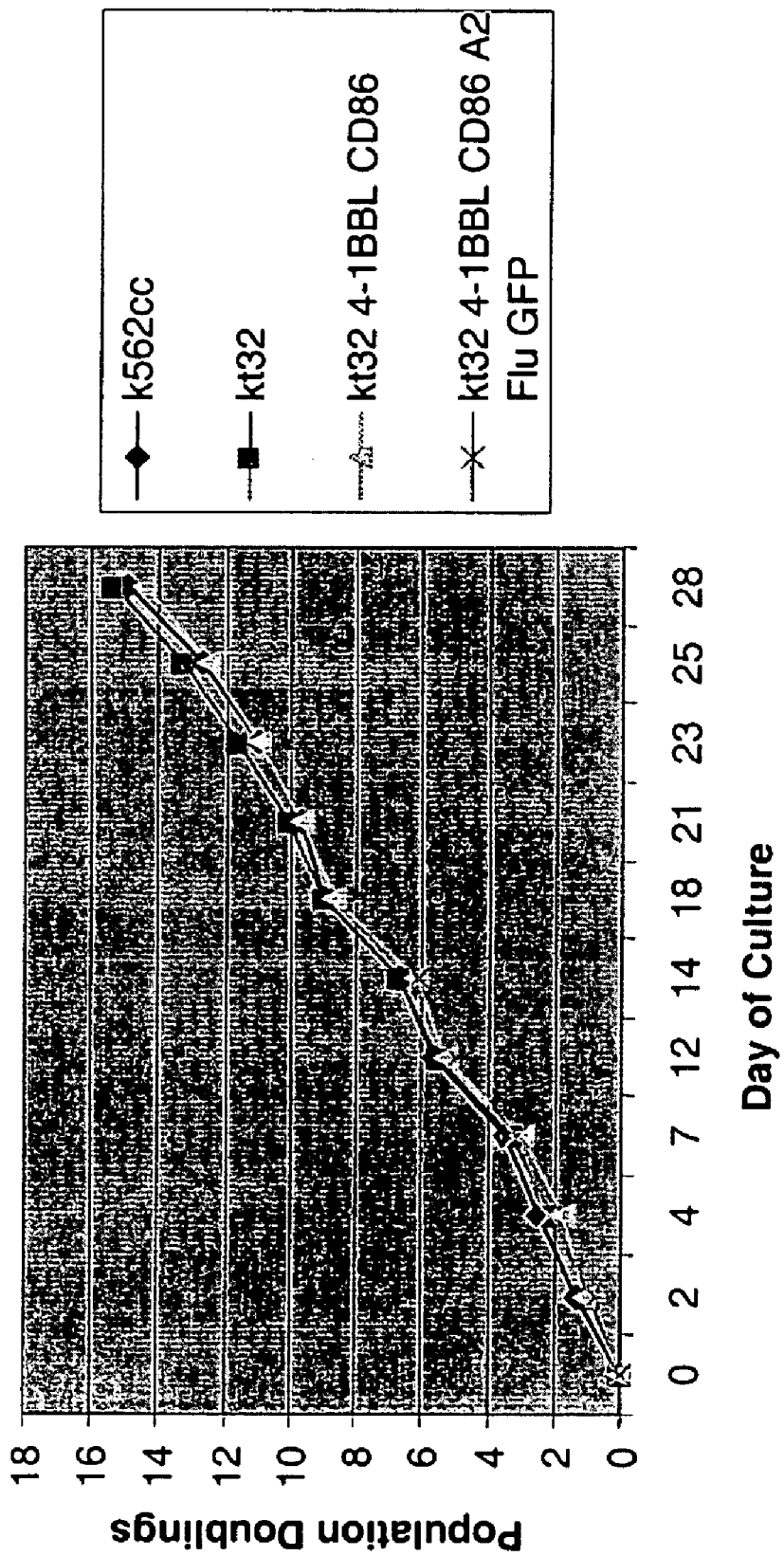

FIG. 7 is a diagram depicting the growth rate of lentivirus (LV) transduced aAPCs cultured in Aim V media (Invitrogen, Carlsbad, Calif.) supplemented with 3% Human Ab serum (Valley Biomedical, Winchester, Va.). Various K562-based aAPCs were produced by transducing parental K562 (k562cc; dark diamonds) using the following LV vectors constructs: KT32 (1 gene; dark squares); KT32/4-1BBL/CD86 (3 genes; light triangles); KT32/4-1BBL/CD86/A2/Flu-GFP (5 genes; "X"). The total number of cells that would have accumulated if no cells have been discarded is depicted as a semi-log plot of total cell number versus days in culture.

FIG. 8, comprising FIGS. 8A through 8E, is a graph depicting the stable co-expression of at least eight (8) genes in a single K562 aAPC (8-THREAT). The following genes were transduced into a K562 cell and were stably expressed, as detected using flow cytometry: Flu-GFP (FIG. 8A); CD80 (FIG. 8B); CD86 (FIG. 8C); 4-1BBL (FIG. 8D); and HLA ABC (FIG. 8E).

Figure 9:
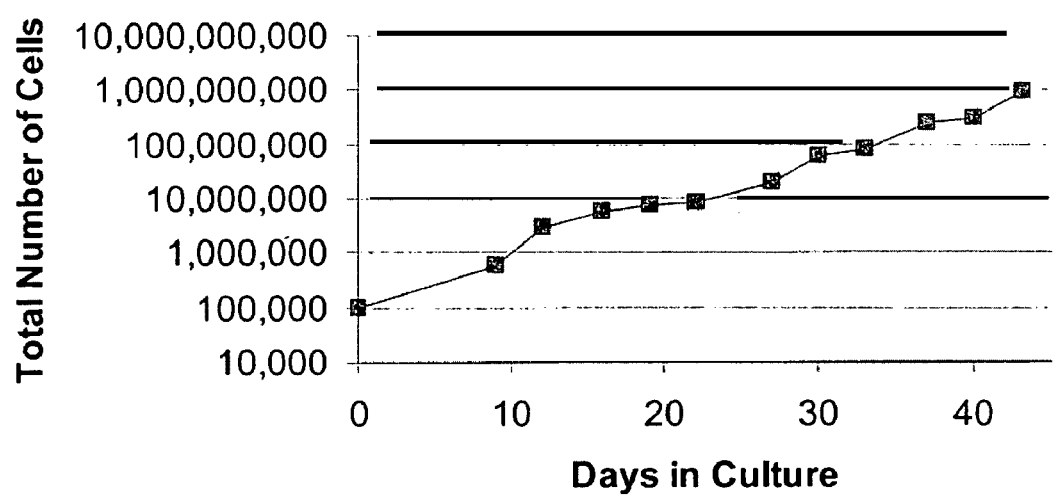

FIG. 9 is a graph demonstrating long term expansion of polyclonal CD8 T cells using LV-transduced aAPCs.

FIG. 10, comprising FIGS. 10A-10E, is a series of graphs demonstrating that K32/4-1BBL aAPC expanded hTERT specific cytotoxic lymphocytes (CTL). FIGS. 10A through 10C are graphs depicting the increasing percentage of tet+ CD8 CTLs during expansion by K32/4-1BBL aAPC. The timing of the MoFlo sorting corresponding to each FIG. 10A-10C is indicated on the graph showing population doublings (FIG. 10D). FIG. 10D is a graph depicting the expansion of hTERT-specific CTLs by the aAPC, where the CTLs were obtained from a breast cancer patient vaccinated with hTERT. FIG. 10E is a graph demonstrating that the hTERT specific CTLs expanded using the aAPC specifically lyse carcinoma cells expressing HLA-A2 and telomerase+ (OV-7) but not carcinoma cells that are telomerase+ but that are HLA-A2- (SK-OV-3).

Figure 11A:
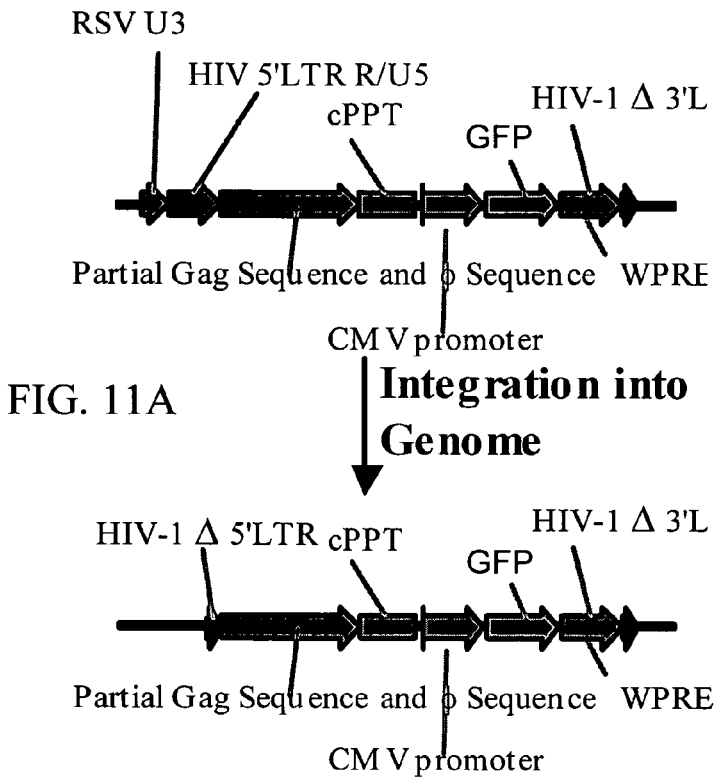
Figure 11B:
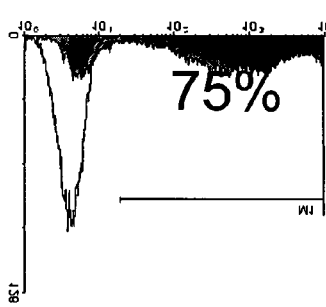
Figure 11C:
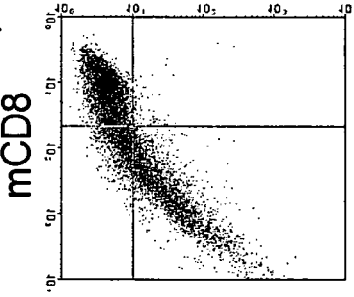
Figure 11D:
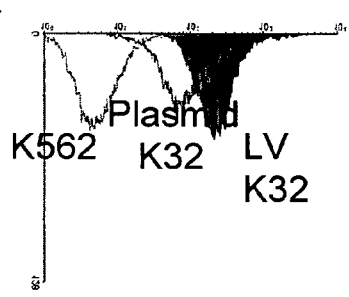

FIG. 11, comprising FIG. 11A through FIG. 11D, depicts data comparing transfection of aAPCs using a plasmid with expression of molecules transduced into an otherwise identical aAPC using an LV. FIG. 11A is a diagram depicting an exemplary LV used herein, depicting the particular modifications as disclosed elsewhere herein. FIGS. 11B and 11C depict the transduction efficiency of K562 cells of a single inoculum of GFP expressing virus (monocistronic) or mCD8 IRES GFP (bicistronic). Surface expression of mCD8 and GFP was measured 5 days after transduction.

FIG. 12, comprising FIGS. 12A through 12F, depicts a representative experiment, wherein 8,000 antigen-specific T cells were observed to yield 2X106 cells after one month of culture. Briefly, purified T cells obtained from an HLA A*0201 donor were stained with anti-CD8 mAb and an A*0201 MHC tetramer complexed to an A*0201 restricted epitope of the influenza matrix protein (flu-MP tetramer). The tetramer positive population (about 8000 cells) was sorted and stimulated with irradiated KTA2/CD32/4-1BBL/FLU GFP aAPCs that were loaded with anti-CD28 antibody. The cells were re-stimulated with KTA2/CD32/4-1BBL/FLU GFP aAPCs (FIG. 12A-D) approximately every 10-12 days. Interleukin 2 (IL-2) was added to the culture at every cell feeding (every 2-3 days). FIGS. 12E and 12F graphs demonstrating purity of flu tetramer reactive cells prior and after 26 days of expansion. That is, about 250-fold expansion of tetramer positive population was observed under these culture conditions.

Figure 13:
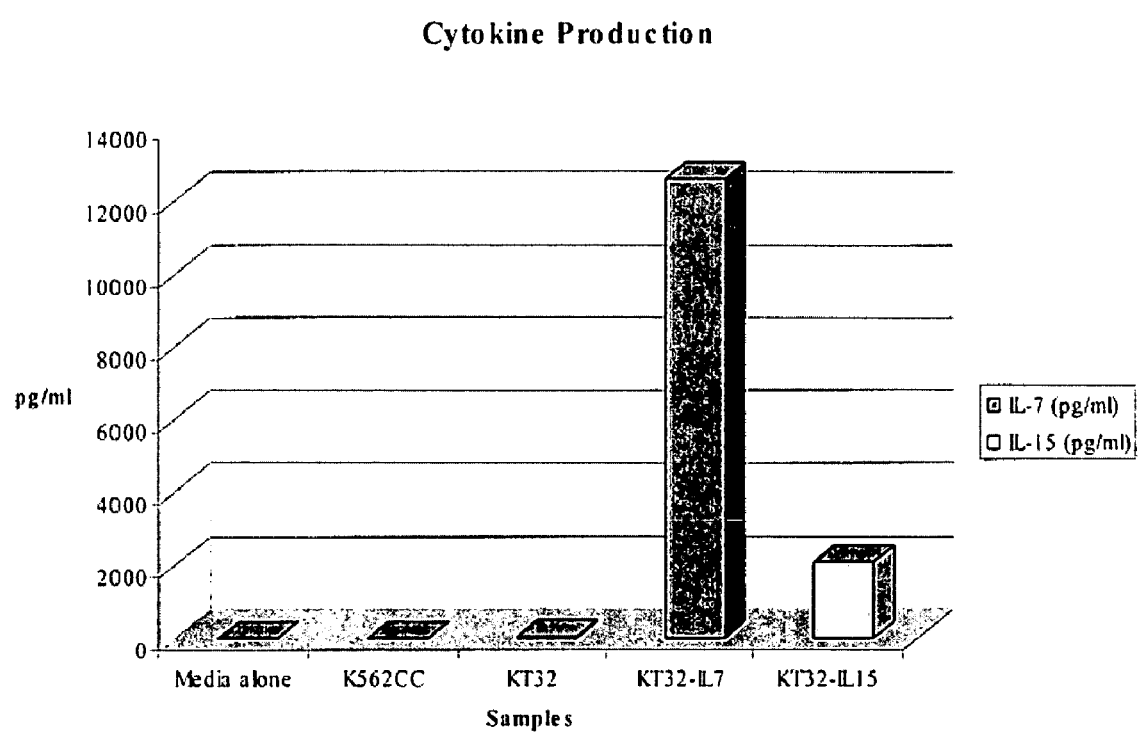

FIG. 13 is a bar graph depicting the level of cytokine expression using a K562 aAPC transduced with CD32 IRES IL-7 (KT32-IL7) and K562 transduced with CD32 IRES IL-15 (KT32-IL15) where the cells were sorted for high CD32 expression.

Figure 14:
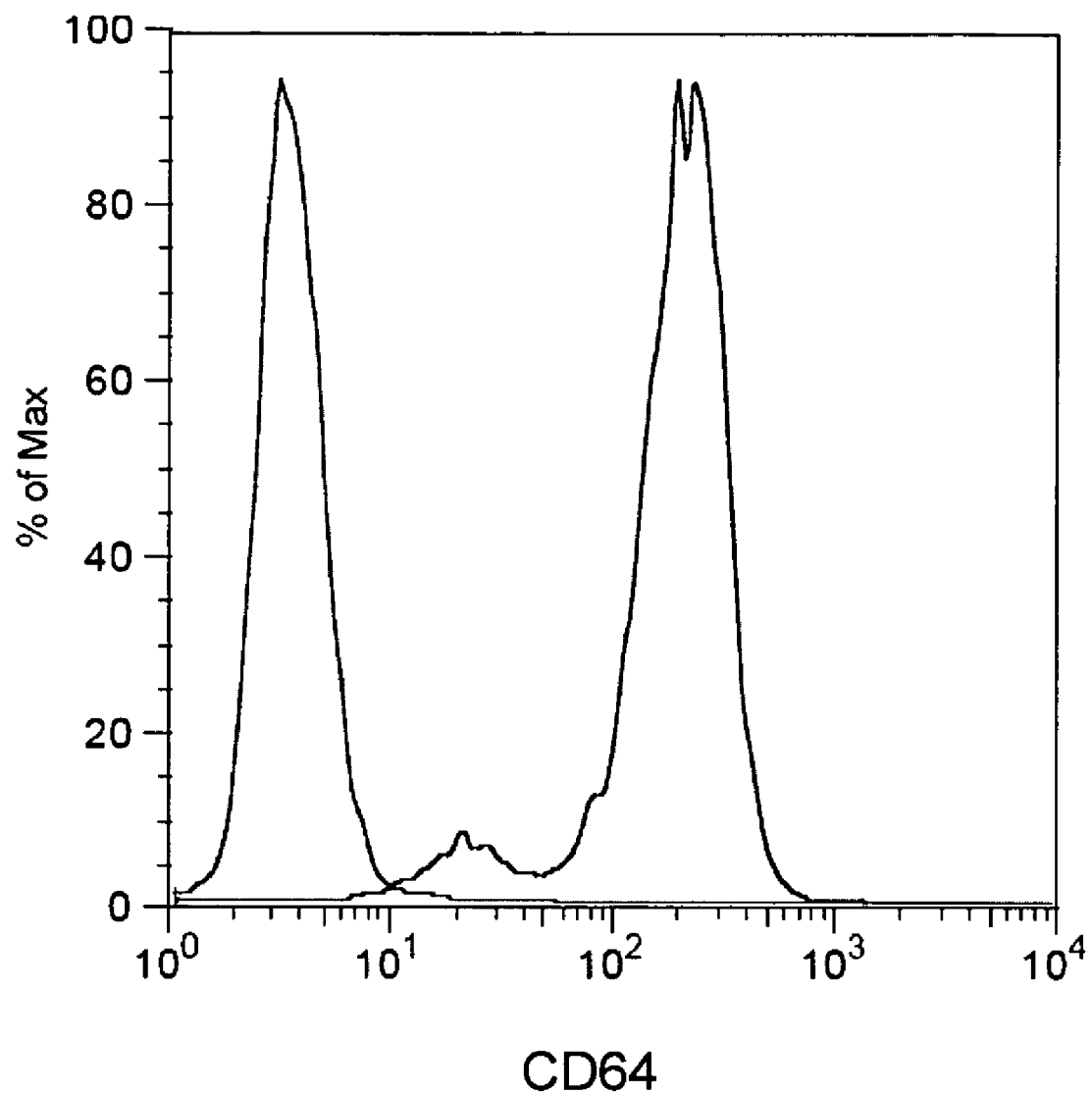

FIG. 14 is a plot demonstrating the stable expression of CD64 on the surface of a K562 cell transduced with a lentiviral vector expressing CD64.

Figure 15:
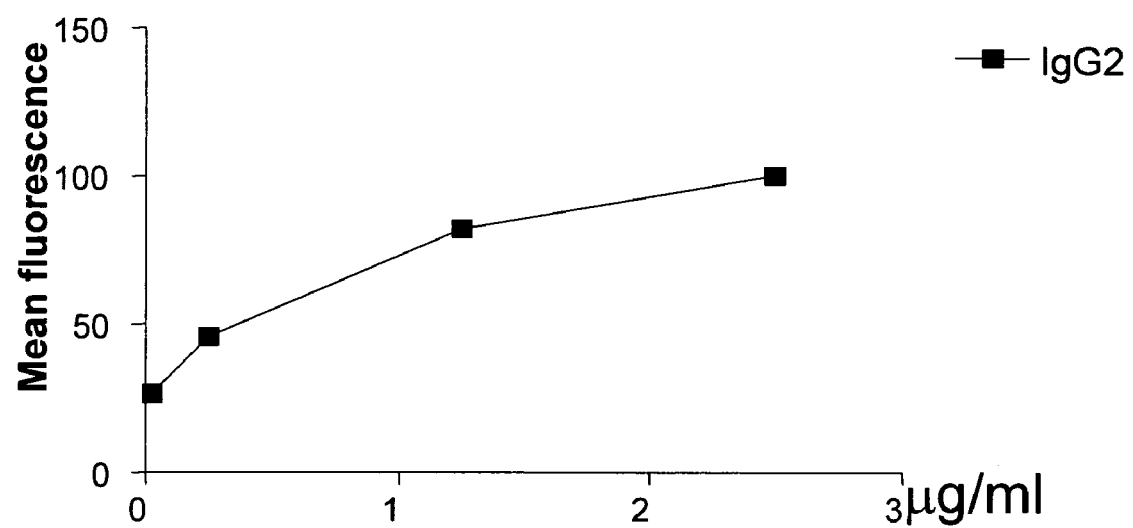

FIG. 15 is a graph illustrating the increased antibody binding capacity of K562 cells transfected with a lentiviral vector expressing CD64 (K64 cells).

Figure 16:
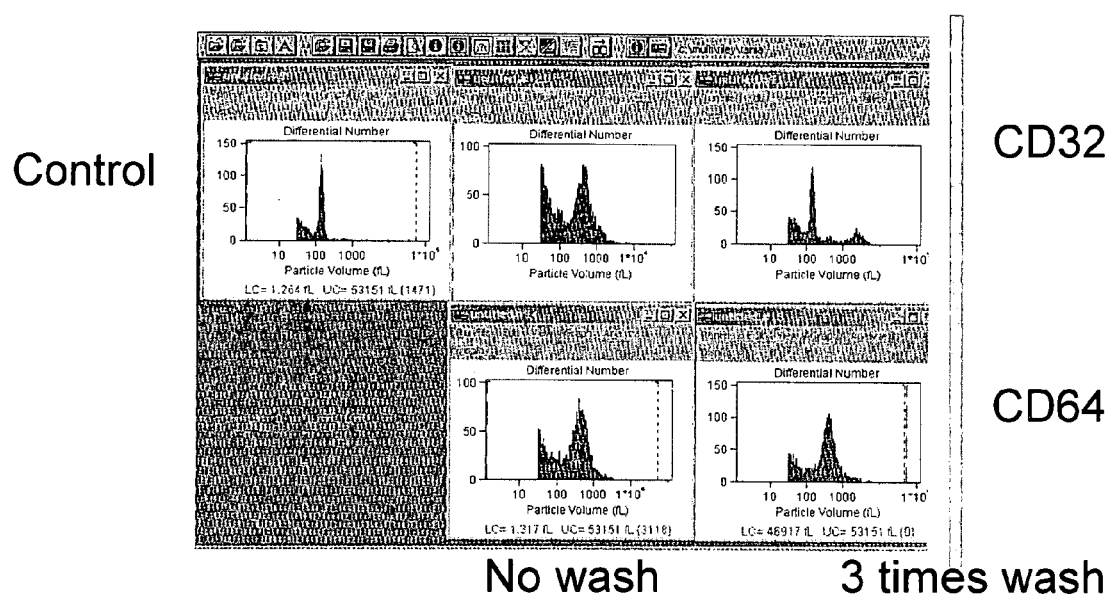

FIG. 16 is a series of graphs illustrating that K64 cells loaded with antibody and washed multiple times are superior at stimulating T cells when compared with K562 cells expressing CD32 (K32 cells), although both K64 cells and K32 cells are capable of stimulating T cells.

Figure 17:
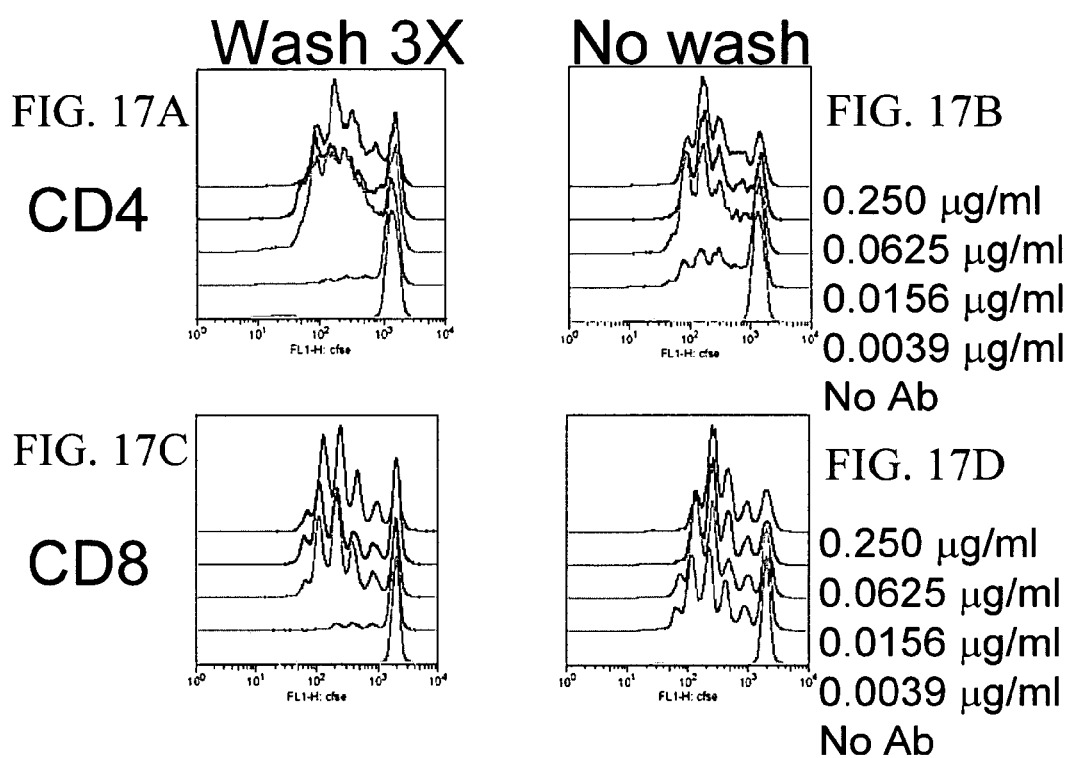

FIG. 17, comprising FIGS. 17A through 17D is a series of images illustrating that much less antibody is required to optimally load K64 cells when compared to K32 cells. FIGS. 17A and 17B depict CD4 cells, FIGS. 17C and 17D depict CD8 cells.

Figure 18:
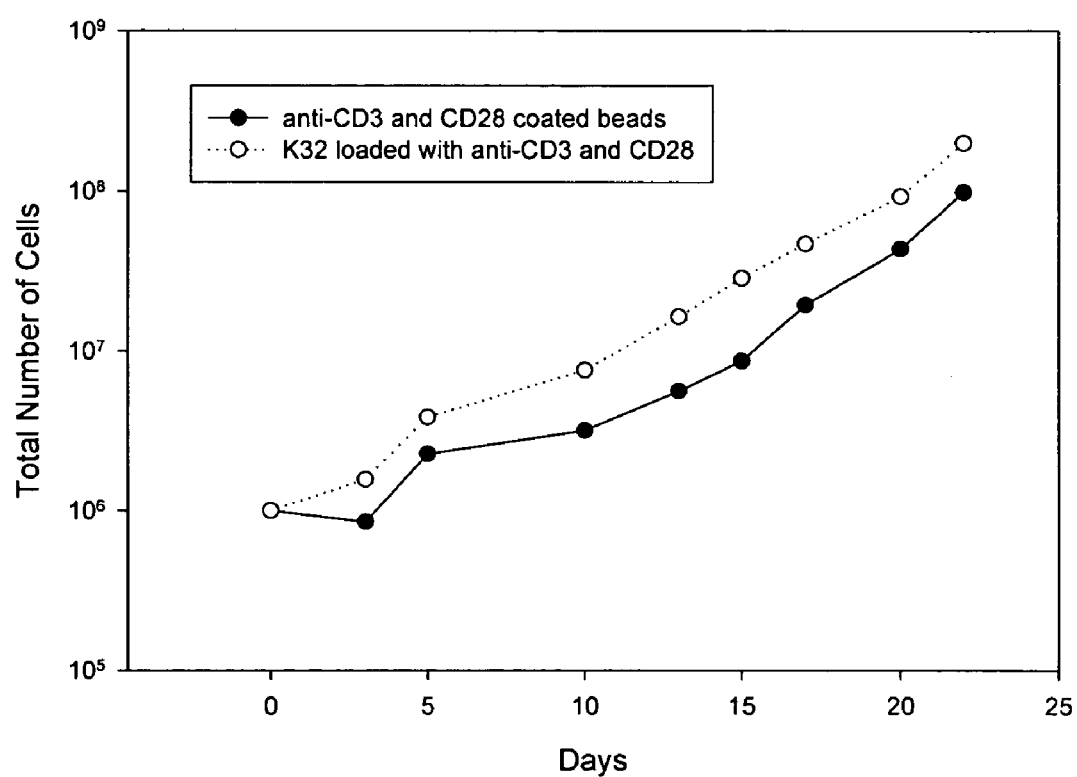

FIG. 18 is a graph illustrating the increased expansion of Treg cells stimulated with K32 cells loaded with anti-CD3 and anti-CD28 antibodies compared to Treg cells stimulated with anti-CD3 and anti-CD28 coated beads.

Figure 19:
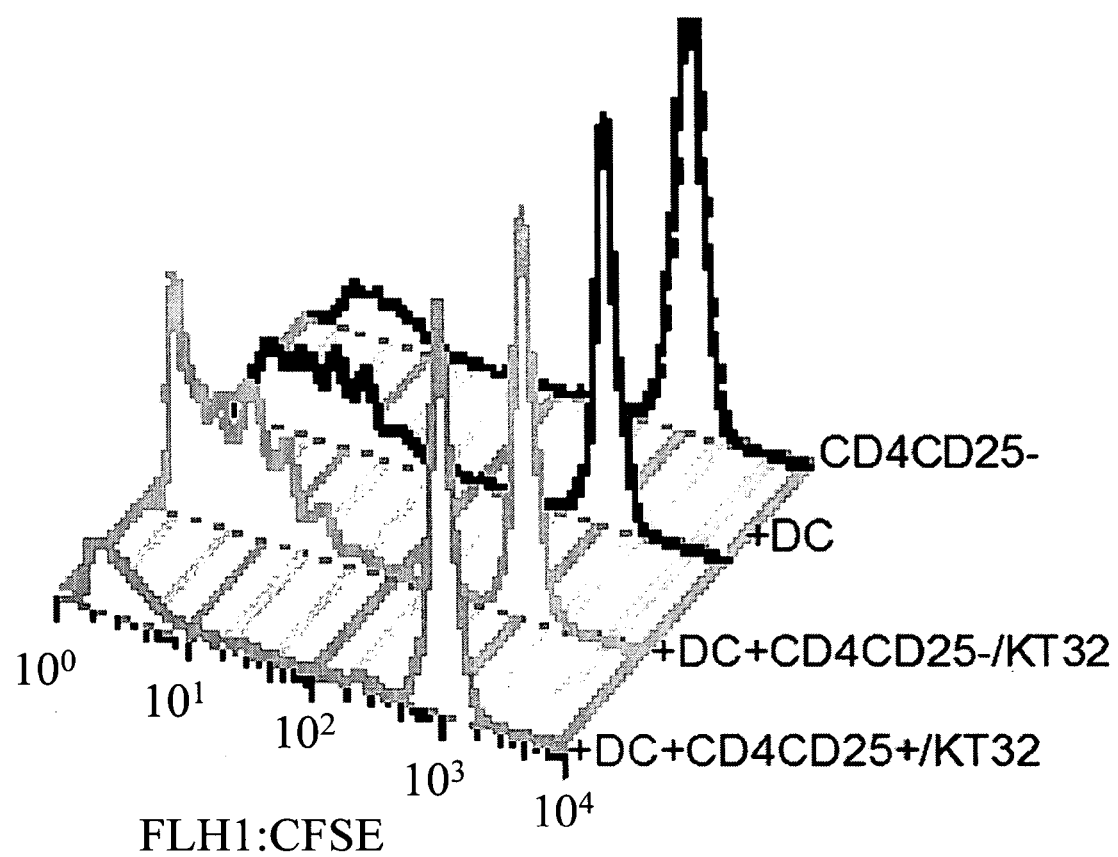

FIG. 19 is a graph depicting the ability of Treg cells to suppress an allogeneic mixed lymphocyte reaction (MLR).

Figure 20:
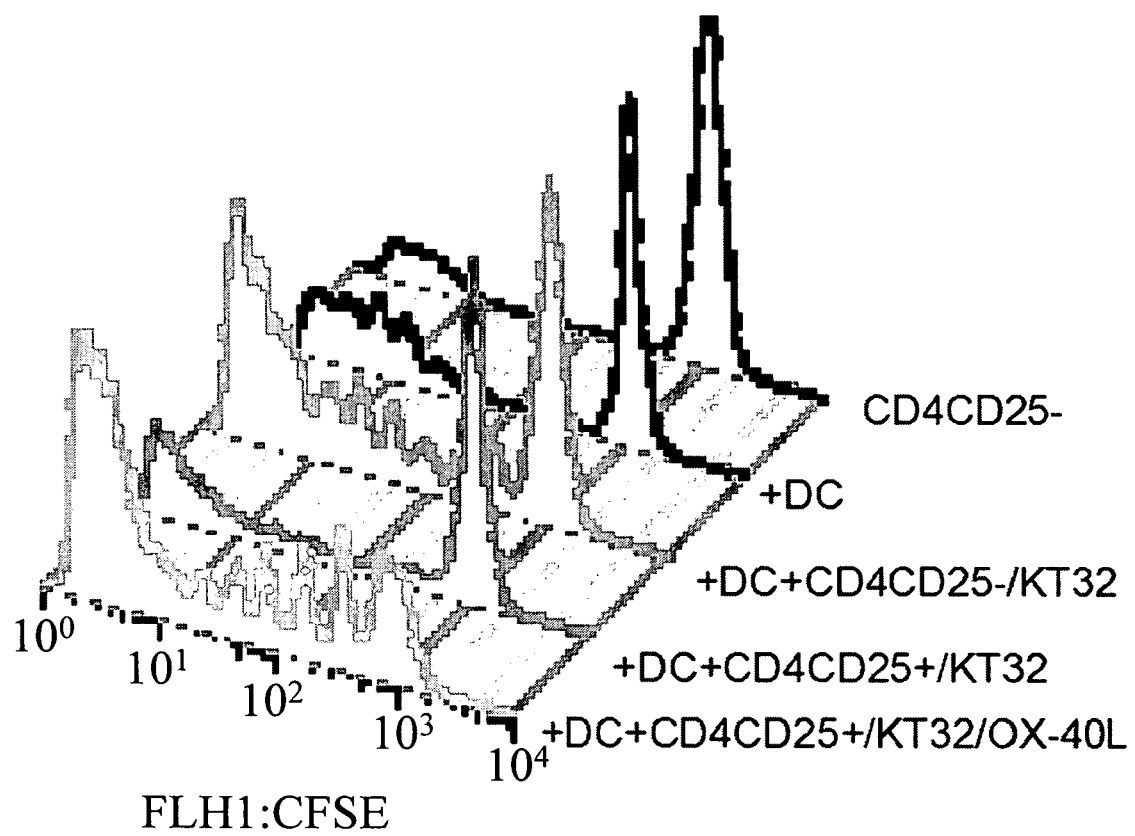

FIG. 20 is a graph demonstrating the $CD4^+$ $CD25^+$ Treg cells stimulated using K32 cells expressing OX40L render the Treg cells non-suppressive.

FIG. 21, comprising FIGS. 21A through 21C, is a series of images illustrating the expansion of antigen specific CD8 cells using K32 loaded with anti-CD3 antibody and expressing IL-15, 4-1BBL and CD80.

DETAILED DESCRIPTION OF THE INVENTION

The invention relates to the surprising discovery that lentivirus vectors can be used to efficiently produce aAPCs that stably express numerous T cell stimulatory and co-stimulatory ligands, and antibodies thereto, as well as antigens, cytokines, among other molecules. The invention also relates to the novel aAPCs produced and methods for their use to expand a desired T cell, activate and/or expand specific T cell subsets, identify stimulatory molecules, co-stimulatory molecules, and combinations thereof, that can promote expansion of specific T cell subsets, as well as numerous therapeutic uses relating to expansion and stimulation of T cells using the novel aAPCs.

As demonstrated by the data disclosed herein, upon T cell activation, factors such as IFNγ are secreted that in turn induce the expression of cytokines such as IL-15 and costimulatory ligands such as B7-H3 in K562 cells (Thomas et al., 2002, Clin. Immunol. 105:259-272). The interchange or "crosstalk" between the aAPC and a T cell is a reason why cell-based aAPCs are more efficient T cell expansion systems than bead-based aAPCs. K562 cells are engineered such that these cells are a continuously renewable "off the shelf" dendritic cell (DC) replacement system. Use of aAPCs would obviate the time and expense required to generate autologous DC as a source of APC for cell culture. Additional costimulatory signals may be necessary to rescue effector functions from HIV-specific CD8 T cells and as demonstrated by the data herein, aAPC cells can be modified to express such signals as desired. Again, this is an advantage over bead-based systems which do not encompass adding additional costimulatory signals that may be required to expand certain subsets of T cells.

Previously, cell-based aAPCs were created by electroporation of K562 cells with CD32 and 4-1BBL expression plasmids. Using a combination of drug selection, cell sorting, and limiting dilution, high-expressing clones were isolated (Maus et al., 2002, Nature Biotechnol. 20:143-148). While effective, this approach is both time consuming and limited by the need to use drug selection markers. Reliance of drug selection restricts the number of constructs that can be introduced into K562 cells and raises GMP compliance issues when clinical use is contemplated.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a disease means reducing the severity of one or more symptoms of the disease.

As used herein, "amino acids" are represented by the full name thereof, by the three-letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator," as the term is used herein, is meant any device including, but not limited to, a hypodermic syringe, a pipette, and the like, for administering the compounds and compositions of the invention.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "effective amount", as used herein, is meant an amount that when administered to a mammal, causes a detectable level of T cell response compared to the T cell response detected in the absence of the compound. T cell response can be readily assessed by a plethora of art-recognized methods.

The skilled artisan would understand that the amount of the compound or composition administered herein varies and can be readily determined based on a number of factors such as the disease or condition being treated, the age and health and physical condition of the mammal being treated, the severity of the disease, the particular compound being administered, and the like.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

By "complementary to a portion or all of the nucleic acid encoding" a protein of the invention, is meant a sequence of nucleic acid which does not encode a, e.g., costimulatory ligand protein. Rather, the sequence which is being expressed in the cells is identical to the non-coding strand of the nucleic acid encoding the protein and thus, does not encode the protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, lentiviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 18 nucleotides in length, preferably, at least about 24 nucleotides, more typically, from about 24 to about 50 nucleotides, preferably, at least about 50 to about 100 nucleotides, even more preferably, at least about 100 nucleotides to about 200 nucleotides, yet even more preferably, at least about 200 to about 300, even more preferably, at least about 300 nucleotides to about 400 nucleotides, yet even more preferably, at least about 400 to about 500, and most preferably, the nucleic acid fragment will be greater than about 500 nucleotides in length.

As applied to a protein, a "fragment" of a stimulatory or costimulatory ligand protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length.

A "genomic DNA" is a DNA strand which has a nucleotide sequence homologous with a gene as it exists in the natural host. By way of example, a fragment of a chromosome is a genomic DNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding a chromogenic substrate such as o-nitrophenyl-β-galactoside to the medium (Gerhardt et al., eds., 1994, Methods for General and Molecular Bacteriology, American Society for Microbiology, Washington, D.C., p. 574).

A "restriction site" is a portion of a double-stranded nucleic acid which is recognized by a restriction endonuclease.

A first oligonucleotide anneals with a second oligonucleotide "with high stringency" if the two oligonucleotides anneal under conditions whereby only oligonucleotides which are at least about 73%, more preferably, at least about 75%, even more preferably, at least about 80%, even more preferably, at least about 85%, yet more preferably, at least about 90%, and most preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an aAPC, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

As used herein, to "treat" means reducing the frequency with which symptoms of a disease (i.e., viral infection, tumor growth and/or metastasis, or other effect mediated by decreased numbers and/or decreased activity of T cells, and the like) are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of a nucleic acid that encodes a protein and/or antibody of the invention, to the patient, or to the aAPC, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a lentiviral vector, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

A "therapeutic" treatment is a treatment administered to a patient who exhibits signs of pathology for the purpose of diminishing or eliminating those signs and/or decreasing or diminishing the frequency, duration and intensity of the signs.

An "effective amount" of a compound is that amount of a cell (e.g., an aAPC or T cell stimulated and/or expanded thereby) which is sufficient to provide a detectable effect to a population of T cells, or to a mammal, to which the aAPC is administered and/or contacted with when compared to an otherwise identical population of T cells, or mammal, to which the aAPC, or T cell expanded thereby, is not administered.

The skilled artisan would understand that the effective amount varies and can be readily determined based on a number of factors such as the disease or condition being treated, the age and health and physical condition of the mammal being treated, the severity of the disease, the particular compound or cell being administered, the level of activity or expression of the aAPC or T cell expanded thereby, and the like. Generally, the effective amount will be set between about 0.1 mg/kg to about 100 mg/kg, more preferably from about 1 mg/kg and 25 mg/kg. The compound or cell (e.g., a cytokine, a stimulatory molecule or ligand thereto, a costimulatory molecule or ligand thereto, an antibody that specifically binds with a ligand, a nucleic acid encoding such proteins, an aAPC, a T cell expanded thereby, and the like) can be administered through intravenous injection, or delivered to a tumor site, and includes, among other things, a bolus injection. However, the invention is not limited to this, or any other, method of administration.

A "therapeutic" treatment is a treatment administered to a patient who exhibits signs of pathology for the purpose of diminishing or eliminating those signs and/or decreasing or diminishing the frequency, duration and intensity of the signs.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell (e.g., an aAPC of the invention, among others).

"Loaded" with a peptide, as used herein, refers to presentation of an antigen in the context of an MHC molecule. "Loaded" as used herein also means the binding of an antibody to an Fc binding receptor on a cell, such as CD32 and/or CD64.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible COStimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

"Superagonist antibody," as used herein, means an antibody that specifically binds with a molecule on a T cell and can mediate a primary activation signal event in a T cell without interaction of the TCR/CD3 complex or CD2 on the T cell. Such superagonist antibody includes, but is not limited to, a superagonist anti-CD3 antibody, a superagonist anti-CD28 antibody, and a superagonist anti-CD2 antibody.

Unless referred to as a "superagonist", an anti-CD2 antibody, an anti-CD28 antibody, and the like, is a co-stimulatory ligand as defined elsewhere herein, and provides a co-stimulatory signal rather than a primary activation signal.

To "treat" a disease as the term is used herein, means to reduce the frequency of the disease or disorder reducing the frequency with which a symptom of the one or more symptoms disease or disorder is experienced by an animal.

By the term "vaccine" as used herein, is meant a composition, a protein or a nucleic acid encoding a protein, or an aAPC of the invention, which serves to protect an animal against a disease and/or to treat an animal already afflicted with a disease by inducing an immune response, compared with an otherwise identical animal to which the vaccine is not administered or compared with the animal prior to the administration of the vaccine.

"Immunovaccine," as used herein, means an aAPC that can elicit a detectable immune response when administered to an animal. More preferably, an immunovaccine is an aAPC that stimulates and activates T cells when administered to the animal, such that it generates a detectable T cell immune response to a pathogen, a tumor cell, and the like, when compared to a T cell the immune response, if any, in an otherwise identical animal to which the immunovaccine is not administered.

DESCRIPTION

The invention relates to the surprising discovery that a human erythromyeloid cell line, K562, that does not express MHC class I or class II molecules, and which was previously believed to be refractory to genetic manipulation techniques, can be readily transduced using lentivirus vectors to express numerous molecules, including, but not limited to, stimulatory ligands, co-stimulatory ligands, antigens (e.g., tumor, viral, and the like), cytokines, etc.

Further, the data disclosed herein demonstrate that several (at least nine) exogenous nucleic acids expressing several proteins can be readily introduced into and expressed in these cells, but that the level of expression of the proteins is higher than that achieved using plasmid-based expression systems and the expression is stable and continues for many months without detectable decrease. In addition, the K562-based artificial antigen presenting cell (aAPC), which does not express MHC class I or II molecules, can be transduced with and readily expresses them. Remarkably, aAPC transduced with a nucleic acid encoding an antigen of interest processed the antigen and presented it properly to a T cell thereby producing antigen-specific T cells without need to identify the epitope recognized by the T cell. Surprisingly, as demonstrated by the data disclosed herein, the aAPC cell properly processed and presented the antigen.

I. Compositions

The present invention encompasses an isolated artificial antigen presenting cell (aAPC), where the cell comprises a K562 cell transduced using a lentiviral vector (LV). Moreover, the LV encodes at least one immune stimulatory and co-stimulatory ligand. While the data disclosed herein demonstrate that about nine nucleic acids encoding about nine different molecules transduced into a K562 cell were stably and highly expressed in long-term culture, there is nothing to suggest that this is a limit in the number or kinds of molecules that can be introduced into these cells. Instead, any molecule or ligand, whether stimulatory, co-stimulatory, cytokine, antigen, Fcγ receptor, and the like, can be introduced into these cells to produce an aAPC of the invention.

The skilled artisan would appreciate, based upon the disclosure provided herein, that numerous immunoregulatory molecules can be used to produce an almost limitless variety of aAPCs once armed with the teachings provided herein. That is, there is extensive knowledge in the art regarding the events and molecules involved in activation and induction of T cell, and treatises discussing T cell mediated immune responses, and the factors mediating them, are well-known in the art. Further, the extensive disclosure provided in WO 03/057171 and US2003/0147869 is incorporated by reference as if set forth in its entirety herein. More specifically, a primary signal, usually mediated via the T cell receptor/CD3 complex on a T cell, initiates the T cell activation process. Additionally, numerous co-stimulatory molecules present on the surface of a T cell are involved in regulating the transition from resting T cell to cell proliferation. Such co-stimulatory molecules, also referred to as "co-stimulators", which specifically bind with their respective ligands, include, but are not limited to, CD28 (which binds with B7-1 [CD80], B7-2 [CD86]), PD-1 (which binds with ligands PD-L1 and PD-L2), B7-H3, 4-1BB (binds the ligand 4-1BBL), OX40 (binds ligand OX40L), ICOS (binds ligand ICOS-L), and LFA (binds the ligand ICAM). Thus, the primary stimulatory signal mediates T cell stimulation, but the co-stimulatory signal is then required for T cell activation, as demonstrated by proliferation.

Thus, the aAPC of the invention encompasses a cell comprising a stimulatory ligand that specifically binds with a TCR/CD3 complex such that a primary signal is transduced. Additionally, as would be appreciated by one skilled in the art, based upon the disclosure provided herein, the aAPC further comprises at least one co-stimulatory ligand that specifically binds with at least one co-stimulatory molecule present on a T cell, which co-stimulatory molecule includes, but is not limited to, CD27, CD28, CD30, CD7, a ligand that specifically binds with CD83, 4-1BB, PD-1, OX40, ICOS, LFA-1, CD30L, NKG2C, B7-H3, MHC class I, BTLA, Toll ligand receptor and LIGHT. This is because, as discussed previously and as demonstrated by the data disclosed elsewhere herein, a co-stimulatory signal is required to induce T cell activation and associated proliferation. Other co-stimulatory ligands are encompassed in the invention, as would be understood by one skilled in the art armed with the teachings provided herein. Such ligands include, but are not limited to, a mutant, a variant, a fragment and a homolog of the natural ligands described previously.

These and other ligands are well-known in the art and have been well characterized as described in, e.g., Schwartz et al., 2001, Nature 410:604-608; Schwartz et al., 2002, Nature Immunol. 3:427-434; and Zhang et al., 2004, Immunity. 20:337-347. Using the extensive knowledge in the art concerning the ligand, the skilled artisan, armed with the teachings provided herein would appreciate that a mutant or variant of the ligand is encompassed in the invention and can be transduced into a cell using a LV to produce the aAPC of the invention and such mutants and variants are discussed more fully elsewhere herein. That is, the invention includes using a mutant or variant of a ligand of interest and methods of producing such mutants and variants are well-known in the art and are not discussed further herein.

Thus, the aAPC of the invention comprises at least one stimulatory ligand and at least one co-stimulatory ligand, such that the aAPC can stimulate and expand a T cell comprising a cognate binding partner stimulatory molecule that specifically binds with the stimulatory ligand on the aAPC and a cognate binding partner co-stimulatory molecule that specifically binds with the co-stimulatory ligand on the aAPC such that interaction between the ligands on the aAPC and the corresponding molecules on the T cell mediate, among other things, T cell proliferation, expansion and immune response as desired. One skilled in the art would appreciate that where the particular stimulatory and co-stimulatory molecules on a T cell of interest are known, an aAPC of the invention can be readily produced to expand that T cell. Conversely, where the stimulatory and co-stimulatory molecules on a T cell of interest are not known, a panel of aAPCs of the invention can be used to determine which molecules, and combinations thereof, can expand that T cell. Thus, the present invention provides tools for expansion of desirable T cells, as well as tools for elucidating the molecules on particular T cells that mediate T cell activation and proliferation.

The skilled artisan would understand that the nucleic acids of the invention encompass an RNA or a DNA sequence encoding a protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook and Russell (2001, Molecular Cloning, A Laboratory Approach, Cold Spring Harbor Press, Cold Spring Harbor, N.Y.), and Ausubel et al. (2002, Current Protocols in Molecular Biology, John Wiley & Sons, NY). Procedures for the introduction of amino acid changes in a protein or polypeptide by altering the DNA sequence encoding the polypeptide are well known in the art and are also described in these, and other, treatises.

The invention includes a nucleic acid encoding a costimulatory ligand, or antigen, wherein a nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one protein of the invention, or biologically active fragment thereof. Such tag polypeptides are well known in the art and include, for instance, green fluorescent protein (GFP), an influenza virus hemagglutinin tag polypeptide, a herpesvirus tag polypeptide, myc, myc-pyruvate kinase (myc-PK), $His_6$, maltose binding protein (MBP), a FLAG tag polypeptide, and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize a protein of the invention, or a biologically active fragment thereof, within a cell, a tissue, and/or a whole organism (e.g., a human, and the like), and to study the role(s) of the protein in a cell. Further, addition of a tag polypeptide facilitates isolation and purification of the "tagged" protein such that the proteins of the invention can be produced and purified readily. More importantly, as demonstrated elsewhere herein, expression of a costimulatory ligand comprising a tag allows the detection of expression of the ligand, and further permits isolation of cells expressing the ligand using many methods, including, but not limited to, cell sorting.

The present invention also provides for analogs of proteins or peptides which comprise a costimulatory ligand as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are costimulatory ligands, cytokines, antigens (e.g., tumor cell, viral, and other antigens), which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a costimulatory ligand, cytokine, antigen, and the like, of the present invention (e.g., expression by an aAPC where contacting the aAPC expressing the protein with a T cell, mediates proliferation of, or otherwise affects, the T cell).

Among a "biological activity", as used herein, is included a costimulatory ligand which when transduced into a K562 cell is expressed and, when the cell is contacted with a T cell expressing a cognate costimulatory molecule on its surface, it mediates activation and stimulation of the T cell, with induced proliferation.

Indeed, the present invention provides a powerful novel screening assay for the identification of mutants, variants, fragments, and homologs of costimulatory ligands in that a potential novel form of a costimulatory ligand can be transduced and expressed in the aAPC of the invention. The ability of the aAPC to stimulate and/or activate a T cell can be assessed and compared with the ability of an aAPC comprising the wild type or "natural" costimulatory ligand to stimulate and/or activate an otherwise identical T cell. In this way, functional variants, demonstrating the ability to activate/stimulate the T cell to a greater, lesser or equal extent as the control wild type ligand, can be readily identified, isolated and characterized. Such novel variants of costimulatory ligands are potential research tools for elucidation of T cell processes, and also provide important potential therapeutics based on inhibiting or inducing T cell activation/stimulation, such as, but not limited to, administration of a variant with inhibitory activity which can compete with the natural ligand to inhibit unwanted T cell responses such as, but not limited to, transplant rejection. Conversely, a variant demonstrating greater costimulatory ligand activity can be used to increase a desired T cell response, such as, but not limited to, administration to an immunosuppressed patient. For instance, an exemplary variant ligand can be engineered to be more effective that the natural ligand or to favor the binding of a positive costimulatory molecule (CD28) at the expense of a negative regulator (CTLA-4). These, and many other variations are encompassed in the invention.

One skilled in the art would appreciate, based upon the disclosure provided herein, that a costimulatory ligand encompasses an antibody that specifically binds with the costimulatory molecule present on a T cell that the ligand also binds with. That is, the invention encompasses an aAPC comprising not only a costimulatory ligand (e.g., CD80 and CD86, among others) that bind a costimulatory molecule on a T cell (e.g., CD28), but also encompasses at least one antibody that specifically binds with the costimulatory molecule (e.g., anti-CD28). Numerous antibodies to the costimulatory molecules are presently available, or they can be produced following procedures that are well-known in the art.

The skilled artisan would understand, based upon the disclosure provided herein, that an aAPC comprising an antibody can be produced, as exemplified elsewhere herein, by introducing a nucleic acid encoding CD32, the human Fcγ receptor, into the aAPC. Further, as disclosed elsewhere herein, an aAPC that binds an antibody, such as a CD3 antibody or an CD28 antibody, can be produced by expressing a nucleic acid encoding CD64 on the aAPC. CD64 is the high affinity human FcγRI receptor. The CD32 and/or CD64 expressed on the aAPC surface can then be "loaded" with any desired antibody that binds with CD32 and/or CD64, including, but not limited to, antibody that specifically binds CD3 and antibody that specifically binds with CD28. Moreover, the invention encompasses an aAPC wherein a nucleic acid encoding the antibody ligand of interest, perhaps linked to an IRES sequence, is transduced and expressed on the surface of the aAPC thereby eliminating the need for expression of CD32 and/or CD64 and loading thereof. Thus, the present invention includes an aAPC transduced with a nucleic acid encoding at least one antibody that specifically binds with CD3, CD28, PD-1, B7-H3, 4-1BB, OX40, ICOS, CD30, HLA-DR, MHCII, Toll Ligand Receptor and LFA, among others, as well as an aAPC transduced with CD32 and/or CD64 and loaded with at least one antibody that specifically binds with the afore-mentioned molecules.

Further, the invention encompasses an aAPC wherein the co-stimulatory ligand is a cognate binding partner that specifically binds with a co-stimulatory molecule, as well as where the ligand is an antibody that specifically binds with a costimulatory molecule, and any combination thereof, such that a single aAPC can comprise both nucleic acids encoding costimulatory ligands and/or antibodies specific for costimulatory molecules present on the Tcell, and any combination thereof.

The invention also encompasses an aAPC comprising a nucleic acid encoding an antigen of interest. A wide plethora of antigens are included, such as, but not limited to, tumor antigens, e.g., telomerase, melanoma antigen recognized by T cells (MART-1), melanoma antigen-encoding genes, 1, 2, and 3 (MAGE-1, -2, -3), melanoma GP100, carcinoembryonic antigen (CEA), breast cancer antigen HER-2/Neu, serum prostate specific antigen (PSA), Wilm's Tumor 1 (WT-1), mucin antigens (MUC-1, -2, -3, -4), and B cell lymphoma idiotypes. This is because, as demonstrated by the data disclosed elsewhere herein, K562-based aAPC comprising an antigen, can process and present the antigen in the context of MHC (where the cell is also transduced with a nucleic acid encoding a MHC class I or class II molecule) thereby producing antigen-specific T cells and expanding a population thereof. The data disclosed demonstrate that hTERT-specific CTLs were produced by expanding hTERT+ T cells using an aAPC transduced with CD32 and 4-1BBL (K32/4-1BBL). Thus, aAPCs can be used to expand and produce sufficient antigen specific T cells in order to administer the T cells to a patient in need thereof thus providing an immunovaccine treatment directed against tumor cells bearing the antigen. Therefore, an antigen of interest can be introduced into an aAPC of the invention, wherein the aAPC then presents the antigen in the context of the MCH Class I or II complex, i.e., the MHC molecule is "loaded" with the antigen, and the aAPC can be used to produce an antigen-specific T cell.

Similarly, a viral, or any other pathogen, antigen can also be transduced and expressed by the aAPC. The data disclosed elsewhere herein demonstrate that matrix protein (flu-MP tetramer) positive T cells sorted and stimulated irradiated aAPC cells (K2/CD3/4-1BBL/FLU-GFP) loaded with anti-CD28 antibody expanded the T cells providing large numbers of antigen specific CTLs specific for the viral antigen. These data demonstrate that the aAPCs of the invention can be used to expand and produce antigen-specific T cells to be used to treat viral, and other pathogenic, infections.

Additionally, the invention encompasses an aAPC transduced with a nucleic acid encoding at least one cytokine, at least one chemokine, or both. This is because the data disclosed elsewhere herein amply demonstrate that an aAPC transduced with a nucleic acid encoding an interleukin (e.g., IL-7, IL-15, and the like) stably expressed the interleukin. Moreover, using a LV vector comprising an internal ribosome entry site (IRES), the interleukin can be secreted from the aAPCs (e.g., a K562 transduced with a LV vector such as, but not limited to, pCLPS CD32-IRES-IL-7, -12, -15, -18, and -21). Other cytokines that can be expressed by aAPC include, but are not limited to, interferon-γ (IFNγ), tumor necrosis factor-α (TNFα), SLC, IL-2, IL-4, IL-23, IL-27 and the like. The invention further includes, but is not limited to, chemokine RANTES, MIP-1a, MIP-1b, SDF-1, eotaxin, and the like.

Thus, the invention encompasses a cytokine, including a full-length, fragment, homologue, variant or mutant of the cytokine. A cytokine includes a protein that is capable of affecting the biological function of another cell. A biological function affected by a cytokine can include, but is not limited to, cell growth, cell differentiation or cell death. Preferably, a cytokine of the present invention is capable of binding to a specific receptor on the surface of a cell, thereby affecting the biological function of a cell.

A preferred cytokine includes, among others, a hematopoietic growth factor, an interleukin, an interferon, an immunoglobulin superfamily molecule, a tumor necrosis factor family molecule and/or a chemokine. A more preferred cytokine of the invention includes a granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, among many others.

A chemokine, including a homologue, variant, mutant or fragment thereof, encompasses an alpha-chemokine or a beta-chemokine, including, but not limited to, a C5a, interleukin-8 (IL-8), monocyte chemotactic protein 1alpha (MIP1α), monocyte chemotactic protein 1 beta (MIP1β), monocyte chemoattractant protein 1 (MCP-1), monocyte chemoattractant protein 3 (MCP-3), platelet activating factor (PAFR), N-formyl-methionyl-leucyl-[$^3$H]phenylalanine (FMLPR), leukotriene B$_4$ (LTB$_{4R}$), gastrin releasing peptide (GRP), RANTES, eotaxin, lymphotactin, IP10, I-309, ENA78, GCP-2, NAP-2 and/or MGSA/gro. One skilled in the art would appreciate, once armed with the teachings provided herein, that the invention encompasses a chemokine and a cytokine, such as are well-known in the art, as well as any discovered in the future.

The skilled artisan would appreciate, once armed with the teachings provided herein, that the aAPC of the invention is not limited in any way to any particular antigen, cytokine, costimulatory ligand, antibody that specifically binds a costimulatory molecule, and the like. Rather, the invention encompasses an aAPC comprising numerous molecules, either all expressed under the control of a single promoter/regulatory sequence or under the control of more than one such sequence. Moreover, the invention encompasses administration of one or more aAPC of the invention where the various aAPCs encode different molecules. That is, the various molecules (e.g., costimulatory ligands, antigens, cytokines, and the like) can work in cis (i.e., in the same aAPC and/or encoded by the same contiguous nucleic acid or on separate nucleic acid molecules within the same aAPC) or in trans (i.e., the various molecules are expressed by different aAPCs).

In this way, as would be understood by one skilled in the art, based upon the disclosure provided herein, the dose and timing of administration of the aAPCs can be specifically tailored for each application. More specifically, where it is desirable to provide stimulation to a T cell using certain molecules expressed by an aAPC, or several aAPCs, followed by stimulation using another aAPC, or several aAPCs, expressing a different, even if overlapping, set of molecules, then a combination of cis and trans approaches can be utilized. In essence, the aAPCs of the invention, and the methods disclosed herein, provide an almost limitless number of variations and the invention is not limited in any way to any particular combination or approach. The skilled artisan, armed with the teachings provided herein and the knowledge available in the art, can readily determine the desired approach for each particular T cell. Alternatively, based upon the disclosure provided herein, which provides methods for assessing the efficacy of the T cell stimulation and expansion methods disclosed herein, the skilled artisan can determine which approach(es) can be applied to the particular T cells to be expanded or stimulated.

The skilled artisan would understand, based upon the disclosure provided herein, that various combinations of molecules to be expressed in the aAPCs of the invention may be favored. While several of these combinations of molecules are indicated throughout the specification, including, but not limited to, the combinations exemplified at Tables 1, 2, 3 and 4, the invention is in no way limited to these, or any other aAPC comprising any particular combination of molecules. Rather, one skilled in the art would appreciate, based on the teachings provided herein, that a wide variety of combinations of molecules can be transduced into a cell to produce the aAPC of the invention. The molecules encompass those known in the art, such as those discussed herein, as well as those molecules to be discovered in the future.

The invention encompasses the preparation and use of pharmaceutical compositions comprising an aAPC of the invention as an active ingredient. Such a pharmaceutical composition may consist of the active ingredient alone, as a combination of at least one active ingredient (e.g., an effective dose of an APC) in a form suitable for administration to a subject, or the pharmaceutical composition may comprise the active ingredient and one or more pharmaceutically acceptable carriers, one or more additional (active and/or inactive) ingredients, or some combination of these.

As used herein, the term "pharmaceutically acceptable carrier" means a chemical composition with which the active ingredient may be combined and which, following the combination, can be used to administer the active ingredient to a subject.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, intra-lesional, buccal, ophthalmic, intravenous, intra-organ or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers and AZT, protease inhibitors, reverse transcriptase inhibitors, interleukin-2, interferons, cytokines, and the like.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The aAPC of the invention and/or T cells expanded using the aAPC, can be administered to an animal, preferably a human. When the T cells expanded using an aAPC of the invention are administered, the amount of cells administered can range from about 1 million cells to about 300 billion. Where the aAPCs themselves are administered, either with or without T cells expanded thereby, they can be administered in an amount ranging from about 100,000 to about one billion cells wherein the cells are infused into the animal, preferably, a human patient in need thereof. While the precise dosage administered will vary depending upon any number of factors, including but not limited to, the type of animal and type of disease state being treated, the age of the animal and the route of administration.

The aAPC may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

An aAPC (or cells expanded thereby) may be co-administered with the various other compounds (cytokines, chemotherapeutic and/or antiviral drugs, among many others). Alternatively, the compound(s) may be administered an hour, a day, a week, a month, or even more, in advance of the aAPC (or cells expanded thereby), or any permutation thereof. Further, the compound(s) may be administered an hour, a day, a week, or even more, after administration of aAPC (or cells expanded thereby), or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and the aAPC (or cells expanded thereby), and the like.

Further, it would be appreciated by one skilled in the art, based upon the disclosure provided herein, that where the aAPC is to be administered to a mammal, the cells are treated so that they are in a "state of no growth"; that is, the cells are incapable of dividing when administered to a mammal. As disclosed elsewhere herein, the cells can be irradiated to render them incapable of growth or division once administered into a mammal. Other methods, including haptenization (e.g., using dinitrophenyl and other compounds), are known in the art for rendering cells to be administered, especially to a human, incapable of growth, and these methods are not discussed further herein. Moreover, the safety of administration of aAPC that have been rendered incapable of dividing in vivo has been established in Phase I clinical trials using aAPC transfected with plasmid vectors encoding some of the molecules discussed herein.

II. Methods

The invention encompasses a method for specifically inducing proliferation of a T cell expressing a known co-stimulatory molecule. The method comprises contacting a T cell that is to be expanded with an aAPC comprising a lentivirus vector encoding a ligand that specifically binds with that co-stimulatory molecule. As demonstrated elsewhere herein, contacting a T cell with a K562-based aAPC comprising, among other things, a costimulatory ligand that specifically binds a cognate costimulatory molecule expressed on the T cell surface, stimulates the T cell and induces T cell proliferation such that large numbers of specific T cells can be readily produced. The aAPC expands the T cell "specifically" in that only the T cells expressing the particular costimulatory molecule are expanded by the aAPC. Thus, where the T cell to be expanded is present in a mixture of cells, some or most of which do not express the costimulatory molecule, only the T cell of interest will be induced to proliferate and expand in cell number. The T cell can be further purified using a wide variety of cell separation and purification techniques, such as those known in the art and/or described elsewhere herein.

As would be appreciated by the skilled artisan, based upon the disclosure provided herein, the T cell of interest need not be identified or isolated prior to expansion using the aAPC. This is because the aAPC is selective and will only expand the T cell(s) expressing the cognate costimulatory molecule.

Preferably, expansion of certain T cells is achieved by using several aAPCs or a single aAPC, expressing various molecules, including, but not limited to, an antigen, a cytokine, a costimulatory ligand, an antibody ligand that specifically binds with the costimulatory molecule present on the T cell. As disclosed elsewhere herein, the aAPC can comprise a nucleic acid encoding CD32 and/or CD64 such that the CD32 and/or the CD64 expressed on the aAPC surface can be "loaded" with any antibody desired so long as they bind CD32 and/or CD64, which are Fcγ receptors. This makes the "off the shelf" aAPC easily tailored to stimulate any desired T cell.

The invention encompasses a method for specifically inducing proliferation of a T cell expressing a known co-stimulatory molecule. The method comprises contacting a population of T cells comprising at least one T cell expressing the known co-stimulatory molecule with an aAPC comprising a LV encoding a ligand of the co-stimulatory molecule. As disclosed elsewhere herein, where an aAPC expresses at least one co-stimulatory ligand that specifically binds with a co-stimulatory molecule on a T cell, binding of the co-stimulatory molecule with its cognate co-stimulatory ligand induces proliferation of the T cell. Thus, the T cell of interest is induced to proliferate without having to first purify the cell from the population of cells. Also, this method provides a rapid assay for determining whether any cells in the population are expressing a particular costimulatory molecule of interest, since contacting the cells with the aAPC will induce proliferation and detection of the growing cells thereby identifying that a T cell expressing a costimulatory molecule of interest was present in the sample. In this way, any T cell of interest where at least one costimulatory molecule on the surface of the cell is known, can be expanded and isolated.

The invention includes a method for specifically expanding a T cell population subset. More particularly, the method comprises contacting a population of T cells comprising at least one T cell of a subset of interest with an aAPC capable of expanding that T cell, or at least an aAPC expressing at least one costimulatory ligand that specifically binds with a cognate costimulatory molecule on the surface of the T cell. As demonstrated previously elsewhere herein, binding of the co-stimulatory molecule with its binding partner co-stimulatory ligand induces proliferation of the T cell, thereby specifically expanding a T cell population subset. One skilled in the art would understand, based upon the disclosure provided herein, that T cell subsets include T helper ($T_{H1}$ and $T_{H2}$) CD4 expressing, cytotoxic T lymphocyte (CTL) (Tc1 or Tc2) T regulatory ($T_{REG}$), $T_{C/S}$, naïve, memory, central memory, effector memory, and γδT cells. Therefore, cell populations enriched for a particular T cell subset can be readily produced using the method of the invention.

The invention also includes a method for identifying a co-stimulatory ligand, or combination thereof, which specifically induces activation of a T cell subset. Briefly, the method comprises contacting a population of T cells with an aAPC comprising a LV encoding at least one co-stimulatory ligand, and comparing the level of proliferation of the T cell subset contacted with the aAPC with the level of proliferation of an otherwise identical T cell subset not contacted with the aAPC. A greater level of proliferation of the T cell subset contacted with the aAPC compared with the level of proliferation of the otherwise identical T cell subset which was not contacted with the aAPC is an indication that at the co-stimulatory ligand specifically induces activation of the T cell subset to which that T cell belongs.

The method permits the identification of a costimulatory ligand that specifically expands a T cell subset where it is not previously known which factor(s) expand that T cell subset. The skilled artisan would appreciate that in order to minimize the number of screenings, it is preferable to transduce as many nucleic acids encoding costimulatory ligands such that the number of assays can be reduced. Further, the method allows, by combining the various proteins (e.g., stimulatory ligand, costimulatory ligand, antigen, cytokine, and the like), to assess which combination(s) of factors will make the most effective aAPC, or combination of aAPCs, to expand the T cell subset. In this way, the various requirements for growth and activation for each T cell subset can be examined.

In one aspect, the method comprises contacting various aAPCs with the T cell subset without first characterizing the costimulatory molecules on the surface of the T cell subset. Also, the invention encompasses a method where the costimulatory molecule(s) present on the surface of the T cell subset are examined prior to contacting the aAPCs with the cell. Thus, the present invention provides a novel assay for determining the growth requirements for various T cell subsets.

The invention encompasses a method for inducing a T cell response to an antigen in a mammal. The method comprises administering an aAPC that specifically induces proliferation of a T cell specific for the antigen. Once sufficient numbers of antigen-specific T cells are obtained using the aAPC to expand the T cell, the antigen-specific T cells so obtained are administered to the mammal according to the methods disclosed elsewhere herein, thereby inducing a T cell response to the antigen in the mammal. This is because, as demonstrated by the data disclosed herein, that antigen-specific T cells can be readily produced by stimulating resting T cells using the aAPC of the invention.

The invention encompasses a method for inducing a T cell response to an antigen in a mammal in need thereof, the method comprising obtaining a population of cells from the mammal wherein the population comprises T cells, contacting the T cells with an aAPC presenting the antigen in the context of an MHC complex, wherein contacting the T cells with the aAPC induces proliferation of T cells specific for the antigen. The antigen-specific T cells are administered to the mammal, thereby inducing a T cell response to the antigen in the mammal in need thereof. As stated previously elsewhere herein, the data disclosed elsewhere amply demonstrate that antigen-specific CTLs can be readily produced by contacting a T cell with an aAPC wherein the aAPC presents the antigen in the context of an MHC complex. As noted previously elsewhere herein, a wide variety of aAPCs can be used, comprising numerous combinations of various molecules (co-stimulatory ligands, antibodies, antigens, MHCs, and the like), to determine the optimal method for expanding the antigen-specific T cells for administration to a mammal in need thereof.

III. Kits

The invention includes various kits which comprise an aAPC of the invention, a nucleic acid encoding various proteins, an antibody that specifically binds to a costimulatory molecule on the surface of a T cell, and/or a nucleic acid encoding the antibody of the invention, an antigen, or an cytokine, an applicator, and instructional materials which describe use of the kit to perform the methods of the invention. Although exemplary kits are described below, the contents of other useful kits will be apparent to the skilled artisan in light of the present disclosure. Each of these kits is included within the invention.

The invention includes a kit for specifically inducing proliferation of a T cell expressing a known co-stimulatory molecule. This is because contacting the T cell with an aAPC, specifically induces proliferation of the T cell. The kit is used pursuant to the methods disclosed in the invention. Briefly, the kit may be used to administer an aAPC of the invention to a T cell expressing at least one costimulatory molecule. This is because, as more fully disclosed elsewhere herein, the data disclosed herein demonstrate that contacting a T cell with an aAPC comprising a costimulatory ligand that specifically binds with the cognate costimulatory molecule present on the T cell, mediates stimulation and activation of the T cell. Further, the T cells produced using this kit can be administered to an animal to achieve therapeutic results.

The kit further comprises an applicator useful for administering the aAPC to the T cells. The particular applicator included in the kit will depend on, e.g., the method used to administer the aAPC, as well as the T cells expanded by the aAPC, and such applicators are well-known in the art and may include, among other things, a pipette, a syringe, a dropper, and the like. Moreover, the kit comprises an instructional material for the use of the kit. These instructions simply embody the disclosure provided herein.

The kit includes a pharmaceutically-acceptable carrier. The composition is provided in an appropriate amount as set forth elsewhere herein. Further, the route of administration and the frequency of administration are as previously set forth elsewhere herein.

The kit encompasses an aAPC comprising a wide plethora of molecules, such as, but not limited to, those set forth at Tables 1, 2, 3, and 4, elsewhere herein. However, the skilled artisan armed with the teachings provided herein, would readily appreciate that the invention is in no way limited to these, or any other, combination of molecules. Rather, the combinations set forth herein are for illustrative purposes and they in no way limit the combinations encompassed by the present invention. Further, the kit comprises a kit where each molecule to be transduced into the aAPC is provided as an isolated nucleic acid encoding a molecule, a vector comprising a nucleic acid encoding a molecule, and any combination thereof, including where at least two molecules are encoded by a contiguous nucleic acid and/or are encoded by the same vector. The routineer would understand that the invention encompasses a wide plethora of constructs encoding the molecules of interest to be introduced into an aAPC of the invention.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Figure 1:
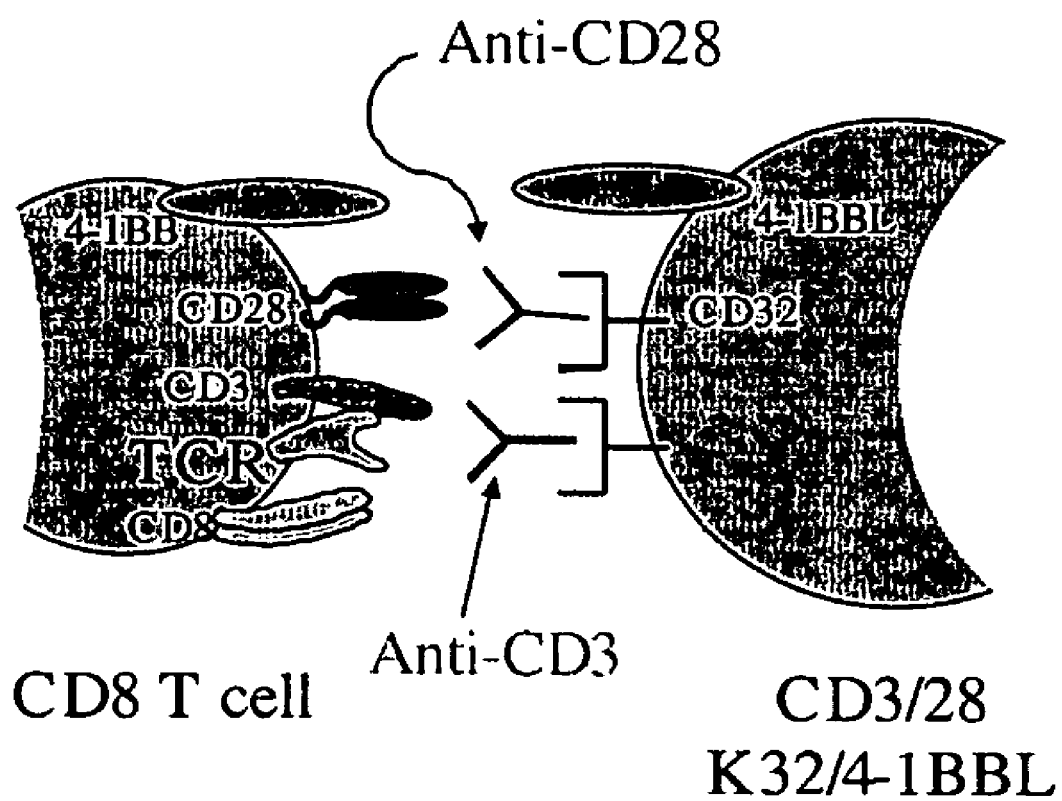
FIG. 1 is a diagram illustrating a model for the construction of a T cell culture system based on artificial antigen-presenting cells (aAPC) using a parental K562 human erythromyeloid cell line.

Development of Cell-Based Artificial Antigen Presenting Cells (aAPC) for Adoptive Immunotherapy It has been demonstrated that the intrinsic growth requirements of CD4 and CD8 T cells differ (Deeths et al., 1997, Eur. J. Immunol. 27:598-608; Laux et al., 2000, Clin. Immunol. 96:187-197; Foulds et al., 2002, J. Immunol. 168:1528-1532). A cell-based aAPC was designed to enable genetic manipulation of the expression of different costimulatory molecules in addition to CD28 for the long term growth of CD8 cells. The culture system was based on the fact that costimulatory signals, in addition to those provided by CD28, are required for optimal CD8 cell growth. The human erythromyeloid CML cell line K562 (Lozzio et al., 1975, Blood 45:321-334) was used as a scaffold for the cellular aAPCs, because this cell line does not express HLA proteins that would promote allogeneic responses. However, K562 do express ICAM (CD54) and LFA-3 (CD58), both of which promote interactions with T cells (FIG. 1). Other advantages of using K562 cell include, but are not limited to, the fact that irradiated K562 cells can be introduced in the clinical setting as these cells are mycoplasma-free, propagate in serum-free medium, and are easily killed by natural killer (NK) cells. Despite the desirability of using K562 to produce such aAPCs, K562 cells have been notoriously difficult to transduce (Kahl et al., 2004, J. Virol. 78:1421). Surprisingly, the data disclosed herein demonstrate, for the first time, that K562 cells can be transduced, either serially and/or in parallel, with a wide plethora of exogenous nucleic acids to express a number of molecules thereby obtaining a library of aAPCs with desired phenotypes. Such LV-based transduction is performed serially and/or in parallel, and MoFlo is used to clone cells demonstrating a desired phenotype. Further, the data demonstrate that an optimal promoter can be selected and promoter competition can be assessed and eliminated if necessary or desired. The library of aAPCs produced using the methods of the invention are then assessed for biologic function in vivo, using an art-recognized model, such as, but not limited to, a NOD/SCID mouse model.

With regard to use of K562 to produce aAPCs, the disclosures of U.S. patent application Ser. No. 10/336,135 (now published as U.S. Patent Application Publication No. US2003/0147869A1) and International Patent Application No. PCT/US03/00339 (now published as International Publication No. WO 03/057171A2) are incorporated by reference as if set forth in their entirety herein.

Production of Lentiviral Vectors

To circumvent the limitations of previously described transfection-based approaches to introduce genes into K562 cells, a series of high-titer lentiviral vectors were used, as disclosed elsewhere herein, to stably introduce a wide array of costimulatory ligands and MHC molecules into K562 cells. This allows for the systematic and rapid production for a variety of aAPCs and allows for the determination for the combination of costimulatory molecules that yields the optimal expansion and effector functions to HIV-specific T cells. The data disclosed herein demonstrate this approach.

As a non-limiting example, an aAPC of the present invention can comprise some or all of the ligands, among other things, described herein. These various constructs are used to transduce the K562 cells using LVs. These are merely exemplary and the invention is not limited to these constructs, or any other particular construct, for transduction of the aAPCs of the invention with a known molecule of interest to be expressed in the cells.

CD32: A CD32-comprising LV-transduced aAPC was produced using CD32 (SEQ ID NO:8) amplified from cDNA prepared from neutrophil RNA. Briefly, the neutrophils were isolated by Ficoll gradient from an apheresis product obtained from a normal, anonymous donor. This PCR product was cloned into pcDNA3.1 via Kpn I and Not I restriction sites that were added to the ends of each amplifying primer. This vector was digested with XbaI and Sal I and cloned into pCLPS (Parry et al., 2003, J. Immunol. 171:166-174) to create pCLPS CD32. Supernatant containing high titer lentiviral vector was obtained by harvesting transfected 293T cells that had been transfected using a split genome transfection method as described in Dull et al. (1998, J. Virol. 72:8463-8471) and Parry et al. (2003, J. Immunol. 171:166-174).

IL-7: In one embodiment, an aAPC comprising IL7 was produced using IL-7 nucleic acid (SEQ ID NO:9) amplified from cDNA and cloned into pcDNA3.1 hygromycin. SOE by PCR (consisting of three separate reactions) using primers designed with 5' CD32 XbaI and 3' IL-7 SalI was performed. Additional templates used during reaction included CD32-pCDNA3.1 and pCLPS m8h28-IRES-YFP followed by restriction enzyme digestion of the PCR products to produce CD32-IRES-IL-7 pCLPS. Lentivirus was made as described previously elsewhere herein.

IL-15: In another embodiment, plasmid pVAX Hum IL-15 (comprising SEQ ID NO:10), which comprises an IgE leader peptide attached to mature IL-15 sequence, was used. PCR primers were designed to add MluI and SalI restriction sites to the plasmid sequence. The PCR product was digested with the respective enzymes and was cloned into CD32-IRES-IL-7 pCLPS (which was also cut with MluI and SalI to remove the IL-7 gene). Lentivirus was prepared as described herein.

IL-21: In another embodiment, IL-21 (SEQ ID NO:11) was amplified from activated human PBMC and cloned into TOPO 3 vector (Invitrogen, Carlsbad, Calif.). Using BamHI and XhoI, the human IL-21 gene was excised from the vector and the insert was then cloned into the first position of NKG2D-IRES-DAP12 pCLPS construct (which was produced using BamHI and XhoI). Human CD32 was amplified from CD32-pCLPS (as described above) using PCR primers that flanked the ends comprising MluI and SalI sites. The PCR product was digested with the respective enzymes and was cloned into the second position to create IL21-IRES-CD32 pCLPS. Lentivirus was produced as described previously elsewhere herein.

OX40L: In another embodiment, OX40L (SEQ ID NO:12) was amplified from cDNA obtained from mature dendritic cells (Schlienger et al., 2000, Blood) and was cloned into pCDNA3.1 hygromycin. Restriction enzyme sites MluI and SalI were added to the ends of PCR primers and the PCR product was digested with the respective enzymes and was cloned into CD32-IRES-IL-7 pCLPS, which was also cut with MluI and SalI to remove IL-7 insert. CD32-IRES-OX40L pCLPS lentiviral vector was made as described previously elsewhere herein.

4-1BBL: In another embodiment, 4-1BBL (SEQ ID NO:13) was amplified from cDNA obtained from activated B cells which were purified by negative selection as described previously, and which cells were activated with PMA and ionomycin. The PCR product in which Kpn I and NotI sites were introduced at the ends, was cloned into KpnI/Not I digested pcDNA 3.1 hygromycin. The vector was digested with XbaI and Sal I and was cloned into XbaI/Sal I digested pCLPS lentiviral vector. pCLPS 4-1BBL lentiviral vector was made as described previously elsewhere herein.

CD80: In yet another embodiment, CD80 (SEQ ID NO:14) was amplified from cDNA obtained from immortalized B cell line (Vonderheide et al., 1999, Immunity 10:673-679) using PCR primers that introduced BamHI and SalI sites at the ends of the PCR product. Following digestion with these enzymes, CD80 was cloned into BamHI/SalI digested pCLPS lentiviral vector. CD80-pCLPS lentiviral vector was produced as described previously elsewhere herein.

CD83: In yet a further embodiment, CD83 (SEQ ID NO:15) was amplified from cDNA prepared from the Ramesh cell line, using primers to introduce XbaI and XhoI restriction sites to the ends of the PCR product. Following digestion with these enzymes, CD83 PCR product was ligated into pCLPS (digested with XbaI/SalI). CD83-pCLPS lentiviral vector was produced as described previously elsewhere herein.

CD86: In another embodiment, CD86 (SEQ ID NO:16) was amplified from cDNA obtained from mature dendritic cells (which were prepared as described in Schlienger et al., 2000, Blood) using PCR primers that had BamHI and Not I restriction sites added to the ends. The PCR product was digested with BamHI and Not I and ligated into similarly digested pcDNA3.1 hygromycin. This vector was digested with BamHI and Sal I and was cloned into pCLPS. pCLPS CD86 lentiviral vector was produced as described previously elsewhere herein.

ICOS-L: In another embodiment, ICOS-L (SEQ ID NO:17) was amplified using PCR primers comprising Kpn I and Not I restriction sites at the ends, using cDNA obtained from dendritic cells. The PCR product was cloned into KpnI and Not I digested pcDNA3.1 hygromycin. The plasmid was digested with BamHI and Xho I to excise the ICOS-L insert which was cloned into pCLPS (digested with BamHI/XhoI) to generate ICOS-L-pCLPS. Lentiviral vector was produced as described previously elsewhere herein.

HLA-A*0201: In yet another embodiment, HLA-A*0201 cDNA clone was obtained from The International Cell and Gene Bank, which is publicly available from the website of the International Histocompatibility Working Group organization (ihwg.org) at the cell and genebank shared resources (cbankover). HLA-A*0201 was amplified by PCR using primers comprising Bam HI and Sal restriction sites at the ends and the amplification product was cloned into pCLPS. pCLPS HLA-A2 lentiviral vector was produced as described previously elsewhere herein.

Flu-GFP: In one embodiment, a Flu-GFP fusion vector comprising the entire enhanced Green Fluorescent Protein (BD Biosciences, Palo Alto, Calif.) coding region fused to the Flu Matrix Protein 1 nucleotides 113-290 (SEQ ID NO:18) was used. This construct was digested with BamHI and Xho I and cloned into Bam HI and Sal I digested pCLPS. pCLPS GFP-flu lentiviral vector was produced as described previously elsewhere herein.

DRα: In another embodiment, DRα (SEQ ID NO:19) and DRB4 (SEQ ID NO:20) were cloned using cDNA obtained from CD3/28-activated CD4 T cells using standard techniques, and each nucleic acid was cloned into pCLPS. To produce K562 cells that expressed DR4, both vectors were simultaneously transduced into K562 and HLA-DR cells and cells expressing DR4 were isolated using flow cytometry as described elsewhere herein.

In addition, ILT3 (SEQ ID NO:21) and ILT4 (SEQ ID NO:22) were expressed in the aAPC of the present invention essentially according to methods disclosed elsewhere herein and known in the art.

High-titer, high efficiency, third-generation lentiviral vectors (LV) were used to efficiently produce aAPC. These vectors have a number of built-in safety features that make them ideally suited for human therapeutics. Specifically, approximately 90% of the HIV-1 sequences have been removed from the transfer vector leaving only the packaging and integration sequences physically linked to the payload gene. Replication-incompetent packaged LVs are generated using a split genome approach. Specifically, 293 T cells are transfected with four separate plasmids encoding HIV gag/pol, VSV G protein (env), HIV rev, and the transfer vector. Lentiviral vectors were produced after transfection of 293T HEK cells cultured in RPMI 1640 (BioWhittaker, Inc. Rockville Md.), 10% FCS, 2 mM glutamine and 100 IU/mL penicillin, 100 ug/mL streptomycin. Cells were seeded at $5 \times 10^6$ per T 150 tissue culture flask 24 hours prior to transfection. All plasmid DNA was double purified using a CsCl gradient. Cells were transfected with 7 μg pMDG.1 (VSV-G envelope), 18 μg pRSV.rev (HIV-1 Rev encoding plasmid), 18 μg pMDLg/p.RRE (packaging plasmid) and 15 μg pCLS transfer plasmid using Fugene 6 (Roche Molecular Biochemicals, Indianapolis, Ind.). Media was changed 6 hours after transfection and the viral supernatant was harvested at 24 hours and 48 hours post-transfection. Viral particles were concentrated 10-fold by ultra centrifugation for 3 hours at 28,000 RPM with a Beckmann SW28 rotor as described in Reiser (2000, Gene Ther. 7:910-913).

As a result of this strategy, three independent and highly unlikely recombination events would have to occur to create a replication-competent vector. As an additional safety precaution, this vector was rendered self-inactivating by deleting the 3'LTR promoter (Zufferey et al., 1998, J. Virol. 72:9873-9880). Thus, upon integration the only functioning promoter is the supplied internal promoter (in this case CMV) juxtaposed with the payload gene and thus, no HIV sequences are transcribed.

Using this lentiviral vector transduction approach, several high titer lentiviral vectors have been created for CD83 and ICOS-L and KA2/32/86/4-1BBL aAPCs and the parent KA2/32/86 has been created (FIG. 3), as well as other aAPCs described elsewhere herein. Briefly, K562 cells were transduced with lentiviral expression vectors encoding CD32, HLA-A2, 4-1BBL and an influenza MP1GFP fusion protein, sorted for single clones expressing all four markers, and expanded for four weeks (FIG. 3). In addition, a wide variety of lentiviral vectors, comprising numerous combinations of molecules useful for transduction of K562-based aAPCs, have been produced (P) or have been designed (D), as set forth in Table 1.

TABLE 1

| | |
|---|---|
| pCLPS CD32 (P) | pCLPS siRNA-PD-L1 (D) |
| pCLPS CD32/IRES/GM-GCSF (D) | pCLPS siRNA-B7-H3 (D) |

TABLE 1-continued

| | |
|---|---|
| pCLPS CD32/IRES/IL-7 (P) | pCLPS siRNA-TGFbeta (D) |
| pCLPS CD32/IRES/IL-12 (D) | pCLPS IDO (D) |
| pCLPS CD32/IRES/IL-15 (P) | pCLPS GFP-flu matrix (P) |
| pCLPS CD32/IRES/IL-18 (D) | pCLPS GFP/IRES/pol (P) |
| pCLPS CD32/IRES/IL-21 (P) | pCLPS HLA DR0101 (D) |
| pCLPS CD32/IRES/Interferon alpha (D) | pCLPS HLA A201 (P) |
| pCLPS CD32/SLC (D) | pCLPS ICOSL (P) |
| pCLPS CD30L (D) | pCLPS CD86 (P) |
| pCLPS OX40L (P) | pCLPS CD83 (P) |
| pCLPS 4-1BBL (P) | pCLPS CD80 (P) |
| pCLPS GITRL (D) | pCLPS CD70 (D) |
| pCLPS CD40 (D) | |

K562 Cells

K562 cells were isolated from a patient with chronic myelogenous leukemia in terminal blast crisis (Lozzio et al., 1975, Blood 45:321-334). K562 may represent a DC precursor that does not express MHC molecules or T cell costimulatory ligands, but retains many other attributes that make DCs effective APCs, such as, but not limited to, cytokine production, adhesion molecule expression, and macropinocytosis. These attributes may be unique to K562 cells, as the monocytic cell line U-937 was unable to function as an effective aAPC. Thus, K562 cells represent ideal scaffolds onto which the desired MHC molecules and costimulatory ligands can be introduced to establish a DC-like aAPC. Such an aAPC has all the advantages of DCs, including high levels of MHC expression, a wide array of costimulatory ligands, and the ability to engage in cytokine crosstalk with a T cell. K562-based aAPCs also lack the disadvantages of DCs, such as their limited life span, lack of replicative capacity, and ill defined maturation requirements (Lee et al., 2002, Vaccine 20:A8-A22).

Transduction of K562 Cells to Produce aAPCs

The data disclosed herein demonstrate the creation of a K562 aAPC via lentivirus-mediated introduction of costimulatory ligands that enable K562 cells to better mimic the potent T cell stimulatory ability of DCs.

K562 cells were transfected with the human Fc receptor CD32 ("K32 cell") to permit loading with anti-CD3 and anti-CD28 antibodies, and the cell was also transfected with human 4-1BBL ("K32/4-1BBL cells") for added co-stimulation (FIG. 1). KA2/32/86/4-1BBL/CD83 aAPCs were produced with a CD83 lentiviral vector by spinoculation (O'Doherty et al., 2000, J. Virol. 74:10074-10080) to transduce the KA2/32/86/4-1BBL parent. Approximately 5 million KA2/32/86/4-1BBL cells were mixed with 500 μl of concentrated virus ($5\times10^7$-$5\times10^8$ IFU/ml) and spun at 1200 g for 2 hours. Five days post transduction the cells were stained with a CD83 specific Ab and a Moflo sorter was used to isolate high expressing clones. 15-20 days post sorting, colonies of single clones were visible and these colonies of single clones were screened by CD83 expression. High expressors were expanded further and the expression levels of the other introduced markers (HLA-A2, 4-1BBL, CD86 and CD32) was measured to ensure that the descendants are similar to parent cell line in all but CD83 expression. The K32/86/4-1BBL/ICOS-L and K32/86/4-1BBL/ICOS-L/CD83 aAPCs were created in this manner using the appropriate viruses.

Using the methods described herein, stable expression of of at least nine (9) genes has been accomplished in a K562 aAPC. The following genes were transduced into a K562 cell and were stably expressed, as detected using flow cytometry: Flu-GFP (FIG. 8A); CD80 (FIG. 8B); CD86 (FIG. 8C); 4-1BBL (FIG. 8D); and HLA ABC (FIG. 8E). The KT32/A2/4-1BBL/40L/CD80/CD83/CD86 also stably expressed detectable levels of CD32, CD83, CD40L, and ICOS-L. These expression levels remained constant for greater than 3 months of continuous culture without any selection. In addition, the production of several aAPCs is illustrated in FIG. 3. These aAPCs comprise expression of all of the transgenes driven by the CMV promoter. Although diminishing expression levels of transgenes due to sequestration of CMV-specific transcription factors could occur, (Cahill et al., 1994, FEBS Lett. 344:105-108; Kang et al., 1992, Science 256:1452-1456) to date no evidence of any problems with serially transducing K562 cells with five different lentiviral vectors has been detected (FIG. 3).

Using the methods described above for transducing a K562 cell, parental K562cc was compared to LV-transduced K562 cells (e.g., transduced with and expressing five and eight genes). As illustrated in FIGS. 7 and 8, LV transduced cells exhibit favorable growth kinetics compared with otherwise identical, but non-transduced, parental cells.

In addition to the expression of costimulatory ligands, the aAPCs of the invention can be used to produce various cytokines, as exemplified by the production of IL-7 and IL-15 by K562 cells transduced with CD32/IRES/IL-7 and CD32/IRES/IL-15 vectors. The cells were sorted for high CD32 expression and production of the respective interleukin was assessed (FIG. 13), demonstrating that the appropriate cytokine was produced.

Further, using the methods for transducing a K562 cell described above, aAPCs express CD32 from an LV at a greater level than the expression of CD32 in an otherwise identical K562 cell transfected using a plasmid vector (FIG. 11). These data demonstrate that, surprisingly, K562 were easily transduced using lentiviral vectors. FIG. 11D is a graph depicting that expression of CD32 using a LV to transduce K562 cells is greater than the level of CD32 expression in an otherwise identical K562 cell transfected using a plasmid vector. Moreover, the data disclosed herein demonstrate that the level of CD32 expression was maintained for greater than nine months. Moreover, this level of CD32 expression was maintained for greater than nine months. The characterization of aAPC cells expressing CD64 is described below.

In addition, the data disclosed herein demonstrate that the aAPCs grow in culture in medium free of fetal calf serum (FCS), an important consideration for production of aAPCs for use in treatment of human patients (see FIG. 7). These data demonstrate that the novel aAPCs of the invention grow in defined medium (Aim V) comprising 3% AB serum. That is, various K562-based aAPCs were produced by transducing parental K562 (k562cc) using lentivirus vectors ("LV"): KT32 (1 gene); KT32/4-1BBL/CD86 (3 genes); KT32/4-1BBL/CD86/A2/Flu-GFP (5 genes). In addition, as illustrated in FIG. 7, introduction of a lentiviral vector does not significantly alter the growth rates of the K562 cells. These data demonstrate that master cell banks can be produced using LV-transduced K562 aAPCs and that aAPCs grow as well as the parental cells.

The present data has demonstrated the methods for transducing K562 cells and the expression and growth properties of these aAPCs. In addition, the long-term stability and sufficient expression of a cytokine/costimulatory molecule transduced into a K562-based aAPC has been evaluated. CD32 has been stably expressed in a transduced K562 cell for longer than nine months. Further, detectable and stable expression of at least eight exogenous molecules introduced into a K562-based aAPC has also been achieved (KT32-A2-41BBL-40L-80-83-86), and there is no data to suggest that additional molecules will not be similarly expressed. Indeed, an aAPC has been produced expressed nine genes (including ICOS-L) for greater than 60 days at this time. Thus, at present, the ability of the aAPCs of the invention to express a variety of molecules in a single aAPC is not limited. Further, the aAPCs of the invention are negative for mycoplasma and replication competent lentivirus (RCL), and their safety and lack of any contaminating pathogens can be readily assessed.

The present invention comprises numerous K562-based aAPCs produced, according to the methods set forth herein, including, but not limited to those set forth in Table 2. These aAPCs, comprising combinations of various immunostimulatory molecules, can be used for both ex vivo and in vivo methods comprising expansion of certain T cell subsets, identification of combinations of factors that expand T cell subsets, as well as cell based and gene therapy where the aAPCs, and or T cells expanded thereby, are administered to a patient in need thereof. Of course, the present invention is not limited to these, or any particular aAPCs, and the list set out in Table 2 is merely illustrative of the teachings provided herein.

tory sequences. Further, a nucleic acid encoding the tumor cell antigen can be transduced into the cell or the antigen can be otherwise loaded into the cell such that the cell processes and presents the appropriate epitope in the context of an MHC protein. This is because it has been demonstrated elsewhere herein that K562 cells have the ability to process and present antigens without the need to first identify or isolate the specific antigen or epitope required. Thus, a cell extract (comprising at least one membrane component of a tumor cell) can be loaded into the K562-based aAPC and the natural ability of the cell to process and present the relevant antigen is exploited. While customized aAPCs are set forth herein, these are for illustrative purposes only, and the invention is not limited to these embodiments set forth in Table 3. This is because, as would be appreciated by the skilled artisan armed with the teachings provided elsewhere herein, a wide plethora of molecules can be transduced and expressed by the aAPCs in virtually limitless combinations.

TABLE 3

| Indication | Epithelial (breast/colon/lung/ovary/prostate) | Heme Malignancy (CML/AML/Lymphoma/ALL) | Skin (Melanoma/Merkel) | Autoimmune/Transplantation (RS/SLE/GVHD/Organ Txp) |
|---|---|---|---|---|
| aAPC | KT-BCLOP | KT-CALA | KT-MM | KT-T$_{REG}$ |
| costim | CD80/83/41BBL/OX40L | CD80/83/41BBL/OX40L | CD80/83/41BBL/OX40L | CD86 dim/B7H-3/MHCII |
| antigens | gp100/MAGE | To be determined | | To be selected |
| cytokines | GM-CSF/IL-15/SLC | GM-CSF/IL-15/SLC | GM-CSF/IL-15/SLC | TGFbeta/IL-10 |

TABLE 2

| Polyclonal T cell expanding aAPCs (designated "KT32" series) | Antigen-specific T cell expansion aAPCs (designated "KTA2" series) |
|---|---|
| KT32 | KTA2 |
| KT32/4-1BBL | KTA2/86 |
| KT86 | ktA2-86-ICOSL |
| KT83 | ktA2-41BBL |
| KT80 | ktA2-41BBL-FLU-GFP |
| KT86-80 | ktA2-41BBL-86-FLU-GFP |
| KT83-80 | ktA2-32-41BBL-FLU-GFP |
| KT32/86/83 | ktA2-86-FLU-GFP-CD40L |
| kt32-ICOSL | ktA2-41BBL-86-FLU-GFP-83 |
| kt86-ICOSL | ktA2-41BBL-86-FLU-GFP-CD40L |
| kt32-41BBL-80 | ktA2-86-FLU-GFP-CD40L |
| kt32-41BBL-86 (hi, lo) | *ktA2-41BBL-86-83-40L-Flu-GFP |
| kt32-41BBL-83 | |
| kt32-IL7 | |
| kt32-IL15 | |
| ktIL-21 | |
| kt32-41BBL-86-83 | |
| kt32-41BBL-86-83-IL15 | |
| kt32-CD30L | |
| kt32-OX40L | |
| kt32-HLA-DR (MHC class II) | |

Example 2

In Vivo Therapeutic Use of aAPCs

The invention includes LV-engineered K562 aAPC for in vivo therapeutic vaccination and for the ex vivo expansion of T cells for therapeutic uses. The antigens, cytokines, and/or costimulatory molecules can be transduced into a K562 cell under the control of the same or separate promoters/regula- Example 3

Ex Vivo Therapeutic Uses of aAPCs

Other aAPCs can be prepared for ex vivo use, such as, but not limited to, adoptive immunotherapy and gene therapy. Among the customized versions of aAPC for such ex vivo uses are, inter alia, the constructs disclosed in Table 4 below. That is, T cells isolated from a subject can be stimulated and expanded in vitro using these, or a wide plethora of other, aAPCs then the T cells can be introduced into the subject thereby providing adoptive immunotherapy thereto. Additionally, the expanded T cells can be genetically engineered to express an exogenous protein that was not expressed, or was expressed at a lower level, compared with expression of the protein in the T cell prior to, or in the absence of, the genetic engineering. Thus, the present invention provides both ex vivo cell based adoptive immunotherapy and gene therapy using the aAPCs of the invention to expand T cells used for autologous transplantation of a subject in need thereof. Table 4 merely sets forth several illustrative examples of aAPCs that can be used for such cell/gene therapy, but the invention is not limited to these exemplary "off the shelf" aAPCs of the invention.

TABLE 4

| Indication | CTLs (melanoma, HIV, RCC) | Genetically engineered T cells (HIV/cancer) |
|---|---|---|
| AAPC Costim | KT-A2 CD80/83/83/4-1BBL | KT32 Anti-CD3, 28/4-1BBL/83) |

TABLE 4-continued

| Indication | CTLs (melanoma, HIV, RCC) | Genetically engineered T cells (HIV/cancer) |
|---|---|---|
| Antigens cytokines | Of choice IL-7/IL-15/SLC | None IL-7, IL-15 |

Example 4

Stimulation of Human CD 4 T Cells with aAPCs

The data disclosed herein demonstrate that long-term growth of CD4 T cells was obtained using K32/CD3/28 and K32/86CD3 aAPCs in the absence of exogenous cytokines, but U937-based aAPCs were not effective (FIG. 5). Moreover, the data demonstrate that K562-based aAPCs (e.g., K32/CD3/28, K32/86/CD3) mediate long-term growth of CD4 T cells more effectively bead-based aAPCs (CD3/28 coated beads) where both beads and cells are loaded with CD3 and CD28. These results demonstrate that detectable "cross-talk" occurs between the K562-based aAPCs and T cells which is not possible using bead-based systems. As illustrated in FIG. 5, not all tumor cell lines have the capacity to serve as artificial APCs and the data further demonstrate the ability of K562 cells to serve as potent APCs, which was unexpected. These surprising results support the significant improvement over prior art methods that is possible using K562-based aAPCs.

The data disclosed herein further demonstrate the usefulness of K562-based aAPCs for inducing cytokine and/or costimulatory molecule expression by CD4 T cells (FIGS. 6A-6D). These data all demonstrate that K562-based aAPCs are far superior than U937-based aAPCs in inducing cytokine and costimulatory (costim) gene expression by T cells and that some aAPC constructs are better than others, somewhat depending on the cytokine and/or costimulatory molecule being expressed. More specifically, while K32/CD3/28 was generally superior compared with the other aAPCs, expression of B7-H3 was actually greater by K32/CD3 in the presence of CD4 when compared with K32/CD3/28 under similar conditions. These data demonstrate that K562 aAPCs upon interacting with T cells, produce a series of additional cytokines and costimulatory molecules (APC and T cell cross talk) that can further enhance T cell activation and expansion. More specifically, various K562- and U937-based aAPCs transduced with various vectors encoding certain molecules (e.g., K32/CD3/28, K32/CD3, K32, U32/CD3/28, U32/CD3, U32) were assayed for their ability to induce expression of molecules of interest (e.g., IL-15, PD-L1, PD-L2, and B7-H3). The data disclosed herein demonstrate that K562-based aAPCs induced detectable expression of these molecules and did so to far greater extent than U937-based cells. These data further demonstrate the usefulness of the of novel aAPCs of the invention, and the significant improvement over prior art methods since these data all demonstrate that K562-based aAPCs are far superior than U937-based aAPCs in inducing cytokine and costimulatory (costim) gene expression by T cells. These results are particularly remarkable given the previous teachings demonstrating that K562 parental cell line demonstrates poor T cell stimulatory activity (Britten et al., 2002, J. Immunol. Methods 259:95-110).

Given the superior results of aAPCs of the present invention in comparison to parental K562 cells, U-937 based aAPCs and beads, the relative abilities of the various aAPCs disclosed herein was evaluated. Some aAPC constructs are better than others at mediating an effect upon certain T cells, and that the effectiveness varies somewhat depending on the cytokine and/or costimulatory molecule, or combinations thereof, being expressed. More specifically, while K32/CD3/28 was generally superior compared with the other aAPCs, expression of B7-H3 was actually greater by K32/CD3 in the presence of CD4 when compared with K32/CD3/28 under similar conditions. These data further demonstrate that certain combinations of molecules expressed in the novel K562-based aAPCs have a greater effect on certain populations of T cells. These data therefore provide a novel system for assessing the effectiveness of various combinations of molecules to achieve desired effect(s) and/or to stimulate and expand T cell subsets of interest none of which were possible prior to the present invention.

Example 5

Stimulation of Human CD8 T Cells with aAPCs

Briefly, 50,000 irradiated KT32/4-1BBL/CD86 were coated with anti-CD3 Ab and were mixed with 100,000 freshly isolated CD8 T cells from a healthy donor. Every 10-12 days the CD8 T cells were re-stimulated with freshly irradiated KT32/4-1BBL/CD86 aAPCs. The total number of cells that would have accumulated if no cells have been discarded is depicted as a semi-log plot of total cell number versus days in culture (FIG. 9). As also illustrated in FIG. 9, polyclonal CD8 T cells expanded by aAPCs transduced with CD32 and 4-1BBL (K32/4-1BBL) expanded 18,600 fold after 43 days.

The data disclosed herein further demonstrate the expansion of antigen specific CD8 $T_{CM}$ using an aAPC (e.g., K32/K-41BBL aAPC). Briefly, both flu tet+ and flu tet– T cells were expanded (FIGS. 10A-10C) as a function of days in culture wherein interleukin 2 (IL-2) was added to the culture medium on day 20. The data demonstrate a shift by day 16 in cells stained for CD8 expression using flow cytometry where the cells were sorted as being Flu tet– or Flu-tet+, demonstrating antigen specific proliferation of CD8 $T_{CM}$ cells cultured with K32/4-1BBL aAPC. At day 26, the cells were assayed for their ability to specifically lyse tet+ or tet– cells that were T2-null or expressed T2-flu. The data demonstrate that cell killing was specific for ter+, T2-flu target cells as demonstrated by a chromium release assay (FIG. 10E). The percent specific lysis was a function of the effector:target (E:T) cell ratio, with maximum specific cell lysis detected at a 10:1 ratio, and decreasing thereafter as the E:T ration was decreased to 1:1. At all E:T ratios examined, cell lysis specific for tet+, T2-flu was observed using the cells expanded using the aAPC.

To determine if the aAPCs of the present invention can act in an antigen/MHC-specific manner, K562 cells were transduced with HLA-A2, CD86, 4-1BBL, CD32, CD64 and influenza MP1 mini gene that encodes the A2 restricted epitope GILGFVFTL (SEQ ID NO:1) linked to GFP. FACS analysis of this KA2/32/86/4-1BBL/Flu GFP aAPC demonstrated that all five markers are expressed at high levels (FIGS. 3 and 12), and stable expression of all the transgenes was observed for as long as nine months of continuous culture.

To demonstrate that these aAPCs were sufficient to expand antigen specific cells, 1500 flu tetramer positive cells were isolated from a HLA-A2 donor and were mixed with 3000 irradiated KA2/32/86/4-1BBL/Flu GFP aAPCs. Every 10 days freshly irradiated KA2/32/86/4-1BBL Flu GFP aAPCs are added to the culture so that there would be approximately 1 aAPC for every two T cells. After 22 days, there were approximately 10 million CD8 T cells. These cells were stained with a Flu specific A2 tetramer and greater than 90% of the cells were Flu specific (FIG. 12F), which was approximately 250-fold enrichment compared with the pre-sort cells (FIG. 12E). These data demonstrate that K562 cells have the ability to process and present antigen and expand antigen specific T cells without the use of an antibody. Importantly, KA2/32/86/4-1BBL/Flu GFP aAPCs were unable to expand T cells from the tetramer negative fraction of cells.

A similar experimental protocol was used to expand flu specific T cells, but anti-CD3 was used to deliver signal "one" rather than a peptide bound by MHC class I (FIG. 2). Briefly, the cells were stained with A*0201 tetrameric MHC loaded influenza matrix protein peptide amino acid sequence (GILGFVTVL; SEQ ID NO:1), and sorted into positive and negative fractions. After 17 days of expansion using K32/4-1BBL/CD3/28 aAPC, each population of cells was stained with the same tetramer used for the initial sorting. Only about 60% of the cells were flu tetramer positive and the overall level of staining was lower. This suggests that the KA2/32/86/4-1BBL/Flu GFP aAPCs selectively expand a T-cell receptor (TCR) that has the highest affinity for the GILGFVFTL (SEQ ID NO:1) peptide presented by the HLA-A2.

Figure 2A:
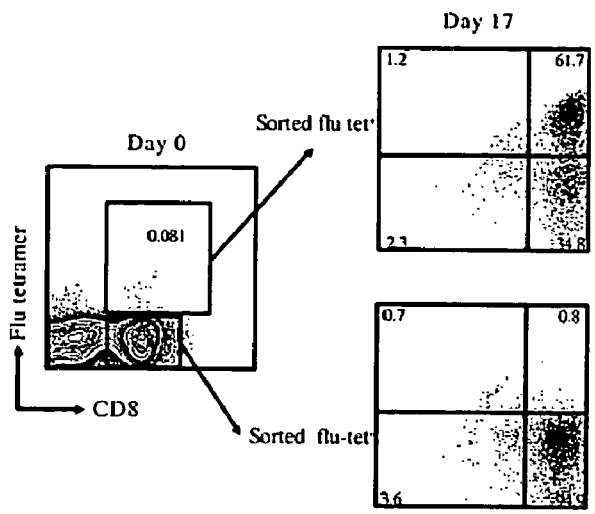
FIGS. 2A through 2C, depicts the expansion of tetramer sorted influenza virus (flu) specific central memory T cells using K32/4-1BBL/CD3/28 aAPC.
Figure 2B:
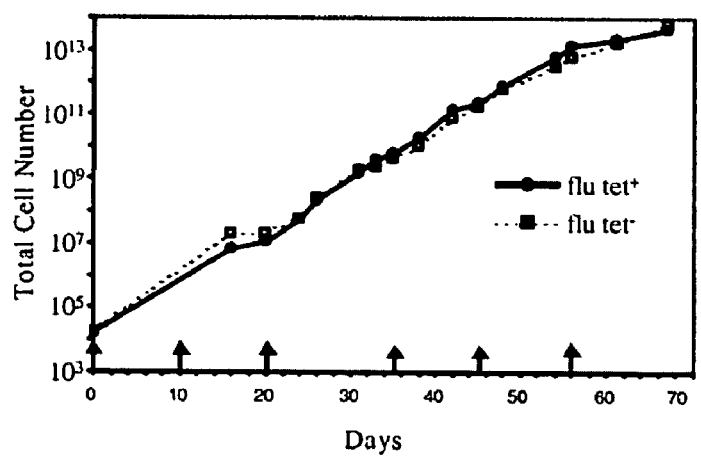
Figure 2C:
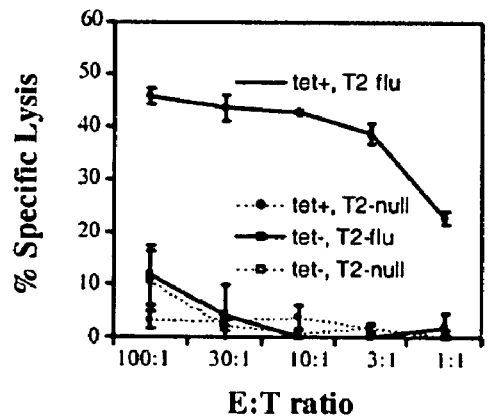

To determine whether the K32/4-1BBL aAPC coated with anti-CD3 and CD28 Abs could be used to expand antigen-specific CD8 T cells, a population of MHC tetramer-sorted primary CD8$^+$ T cells were cultured with K32/4-1BBL/CD3/28 aAPCs for 10 weeks (FIG. 2A). T cells from A*0201 individuals with immunity to influenza were stained with anti-CD8 mAb and an A*0201 MHC tetramer complexed to an A*0201-restricted peptide epitope of the influenza matrix protein (flu MP tetramer). The low-frequency (less than about 0.1%) tetramer$^+$ population was sorted and stimulated with irradiated K32/4-1BBL aAPCs coated with anti-CD3 and CD28 Abs. All cells were re-stimulated with K32/4-1BBL aAPCs at about 10 day intervals. No specific flu stimulation was provided during culture. Exponential growth curves were obtained for several months of culture. In a representative experiment, approximately 8,000 antigen-specific T cells yielded $1.5 \times 10^9$ cells after one month of culture (FIG. 2B), which is a number sufficient for effective immunotherapy (Riddell et al., 1995, Annu. Rev. Immunol. 13:545-586). Phenotypic analysis of cultures demonstrated that the irradiated aAPCs mixed with resting human T cells yielded a population of pure T cells within one week. Furthermore, flu MP tetramer positive cells displayed potent cytotoxicity for Flu-MP peptide pulsed T2 targets (FIG. 2C). This strategy can be adapted to expand HIV-specific CD8 T cells and to use these aAPCs to expand CD8 T cells with a broad specificity.

The K32/4-1BBL aAPC was also used to expand hTERT specific cytotoxic lymphocytes (CTL). hTERT-specific CTLs expanded using a K32/4-1BBL aAPC specifically lysed carcinoma cells expressing HLA-A2 and telomerase$^+$ (OV-7) but not carcinoma cells that are telomerase$^+$ and HLA-A2$^-$ (SK-OV-3) (FIG. 10E). Thus, the aAPC induced expansion of antigen specific CTLs that require the antigen to be recognized in the context of HLA-A2. Further, during expansion, the CTLs, which were obtained from a breast cancer patient vaccinated with hTERT, demonstrated a detectable increase, as assessed using MoFlo sorting, in the percentage of tet+ CD8 CTLs during expansion by K32/4-1BBL aAPC. The timing of the MoFlo sorting corresponding to each FIG. 10A-10C is indicated on the graph showing population doublings as indicated by an arrow (FIG. 10D).

Surprisingly, the data disclosed herein demonstrate, for the first time, that K562-based aAPC have the ability to process an antigen which is then presented to T cells thereby expanding antigen-specific T cells where the particular epitope responsible for expansion is not known a priori. More specifically, purified T cells were obtained from an HLA A*0201 donor and the cells were stained with anti-CD8 mAb and an A*0201 MHC tetramer complexed with an A*0201 restricted epitope of the influenza matrix protein (flu-MP-tetramer). The tetramer positive population of approximately 1,500 cells, was sorted and stimulated using irradiated KTA2/CD32/4-1BBL/FLU-GFP aAPCs loaded with anti-CD28 antibody. The cells were re-stimulated with KTA2/CD32/4-1BBL/FLU-GFP aAPCs at approximately every 10-12 days. Interleukin-2 was added to the culture at every feeding, approximately every 2-3 days.

After twenty-six days of culture, most of the T cells were flu-MP tetramer positive compared with the initial pre-sort population, demonstrating that the aAPC processed and presented the flu-specific antigen and efficiently expanded flu-specific CTLs (FIGS. 12A-12F). These results demonstrate that the aAPCs of the invention can be used to expand and produce antigen-specific T cells even where the precise epitope of the antigen required to produce the cells is not known. This is important to the development of transfer therapy where the precise antigen that stimulates a T cell is not known. This is the case for, among other things, tumor specific antigens, where very few are known. Thus, the present invention relates to providing a pathogen (e.g., a virus), or other molecule to which a specific T cell response is desired, to a K562 cell and allowing the cell to process and present the antigen thereby generating the desired antigen-specific response.

In an additional experiment, it was demonstrated that specific ligands promote unexpected expansion of antigen specific CD8 T cells. FIG. 21 illustrates CMV specific T cells isolated by tetramer sorting and stained with CFSE and mixed with the aAPC at 2:1 ratio. FIG. 21A illustrates the CMV specific CD8 cells, FIG. 21B illustrates CMV specific CD8 cells contacted with K32 cells loaded with anti-CD3 antibody. FIG. 21C depicts CMV specific CD8 cells contacted with aAPCs expressing CD32, IL-15, 4-1BBL, CD80 and anti-CD3. These data demonstrate that the addition of costimulatory ligands (in this case CD80 IL-15 and 4-1BBL) unexpectedly promote the expansion of antigen specific CD8 T cells.

Example 6 aAPC Expansion of HIV-1 Specific CD8 T Cells with Restored Effector Functions

Attempts to augment HIV-specific T cell response by autologous transfer of antigen-specific CD8 T cells have not resulted in long-term containment of HIV infection (Tan et al., 1999, Blood 93:1506; Koenig et al., 1995, Nature Med. 1:330-336; Brodie et al., 1999, Nature Med. 5:34-41; Riddell et al., 1996, Nature Med. 2:216-223; Lieberman et al., 1997, Blood 90:2196-2206). The inability of these cells to survive in vivo precluded any attempt to measure an anti-HIV response in a clinically meaningful way. In some cases the early demise of these cells was easily explained as immune recognition of a selectable marker (Riddell et al., 1996, Nature Med. 2:216-223). In other cases, the reasons for T cell death upon infusion were less clear. These early trials used slightly different variations of loading peripheral mononuclear blood cells (PMBCs) or lymphoblastoid cell lines (LCLs) with HIV-specific peptides, performing limiting dilution to isolate clones, and expanding the T cells ex vivo for several months using high levels of exogenous IL-2 and TCR triggering in the absence of costimulation to produce up to $1 \times 10^9$ HIV-specific T cells. Without wishing to be bound by any particular theory, it may be that extended ex vivo culture, coupled with a dependence on high levels of IL-2, led to the initiation of apoptosis in these cells once infused back into their host.

While bead-based aAPCs (CD3/28 coated beads) are efficient vehicles to expand CD4 T cells from HIV-infected individuals (Levine et al., 1996, Science 272:1939-1943), there are a number of potential advantages to using cell-based aAPC (gene-modified K562 cells) for use in HIV adoptive transfer clinical trials. First, cell-based aAPCs expand T cells much more robustly than bead-based systems (Parry et al., 2003, J. Immunol. 171:166-174). This reduces the time required to obtain therapeutic quantities of T cells, lowering the cost of these therapies and perhaps improving the function of the cells once they are infused back into the patient. Next, additional costimulatory molecules can easily be introduced into the aAPC by lentiviral transduction. Importantly, CD3/28 coated beads are effective only to expand CD4 T cells (Laux et al., 2000, Clin. Immunol. 96:187-197; Deeths et al., 1999, J. Immunol. 163:102-110). Thus, in order to test the immune reconstitution potential of infusing both CD4 and CD8 ex vivo expanded T cells back into HIV infected individuals, new expansion systems must be developed and such systems are disclosed herein.

It is useful to create APCs that optimally expand CD8 T cells from HIV infected individuals. Previously, K562 cells were transfected with CD32 (to bind stimulatory Ab) and 4-1BBL as the minimal aAPC that induces long-term expansion of CD8 T cells. Also, it was demonstrated that CD86 triggered CD28 endowed T cells with the same proliferative ability as triggering CD28 endowed T cells with an anti-CD28 Ab (Thomas et al., 2002, Clin. Immunol. 105:259-272). Because it was desire to develop Ab independent culture systems, CD86 was used rather than anti-CD28 to trigger both CD28 costimulatory effects on T cell expansion and HIV replication. Thus, the following five aAPCs can be used to expand and functionally test CD8 T cells from HIV infected patients: KA2/32/86, KA2/32/86/4-1BBL, KA2/32/86/4-1BBL/CD83, KA2/32/86/4-1BBL/ICOS-L and KA2/32/86/4-1BBL/CD83/ICOS-L. KA2/32/86 can stimulate CD8 T cells but does not endow them with long term growth potential (Maus et al., 2002, Nature Biotechnol. 20:143-148). This aAPC serves as a negative (or baseline) control to which other costimulatory ligands can be compared. All of the aAPCs created express both HLA-A2 and CD32. This allows use of the same aAPC to expand polyclonal CD8 T cells by having signal one delivered by CD32 bound anti-CD3 Ab (FIG. 1) or antigen specific T cells by having signal one initiated by peptide bound in HLA-A2.

KA2/32/86/4-1BBL is the minimal aAPC to expand CD8 T cells from healthy donors (Maus et al., 2002, Nature Biotechnol. 20:143-148). Additional costimulatory signals may be required to expand HIV-specific T cells with improved effector functions. Comparison of cells expanded with this aAPC with those cells expanded with the aAPCs listed below allows for the identification of any additional desirable costimulation signals.

KA2/32/86/4-1BBL/CD83 is used because CD83 is a marker of mature DCs whose role in T cell activation has recently been investigated. Stimulation of T cells with magnetic beads coated with anti-CD3 and CD83Ig fusion protein enhanced the ratio of CD8 to CD4 T cells, suggesting that CD83 ligation preferentially activates CD8 T cells. Moreover, CD83-expressing tumor cells were more efficiently killed by CD8 T cells and primed the immune system to also reject CD83-deficient tumors (Scholler et al., 2001, J. Immunol. 166:3865-3872; Scholler et al., 2002, J. Immunol. 168:2599-2602).

KA2/32/86/4-1BBL/ICOS-L is used because ICOS-L binds the CD28-related molecule inducible costimulator protein (ICOS), delivering a potent costimulatory signal to T cells that enhances production of effector cytokines (IFN-γ, IL-4, and IL-13) but is curiously unable to produce high levels of IL-2 (Hutloff et al., 1999, Nature 397:263-266) or induce the survival factor Bcl-xL (Parry et al., 2003, J. Immunol. 171:166-174). The precise roles that ICOS and CD28 play in the immune system are still unclear but comparing the outcome of ICOS and CD28 blockade in several disease models has revealed clues. Blockade of either ICOS or CD28 interferes with both IFN-γ production and generation of protective immunity in lymphocytic choriomeningitis virus (LCMV) (Kopf et al., 2000, J. Exp. Med. 192:53-61) and *Toxoplasma gondii* (Villegas et al., 2002, J. Immunol. 169:937-943) infection-models, suggesting a non-redundant relationship between ICOS and CD28 costimulation. Moreover, examination of when the costimulatory blockade is administered has revealed that CD28 is crucial for priming, while ICOS is more important to maintaining a T cell response (Gonzalo et al., 2001, Nature Immunol. 2:597-604; Coyle et al., 2000, Immunity 13:95-105). ICOS-L stimulation promotes effector functions in both CD4 and CD8 T cells (Villegas et al., 2002, J. Immunol. 169:937-943; Mittrucker et al., 2002, J. Immunol. 169:5813-5817; Wallin et al., 2001, J. Immunol. 167:132-139).

KA2/32/86/4-1BBL/CD83/ICOS-L allows, among other things, examination of whether there is synergy between CD83 and ICOS-L signaling in generating an immune response.

These aAPCs allow the experimentation of whether the effector functions can be restored to T cells from HIV-1 infected donors through optimal ex vivo expansion. Upon completion of creating the aAPCs, their ability to expand polyclonal CD8 T cells isolated from HIV infected patients were assessed and it was determined if and how ex vivo expansion had altered the ability HIV-specific T cells to respond to antigen stimulation. Next, a similar analysis using Pol-specific cells isolated from HIV infected and non infected individuals was preformed. These studies demonstrate the potential use of aAPCs for clinical trials and allows the study of how HIV infection influences the development of HIV specific CD8 T cells.

Methods describe in this Example relate to the purification of Pol-specific and polyclonal CD8 T cells from HIV infected and non-infected individuals. These cells serve as the source material used in methods disclosed herein.

Source and Purification of HIV-1 Infected T Cells

HLA-A2 donors are used because of the high prevalence of this allele in the population. Initially, viral phenotype is not used as a patient selection criteria for HLA-A2 donors. It has been demonstrated that naïve CD8 T cells express low amounts of CD4 on their cell surface after activation, making them susceptible to HIV infection (Yang et al., 1998, J. Exp. Med. 187:1139-1144; Kitchen et al., 1998, J. Virol. 72:9054-9060; Flamand et al., 1998, Proc. Natl. Acad. Sci. U.S.A 95:3111-3116; Imlach et al., 2001, J. Virol. 75:11555-11564). However, only naïve CD8 T cells appear to have this plasticity and the Pol-specific T cells used are by definition memory T cells. Thus, not wishing to be bound to any particular theory, these cells are not infected and will not become infected upon ex vivo expansion.

In addition to using HLA-2 donors, PBMCs can be used. PBMCs are stained with FITC labeled HLA-A2 specific Ab, BB7.2, (BD Pharmingen). Desired cells can be obtained from HLA-A2 donors apheresis. A cross-section of CD4 T counts and viral loads is obtained from the apheresis product. A sample of the apheresis product is used to perform a Ficoll/Hypaque gradient, and PBMCs are frozen in 50 million/vial aliquots. With the remaining apheresis product, monocytes are removed by elutriation to create PBLs and approximately 50 million CD4 T cells are isolated by negative selection (Maus et al., 2002, Nature Biotechnol. 20:143-148). The remainder of the PBLs is used to make purified CD8 T cells (by negative selection) and used in the methods and experiments described herein.

It has been measured that the percent of HIV Pol-specific T cells by tetramer stain is found to be approximately 0.7%±1.1 (Sun et al., 2003, Journal of immunological methods 272:23-34; Kostense et al., 2002, Blood 99:2505-2511; Rinaldo et al., 2000, J. Virol. 74:4127-4138). Thus, from 100 million CD8 T cells, about 700,000 HIV Pol-specific CD8 T cells is recovered. Live sorting HIV infected T cells presents a number of technical and safety issues. Vantage SE/DiVa is a full-featured sorter capable of measuring 12 colors plus forward and side scatter. Vantage SE/DiVa has been outfitted with enhanced safety features (Perfetto et al., 2003, Cytometry 52A:122-130) that allows it to safely sort infectious materials into 4 populations at once.

Source and Purification of Pol-Specific T Cells from Non HIV Infected Host

Seven HLA-A2 breast cancer patients were vaccinated to the Pol peptide, ILKEPVHGV (SEQ ID NO:3), as a control arm to an hTERT peptide vaccine (Vonderheide, 2004, Clin. Cancer Res. 10:828-839). Cells from the vaccinated HLA-A2 breast cancer patients are used to expand Pol-specific cells from a HIV negative host. Frozen PMBCs from these patients are used to purify Pol-specific T cells. The frequency of these Pol-specific T cells is lower than the frequency expected from HIV infected donors (approximately 0.1%) so fewer (but still a sufficient number) of these cells are obtained to initiate experiments. Pol specific T cells patients can be obtained from any patient that has been vaccinated with a Pol peptide.

During the ex vivo expansion, the cultures are monitored for the evidence of HIV infection by using p24 ELISA, as HIV infection skews the results. In the case where an infection is observed, patients who are infected with R5 viruses are used. R5 viruses are unable to replicate in CD3/28 costimulated T cells due to high levels of secretion of the CCR5 natural ligands RANTES, MIP-1 and MIP-1β as well as downregulating the steady state levels of the CCR5 transcript (Riley et al., 1997, J. Immunol. 158:5545-5553; Carroll et al., 1997, Science 276:273-276). Thus, CD28 costimulation permits the long term growth of R5 infected T cells without the addition of anti-viral components which may alter the expansion properties of T cells. Viral tropism is determined using the GHOST cell assay developed by Littman and colleagues.

Also, the experiments disclosed herein do not require pure Pol-specific T cells. HIV-1 Pol-specific CD8 T cells isolated by tetramer coated magnetic beads can be used (Maus et al., 2003, Clin. Immunol. 106:16-22). This method can provide sufficient enrichment of Pol-specific T cells, and can be used to isolate the Pol-specific cells.

Example 7

Characterization of Ex Vivo Expanded Polyclonal CD8 T Cells

The ability to expand bulk T cells from HIV infected patients is examined before characterizing the ability of these aAPCs to expand HIV specific T cells. This allows for the measurement of the expansion rate to determine whether a particular T cell subset is preferentially expanded by one aAPC over another. In addition, the analysis of tetramer staining coupled with IFN-γ secretion and perforin expression is used to determine whether a particular aAPC preferentially expands and/or endows improved effector function to flu, CMV, EBV or HIV specific CD8 T cells.

A comparison of these studies with those that expand HIV specific CD8 T cells in isolation to determine whether HIV specific T cells have unique costimulatory ligand requirements for expansion and induction of effector functions. The following attributes are measured:

T Cell Expansion

To generate therapeutic levels of HIV specific CD8 T cells, T cells are expanded to between about 10,000 and about 1,000,000 fold (about 13-20 population doublings) (Riddell et al., 1995, Annu. Rev. Immunol. 13:545-586). There is an inverse relationship between the amount of time HIV specific CD8 T cells spend in ex vivo culture and the potential clinical benefit these cells provide to HIV infected patients. Thus, the aAPC which most rapidly expands CD8 T cells from HIV infected patients is determined and used in the methods disclosed herein.

T Cell Survival and Replicative Potential

The fitness of T cells after ex vivo expansion is an excellent predicator of their ability to function in vivo. The ability of these aAPCs to induce the key cell survival gene Bcl-xL is also measured. The percentage of apoptotic cells in a culture during the expansion process is used to determine whether any of the cell based aAPCs confer a particular survival advantage to the expanded T cells. Additionally, the telomere length of cells after ex vivo expansion is measured to determine if a particular aAPC is more effective in preserving the replicative potential of the cells it expands. At the end of each chromosome there are a large number TTAGGG nucleotide repeats that are called telomeres. Each time a cell divides it losses a portion of its telomeres. Since most cells do not express the enzyme telomerase, which can restore copies of the DNA repeat to the ends of chromosomes, it is believed that once a cell has lost a critical mass of its telemetric length it loses its ability to divide. Telomere lengths have been used in the art as a way to gauge how many times a cell has replicated and, by inference, to assess its future replicative potential (Palmer et al., 1997, J. Exp. Med. 185:1381-1386; Weng et al., 1997, J. Immunol. 158:3215-3220). However, T lymphocytes are one of the few cell types that can induce telomerase activity (Weng et al., 1996, J. Exp. Med. 183:2471-2479) and thus the relative differences between T cells expanded using different methods reflect both the number of T cell mitotic events as well as the extent telomerase was induced. Infusing cells that have the most replicative potential is paramount to ensure that adoptive transferred HIV specific T cells control HIV infection on a long-term basis.

Cytokine Production

Cytokines are important effector molecules and provide insight into T cell differentiation. The ability of each of the aAPC to induce the following cytokines from CD8 T cells derived from HIV infected individuals is quantitated: IL-2 (a key T cell growth factor for ex vivo expansion and a cell's ability to induce IL-2 correlates well with its long term growth potential); IL-4 (a marker for TH2 differentiation); and IL-10 (an immunosuppressive cytokine that may be surrogate for T regulatory cell outgrowth). For HIV infected patients, aAPCs that induce T cells to produce low levels of IL-10 is preferred. Other cytokines include, but are not limited to, TGF-β (for the same rationale as IL-10); IFN-γ (a marker for TH1 differentiation and an important effector cytokine); and TNFα (an important effector cytokine).

Tetramer and Effector Function Analysis

The tetramer/intracellular IFN-γ and perforin staining assay developed by Immunomics (per manufacturer's instructions) allows both the detection of antigen specific T cells coupled with phenotypic analysis and functional assays. This flow based method is the most rigorous assay of antigen specific T cell function currently available. This assay is used to determine how ex vivo expansion affects the total number and function of HIV specific T cells.

T Cell Expansion

To evaluate how these aAPCs expand bulk HIV-1 infected T cells, each aAPC was irradiated, coated with anti-CD3 Ab, and mixed with purified CD8 T cells from an HIV-1 infected patient at a 1:2 aAPC to T cell ratio. To compare the initial rate of cell expansion, the cells were subject to CFSE staining rather than $^3$H thymidine uptake to determine how well each aAPC induced the proliferation of all T cells because CFSE staining provides a much more quantitative endpoint and allows simultaneous phenotyping of the expanded cells. Approximately 20 million purified CD8 T cells from an HIV infected individual are mixed with 3 μM CFSE for 8 minutes, washed extensively to remove the unbound CFSE, and stimulated with the aAPCs. Every day after stimulation, an aliquot of cells is removed from each culture and analyzed by flow cytometry. CFSE staining makes cells highly fluorescent. Upon cell division, the fluorescence is halved and thus the more times a cell divides the less fluorescent it becomes. The ability of each aAPC to induce T cell proliferation is quantitated by measuring the number of cells that divided once, twice, three times and so on. The aAPC that induces the most number of cell divisions at a particular time point is deemed as the most potent expander of CD8 T cells from HIV infected individuals (Wells et al., 1997, J. Clin. Invest. 100:3173-3183).

However, CFSE staining can only detect a limited number of T cell divisions (approximately 7), and to generate therapeutic quantities of T cells for immunotherapy, 13-20 population doublings may be necessary. Therefore, to determine how well these aAPCs promote long-term growth of T cells, cell growth curves are generated. These experiments are set up exactly as the CFSE experiments as described elsewhere herein, but no CFSE is used. Every 2-3 days of culture, T cells are removed from the respective cultures and counted using a Coulter counter which measures how many cells are present and the mean volume of the cells. The mean cell volume is the best predicator of when to restimulate the cells. In general, when T cells are properly stimulated they triple their cell volume. When this volume is reduced to more than about half of the initial blast, it may be necessary to restimulate the T cells to maintain a log linear expansion (Levine et al., 1996, Science 272:1939-1943; Levine et al., 1997, J. Immunol. 159:5921-5930). The time it takes each aAPC to induce 20 population doublings is calculated. The relative differences of each aAPC to induce this level of T cell expansion is an important criteria on which a particular aAPC is used to move forward to clinical trials.

The phenotypes of the cells expanded by each aAPC are characterized to determine whether a particular subset is preferentially expanded. Prior to each restimulation, a phenotype analysis of the expanding T cell populations is performed to define the differentiation state of the expanded T cells using the CD27 and CD28 definitions proposed by Appay et al. (2002, Nature Med. 8, 379-385) and CCR7 definitions proposed by Sallusto et al. (1999, Nature 401:708-712). Perforin and Granzyme B intracellular staining are used to perform a gross measure to estimate cytolytic potential.

Apoptosis Rate and Telomere Length

Annexin V/To-Pro (Molecular Probes, Eugene, Oreg.) staining is performed before each restimulation to determine whether differences in the growth rate reflect differences in the number of cells undergoing apoptosis. The experimental details of this assay are described in detail in Maus et al. (2002, Nature Biotechnol. 20:143-148). Culture conditions that lead to the least amount of apoptosis are desirable.

Telomere length is measured using various established techniques known in the art, but a preferred method is to use the flow FISH method since it can be performed relatively quickly using far fewer cells and is easier to quantitate. In this method, approximately 1 million T cells (although far fewer are required) are denatured using heat and 75% formamide, and then hybridized with a FITC conjugated DNA probe to the TTAGGG sequence. Unbound probe is washed away and the DNA is counterstained with LDS 751. A mixture of 4 populations of FITC labeled beads, each having known amounts of molecule equivalents of soluble fluorochrome (MESF), is analyzed in each experiment to allow for the creation of a calibration curve and the determination of the relative telomere length of each culture over time (Baerlocher et al., 2002, Cytometry 47:89-99). Relative telomere length is measured prior to each restimulation and is recorded for whether any of the aAPCs expand T cells that have significantly longer telomeres.

Cytokine and Bcl-xL Expression

To investigate cytokine production and Bcl-xL expression levels, RNA is isolated from approximately 1 million cells 24 hours after each stimulation and subjected to quantitative RT-PCR to examine the relative expression of but not limited to IL-2, IL-4, IL-10, IFN-γ, TNF-α, and Bcl-xL. Experimental details of these established assays can be found in Maus et al. (2002, Nature Biotechnol. 20:143-148), Thomas et al. (2002, Clin. Immunol. 105:259-272), and Parry et al. (2003, J. Immunol. 171:166-174). Many discrepancies between TGF-α mRNA levels and secreted cytokine have been noted (Assoian et al., 1987, Proc. Natl. Acad. Sci. USA 84:6020-6024) so TGF-α production is measured by ELISA.

Tetramer and ELISPOT Analysis

The ability of expanded CD8 T cells to recognize common recall antigens and HIV is compared. Prior to expansion, the purified CD8 T cells are stained using the following, among others, HLA-A2 tetramers GLCTLVAML (SEQ ID NO:4) (EBV BMLF), NLVPMVATV (SEQ ID NO:5) (CMV p65), SLYNTVATL (SEQ ID NO:6) (HIV gag p17), ILKEPVHGV (SEQ ID NO:3) (HIV RT pol), GILGFVFTL (SEQ ID NO:1) (Flu matrix), and LLFGYPVYV (SEQ ID NO:7) (HTLV Tax) and the frequency of these tetramers is determined prior to ex vivo expansion. Next, the bulk CD8 T cells from an HIV infected donor is stimulated using the aAPCs disclosed herein and the cells are expanded using methods described herein. Prior to each restimulation, the expanded T cells are subjected to tetramer staining to determine whether the relative frequency of EBV, CMV and HIV specific T cells has been altered by stimulation by a particular aAPC.

It is important to determine the frequency of cells that secrete IFN-γ and the frequency of cells that express high levels of perforin after antigen recognition. The tetramer/intracellular IFN-γ staining assay developed by Immunomics, which combines an intracellular cytokine assay with tetramer staining to perform flow based functional assays using antigen specific cells, can be used. The assay can include incorporation of an intracellular stain for perforin expression. Prior to freezing the PBMCs isolated from each patient, a tetramer/intracellular IFN-γ and perforin staining assay using each of the peptides listed elsewhere herein is used to determine the initial tetramer positive/IFN-γ secreting/perforin producing population. For each peptide with a corresponding tetramer, approximately 1 million PBMCs are placed into three tubes for the following experimental conditions and controls: 1) non-peptide stimulated control, 2) control tetramer stain without peptide stimulation, and 3) tetramer plus peptide tube. Next, the appropriate tetramer is added to each tube and incubated for 30 minutes at room temperature. Two micrograms of peptide is added to the third tube and the sample is incubated for 1 hour at 37° C. Brefeldin A is added to all three tubes and the tubes are incubated for another 4 hours. Since all of the tetramers are labeled with P5-Cy5.5 and APC-Cy7, PerCP, and APC labeled CD27 and CD28 Ab can be used to determine the differentiation state of the virus specific T cells. The cells are lysed, fixed and permeabelized and IFN-γ FITC labeling protocols are performed using methods known in the art and methods disclosed herein. There has been success in measuring perforin expression by co-incubating a PE labeled anti-perforin Ab with the IFN-γ Ab, allowing the simultaneous measurement of IFN-γ expression and perforin expression. Given the discrepancy reported between IFN-γ secreting HIV specific T cells and those that have potential to kill (Zhang et al., 2003, Blood 101:226-235) this analysis is used to determine how ex vivo expansion with the various cell based aAPCs alters either of these functional attributes. The cells are fixed in PFA and analyzed by flow cytometry. This analysis establishes the baseline phenotype of IFN-γ perforin expressing cells. To determine if the percentage of tetramer positive cells or the phenotype of the cells secreting IFN-γ, or expressing high levels of perforin, is altered after ex vivo expansion, the tetramer/intracellular IFN-γ staining assay is performed using the differentially expanded CD8 T cells. To do this, autologous PBMCs are used and the percentage of CD8 T cells present is determined and the CD8 T cells are removed by magnetic bead depletion. The depleted CD8 T cells are reconstituted with those expanded by the K562 based aAPCs described elsewhere herein and subjected to the tetramer/intracellular IFN-γ staining assay as described elsewhere herein. These experiments provide an indication as to which aAPCs were able to alter the functional phenotype of HIV specific T cells during ex vivo expansion.

The data disclosed herein demonstrate the phenotype of CD8 T cells isolated from HIV infected individuals expanded by the cell based aAPCs. While not wishing to be bound by any particular theory, it predicted that a subset of aAPCs can expand HIV specific T cells with improved effector functions. This result would confirm that these effector functions can be restored by ex vivo expansion. By process of elimination, which signals are necessary for this transformation is determined according to the methods described herein. This finding is confirmed by growing HIV specific T cells in isolation and provides a rationale for making the aAPC a GMP reagent and performing Phase I clinical trial to see if the improved ex vivo expanded CD8 T effector cells can help control HIV infection in patients. Additionally, this outcome establishes an experimental system to study the mechanisms mediating the defect(s) of HIV specific T cells and how a particular costimulatory ligand can overcome or reverse this defect.

Example 8

Characterization of Ex Vivo Expanded Pol-Specific T Cells

The methods disclosed herein provide important insights into which aAPC is best at expanding HIV specific CD8 T cells by examining the expansion and function of these cells within the milieu of polyclonal T cell expansion. However, the translational value of ex vivo expanded polyclonal T cells from HIV infected individuals is low since the number of total CD8 T cells is increased in most HIV infected patients as homeostatic mechanisms adjust for the loss of CD4 T cells and there appear to be no gross abnormalities in non HIV specific CD8 T cells (Gandhi et al., 2002, Annu. Rev. Med. 53:149-172). Thus, to improve HIV specific CD8 T cell response by autologous adoptive transfer, systems that expand only the HIV specific T cells and endow them with effector functions that can eliminate HIV infection on a long-term basis is desired.

It is desirable to expand tetramer isolated Pol-specific T cells using each of the cell based aAPCs and determine which generates Pol-specific T cells that best can kill HIV infected cells with the highest replicative and survival potential. These studies are performed using Pol-specific cells isolated from HIV infected individual with Pol specific T cells isolated from cancer patients vaccinated with Pol-specific peptide. This comparison provides a unique insight on the effects HIV has on the generation of antigen specific cells since the same reagents and assays can be used to study these Pol-specific T cells isolated from these two disease types. These studies may provide insight into the nature of the defect of HIV specific T cells and lead new hypotheses on how to overcome these defects.

T Cell Expansion and Phenotype

On average, 700,000 Pol-specific T cells are isolated from an HLA-A2 positive HIV infected individual and approximately 100,000 Pol-specific T cells from a vaccinated cancer patient. Antigen specific expansion can be accomplished using as few as 1,500 T cells (FIG. 3). To make the culture conditions equivalent, cultures are started by mixing 7,500 Pol-specific T cells and 15,000 of the aAPCs described elsewhere herein (it has been observed that inverting the T cell to APC ratio is important when expanding so few cells) with 0.5 ng/ml of anti-CD3 Ab in a total of 100 μl of media in a 96 well plate. To compare the ability of anti-CD3 and K562 processed and presented antigen to stimulate these cells, an identical set of cultures whose aAPCs have also been transduced with a Pol-GFP expression vector is expanded. Thus, 10 cultures for each donor's cells are available. Freshly irradiated aAPCs are added to the growing polyclonal T cells every 10-12 days at an estimated 1 aAPC to every 2 T cell ratio. Once the population expands to a point where an accurate quantitation of the number of cells present can be calculated using a Coulter counter, the expansion rate of each population is tracked. The CD28/CD27 phenotype of the Pol-specific T cells isolated from the HIV and cancer patients before and after T cell expansion is compared.

Cytokine Production, Bcl-xL Expression, Apoptosis Rate, and Telomere Length Assessment These studies are performed using methods disclosed elsewhere herein except the analysis is comprised of using several million cells present (approximately 30 days). Nonetheless these studies should confirm the results disclosed elsewhere herein using polyclonal T cells.

Killing of HIV Infected Targets

One advantage of expanding antigen specific T cells in isolation is that multiple killing and other functional assays can be performed in a very quantitative manner. The first test is the tetramer/intracellular IFN-γ and perforin expression assay. As disclosed elsewhere herein, ex vivo expanded CD8 T cells are mixed with the autologous CD8 depleted PBMCs. Since most of the CD8 T cells are tetramer positive, quantitative data is obtained concerning which aAPCs produce T cells that produce the highest levels of IFN-γ and perforin upon contact with Pol peptide. Additionally, since the number of tetramer cells is not limiting, a complete phenotype analysis of these cells using CCR7, CD27, CD28, CD62L, CD45 RO, CD45 RA, and CD57 (Brenchley et al., 2003, Blood 101:2711-2720) is performed, thereby correlating the effector function(s) with T cell phenotype.

The ability of the differentially expanded Pol-specific T cells to kill T2 cells loaded with the Pol peptide via $^{51}$Cr release assay is assessed. In this assay, the T2 cells are loaded with the Pol peptide ILKEPVHGV prior to the uptake of $^{51}$Cr. After extensive washing, the labeled T2 cells are incubated with antigen specific T cells at 1:30, 1:10, 1:3 and 1:1 and 1:3 ratios for 4 hours. If the antigen specific T cells recognize the peptide presented on the T2 cells and have the ability to kill these cells, then $^{51}$Cr is released and can be detected. No peptide controls and detergent lysis controls allow the determination of specific lysis. The lowest target to effector ratio in which a high degree of specific lysis is observed indicates which aAPC expands T cells with the greatest killing ability.

The ability of ex vivo expanded Pol specific T cells to kill T2 cells are compared with the ability of these cells to kill Pol expressing CD4 T cells. This scenario more closely mimics the in vivo targets of the ex vivo expanded CD8 T cells. The ability of these cells to kill HIV infected CD4 T cells is the ultimate proof of principle. Moreover, it is likely that cells that are infected at this level would generate a very high background in the $^{51}$Cr release assay making it difficult to determine the effectiveness of the expanded CD8 T cells. As an alternative, autologous CD4 T cells are transduce with Pol IRES GFP expression lentiviral vector that allows the tracking of Pol expressing cells by GFP expression. It was observed that approximate 50% of T cells transduced by these vectors (see Parry et al., 2003, J. Immunol. 171:166-174, for details how the T cells are transduced with lentiviral vectors) which produces enough targets for $^{51}$Cr release assays. Pol transduced as well as non-transduced CD4 T cells are labeled with $^{51}$Cr. CD4 T cells do not uptake $^{51}$Cr as well as T2 cells, so the target is shifted to effector ratio of 1:100, 1:30, 1:10 and 1:3 to improve the sensitivity of the assay. Differences between the non-expanded and expanded CD8 T cells in their ability to kill Pol expressing CD4 T cells provide a strong rationale to further develop one aAPC over another.

CD28 expression is required for long-term ex vivo expansion of CD8 T cells. It has been recently observed that restoration of CD28 expression by retroviral transduction (Topp et al., 2003, J. Exp. Med. 198:947-955) restores the ability of CD28 negative cells to produce IL-2 and to expand without the presence of CD4 T cells. Recently, it has been shown that IL-12 restores CD28 expression to CD28 negative T cells (Warrington et al., 2003, Blood 101:3543-3549). To determine whether IL-12 can enhance CD28 expression and improve the long-term growth potential of Pol-specific T cells, 10 ng/ml of IL-12 is added to the various aAPCs/Pol-specific cultures and the cells are assessed for how well CD28 expression is improved in the Pol-specific cells and whether any of the aAPCs can expand Pol-specific cells in long term culture. Other cytokines, such as IL-21 and IL-15, may work in concert with IL-12 to induce HIV specific T cell expansion. IL-21 is a multifunctional cytokine that induces T and B cell proliferation and natural killer (NK) cell differentiation (Parrish-Novak et al., 2002, J. Leukoc. Biol. 72:856-863). IL-21 is produced exclusively by activated CD4 T cells and synergizes with IL-2 and IL-15 to promote CD8 T cell growth. Likewise, IL-15 is a key CD8 T cell survival factor and is produced by activated macrophages and DCs (Waldmann et al., 2001, Immunity 14:105-110) whose addition may also enhance CD8 T cell expansion.

In the event cytokines fail to permit long term expansion of HIV specific T cells, Pol-specific T cells are transduced with a lentivirus that expresses CD28. As outlined in Parry et al., 2003, J. Immunol. 171:166-174, greater than 90% of T cells can be transduced with a single transgene vector (as disclosed herein, IRES containing vectors are less efficient). Thus, to test whether transduction of CD28 restores long-term growth to Pol-specific T cells, Pol-specific T cells are spinoculated (O'Doherty et al., 2000, J. Virol. 74:10074-10080) with CD28 expressing lentiviral vector immediately prior to mixing these cells with aAPCs. T cell activation induced by these aAPCs facilitates integration of this vector and expression of the transgene can be observed 12 hours post transduction. These cells are cultured as disclosed elsewhere herein, and Pol specific T cells that are recovered. This is an indication that CD28 costimulation is required for the long term expansion of these cells. If lentiviral transduction is used as a necessary step to expand HIV specific T cells, it may slow the translational impact of these results. However, it has been recently demonstrated that lentiviral transduction of T cells from a HIV infected individual may be a viable therapeutic option.

Example 9

Expansion of HIV Specific CD8 T Cells with Broad Specificity

Infusion of a single CD8 clone that recognized a Nef epitope led to the selection of viruses that did not express this epitope (Koenig et al., 1995, Nature Med. 1:330-336) indicating that T cells with multiple specificities are required to prevent HIV escape mutants. A potentially powerful way to generate T cells that recognize multiple epitopes of a specific virus from a patient is to have the cell-based aAPCs uptake and present antigen similar to that of natural APCs. By loading a patient's chemically inactivated virus onto an MHC-expressing, K562-based aAPC and mixing in autologous T cells, patient-specific anti-HIV T cells can be expanded. By providing this optimal situation by which HIV specific T cells encounter HIV specific antigens, T cells that recognize both immunodominant and cryptic antigens can be expanded, thus resulting in a greater potential for controlling HIV infection. Moreover, T cells from a non-infected, healthy person with shared HLA class I alleles can be ex vivo vaccinated with the recipient's chemically inactivated virus, expanded and infused into the HIV infected patient. This represents a powerful potential treatment option for an individual with advanced disease and with a limited T cell repertoire.

Recently, Lu et al. (2003, Nature Med. 9:27-32), demonstrated that macaques infused with DCs loaded with a chemically inactivated form of SIV had significantly less viral RNA and DNA levels, suggesting that the T cell response initiated using this immunotherapy approach can control SIV infection. These data suggest that properly primed T cells can control SIV infection and strengthens the prospects for a cell-based HIV vaccine in humans (Bhardwaj et al., 2003, Nature Med. 9:13-14). Inactivated virus is used to load MHC-expressing, K562-based aAPCs similarly to the chemically inactivated SIV study described elsewhere herein. The complexes are used to expand HIV-specific T cells ex vivo to create a patient specific T cell therapeutic vaccine. The complexes can also be administered to a patient using an in vivo approach.

CD107a and 107b are lysosomal associated proteins that are not normally found on the T cell surface. Upon TCR triggering, degranulation of CD8 T cells occurs rapidly, and CD107 and other lysosomal proteins are transported to the cell membrane to facilitate the release of perforin and granzyme. Betts et al. (2003, J. Immunol. Methods 281:65-78), demonstrated that CD107 expression can be detected on an antigen specific CD8 T cells as early as 30 minutes post stimulation with maximal expression 4 hours post-stimulation. Thus, antigen specific effectors can be identified without killing the desired T cells thereby identifying which antigen is activating the cells. Similar studies to identify and expand HIV specific T cells are performed as disclosed herein.

FIG. 4 illustrates, without wishing to be bound by any particular theory, an experimental approach for expanding HIV specific CD8 T cells with a broad specificity. Banked T cells and high titer, autologous viral isolates from a recently completed adoptive transfer clinical trial are available (Levine et al., 2002, Nature Med. 8:47-53) and are used in the methods disclosed herein. A patient's viral isolate is inactivated using 250 µM of aldrithiol-2 (AT-2) in order to preserve the fusogenic potential of the virus (Lu et al., 2001, J. Virol. 75:8949-8956). The ability of AT-2 to inactivate HIV is validated by infecting PHA blasts with this treated virus and measuring p24 production over a two week period. In order to permit HIV fusion, the cell based aAPC that best allowed expansion of Pol-specific T cells is transduced with CD4 and CCR5 lentiviral expression vectors that are already available (Simmons et al., 2003, Virology 305:115-123). K562 cells naturally express CXCR4 (Gupta et al., 1999, J. Leukoc. Biol. 66:135-143). These aAPCs are pulsed with the inactivated virus (50 ng of p24/million cell based aAPC) for 2 hours at 37° C. (Lu et al., 2001, J. Virol. 75:8949-8956). Fifty million CD8 T cells from the patient are mixed with antigen loaded aAPCs in duplicate. With one culture, the utility of using CD107 mobilization as a surrogate of antigen specific T cells endowed with enhanced effector functions is assessed. Four hours after stimulation, the cells are stained for CD8 and CD107, the CD8$^+$CD107$^+$ cells are sorted using the BLS 3 sorter and are expanded in isolation using "infected" aAPCs. With the other set of cells, the ability of these aAPCs to selectively expand HIV specific T cells from the polyclonal population is tested. Chemically inactivated HIV infected aAPCs can be used to stimulate the bulk CD8 T cells from the HIV infected individual every 10 days. As a control, both aAPCs cells that have not been pulsed with virus, which should only expand cells that recognize K562 antigens, and an αCD3-coated aAPC that expands all cells, are used. After two weeks of expansion, the cultures are monitored and the cells are assessed to determine whether HIV-specific T cells that recognize the patient's own virus better than a reference strain of HIV are being enriched. PHA is used stimulate and superinfect the patient's CD8 T cell depleted PBMCs with either high titer patient virus (approximately $5 \times 10^5$ TCID$_{50}$/ml) or similarity high titer Bal (for R5 patients) or NL4-3 (for X4 patients) viruses for 3 days. Most of the patients that received ex vivo expanded, autologous CD4 T cells had undetectable viral loads (Levine et al., 2002, Nature Med. 8:47-53) and thus after only 3 days the vast majority of replicating virus will represent the virus that was superinfected. Approximately 400,000 PBMCs obtained from an infected CD8 depleted patient are mixed with 100,000 CD8 T cells expanded from aAPC infected with the patient's own virus. After 24 hours, the percentage of CD8 T cells expressing INF-λ and perforin is measured by intracellular flow cytometry. If more CD8 T cells expressing IFN-λ and perforin is observed when mixed with the PBMCs superinfected with the patient's own virus compared with those superinfected with Bal or NL4-3 reference strains, aAPC presentation of the patient virus likely allowed the expansion of T cells that selectively recognize the patient's viral epitopes. This approach has tremendous potential to increase the breadth of a patient's HIV response against his or her own virus and can potentially elicit responses against cryptic epitopes not well presented during a natural HIV infection (Sewell et al., 1999, J. Immunol. 162:7075-7079). Moreover, these experiments provide a determination of whether CD107 staining provides a more robust way to identify and expand HIV specific T cells.

It was previously demonstrated that high affinity CTLs were generated from APCs expressing lower antigen levels (Alexander-Miller et al., 1996, Proc Natl. Acad. Sci U.S.A. 93:4102-4107; Oh et al., 2003, J. Immunol. 170:2523-2530). Whether aAPCs expressing lower levels of MHC class I are more effective in generating high avidity T cells that have a greater potential to kill their targets is assessed. Based on the disclosure herein, the amount of virus used to load the KA2 cells is titrated, or an aAPC expressing lower amounts of HLA-A2 is used, to ensure that high-affinity T cell responses are generated that are useful for adoptive transfer immunotherapy (Alexander-Miller et al., 1996, Proc Natl. Acad. Sci. U.S.A. 93:4102-4107).

If the chemically inactivated virus loaded aAPC is not an effective method to expand patient specific T cells, this method of generating HIV specific T cells is compared with cross priming methods described by Larsson et al. (2002, AIDS 16:1319-1329). For this method to work, the K562 based aAPC possesses the ability to uptake antigens from dying or dead T cells. T cells are transduced with either GFP or flu matrix-GFP fusion LV construct. These cells are subjected to UVB radiation as described in Schlienger et al. (2003, Clin. Cancer Res. 9:1517-1527), and mixed with the optimal HLA-A2 expressing aAPC. If the aAPC properly processes the dead flu infected T cells, KA2 cells incubated with the apoptotic T cells expressing the flu matrix-GFP fusion protein, but not the ones incubated with T cells expressing just GFP, can expand the flu specific cells as described elsewhere herein. If the KA2 processes and presents antigen from dead cells, a patient's T cells can be superinfected with his/her virus. These cells are subjected to UVB radiation and are incubated with aAPCs. The ability of aAPCs loaded with apoptotic HIV infected cells to promote expansion of HIV specific T cells is then evaluated as described elsewhere herein.

Alternatively, HIV-specific T cells with multiple specificities are expanded using a panel of HIV-specific tetramers. In this approach, an array of HIV-specific tetramers labeled with the same fluorochrome are mixed with T cells from an HIV infected donor and T cells that bind these assorted tetramers are sorted into a single population. This population of antigen specific T cells is expanded using the optimal aAPC, as described elsewhere herein, and the ability of T cells expanded in this manner to recognize and respond to autologous virus versus reference strains are evaluated as described elsewhere herein. Currently, there are defined HLA-A2 tetramers that recognize conserved epitopes in gag, pol, and nef and new tetramers can be created that present HIV-specific peptides. While this approach expands a limited number of antigen specific T cells, it should be sufficient to prevent viral escape. Moreover, the methods disclosed herein can be rapidly translated into Phase I clinical trials.

Example 10

Production and Evaluation of K562 Cells Comprising CD32 or CD64

K562 cells were stably cotransfected with (i) the human Fcγ receptor CD32 to permit exogenous loading of anti-CD3 and anti-CD28 antibodies, and a separate population of cells was transduced with the human Fcγ receptor CD64, which permits high-affinity loading of anti-CD3, anti-CD28, and other receptors, and (ii) human 4-1BB ligand. 4-1BB, also known as CD137, is a member of the TNF receptor family that promotes survival of $CD8^+$ T cells (Hurtado et al., 1997, J. Immunol. 158:2600-2609; Takahashi et al., 1999, J. Immunol. 162:5037-5040; Tran et al., 1995, J. Immunol. 155:1000-1009). 4-1BB stimulation preferentially activates CD8 T cells in vitro, amplifies CTL responses in vivo, and improves survival of activated CTLs (Shuford et al., 1997, J. Exp. Med. 186:47-55). 4-1BB is a candidate molecule that can promote long-term ex vivo growth of CD8 T cells. The initial growth rate of CD8 T cells stimulated with either CD3/28 beads or K32/4-1BBL aAPCs coated with anti-CD3 and CD28 Ab (K32/4-1BBL CD3/28) was equivalent. However, upon restimulation, only CD8 T cells activated with K32/4-1BBL CD3/28 aAPCs continued to expand. This ability to expand correlated with upregulation of the cell survival gene Bcl-xL and the cytokine IL-2. In the absence of these genes being induced, a large percentage of the cultures became Annexin V positive, an early sign of apoptosis (Maus et al., 2002, Nature Biotechnol. 20:143-148). "Crosstalk" between the cell based aAPCs and T cells was observed (Thomas et al., 2002, Clin. Immunol. 105:259-272).

Transduction of K562 cells with CD64 was accomplished as follows: K562 cells were transduced with a lentiviral vector expressing CD64 (SEQ ID NO:2) according to the methods described herein. High expressors were sorted and single clones were screened for CD64 expression. One clone was selected was further characterization (FIG. 14).

The binding capacity of K562 cells expressing CD64 (K64 cells) was evaluated as follows. One million K64 cells were loaded with 0.5-50 μl of IgG2a-FITC-labeled antibodies for 1 hour at 4° C., then washed once and fixed. Using the known antibody concentration (50 μg/ml), a known FITC/protein ratio (3.5) and Immuno-Brite (Beckman Coulter) beads, the amount of antibody bound to the K64 cells was calculated to be between about 2000 and 6000 antibodies bound to each cell (FIG. 15).

To evaluate the ability of K64 cells to load antibody and stimulate T cells, K64 and K32 cells were irradiated at 100 Gy, and loaded with 1 μg/ml of anti-CD3/anti-CD28 mixture per $10^6$ cells in the protein-free PFHM II media (Gibco/Invitrogen, Carlsbad, Calif.) and rotated at 4° C. for 1 hour. The cells were then washed three times with the same protein free media, resuspended in the same media, and added to CD4 T-cells at a ratio of 2:1. T-cells were resuspended in RPMI+ 10% HSAB at a concentration of $10^6$ cells per milliliter. As a control K64 and K32 cells were also loaded using the conventional method (10 minutes at room temperature without washes), and then mixed with CD4 T-cells.

As illustrated in FIG. 16, when K64 cells are compared to K32 cells, K64 cells loaded with anti-CD3/CD28 antibodies and washed three times to remove excess, unbound antibody are still capable of efficiently stimulating T-cells. Specifically, as depicted in FIG. 16, resting CD4 T cells have mean cell volume of ~140 fl. The disappearance of this population of cells indicates that the CD4 T cells have become activated. Thus, the aAPC cells of the present invention can be used in in vivo applications, as described elsewhere herein because they are capable of initiating T cell stimulation and proliferation without the presence of excess antibody that could result in a HAMA (human anti-mouse antibody) response if monoclonal antibodies are used in an in vivo application of the present invention.

Moreover, as demonstrated in FIG. 17, much less antibody is required to optimally load K64 cells, but washing K64 cells to prevent a HAMA reaction when administered to a mammal has minimal if any effect on the ability of an aAPC to stimulate a T cell. K64 cells were irradiated at 100 Gy, and loaded with either 1, ¼, ¹⁄₁₆, ¹⁄₆₄ or ¹⁄₂₅₆ mg/ml of anti-CD3/antiCD28 mixture per $10^6$ cells in duplicate in protein-free PFHM II media (Gibco/Invitrogen, Carlsbad, Calif.) and rotated for 1 hour at 4° C. One set of cells were washed three times with PFHM II and resuspended in the same media. The other set of cells were not washed. Both sets of K64 cells were added to CFSE labeled CD4 and CD8 T cells at a ratio 2:1. T-cells were resuspended in RPMI+10% HSAB, $10^6$/ml, as described above. As a control K64 and K32 cells were also loaded using conventional method (10 minutes at room temperature without washes), and then mixed with CD4 T-cells. CFSE dilution was measured by flow cytometry.

As illustrated in FIG. 17, three washes to remove excess antibody has little effect of aAPC comprising CD64 to stimulate both CD4 and CD8 cells.

Example 11

Expansion and Functional Characterization of Tregs

Naturally occurring CD25+CD4+ suppressor cells (Tregs) cells play an active part in establishing and maintaining immunological unresponsiveness to self constituents (i.e., immunological self tolerance) and negative control of various immune responses to non-self antigens. There are a paucity of reliable markers for defining Tregs, but naturally occurring CD25+CD4+ Tregs are the most widely studied because accumulating evidence indicates that this population plays a crucial role in the maintenance of immunological self tolerance and negative control of pathological as well as physiological immune responses. Their natural presence in the immune system as a phenotypically distinct population makes them a good target for designing ways to treat or prevent immunological diseases and to control pathological as well as physiological immune responses. However, little, if any methods exist to expand and manipulate this population of cells.

In order to induce the stimulation and proliferation and investigate the functions of aAPC contacted Treg cells, the following experiments were performed.

Peripheral blood lymphocytes were labeled with anti-CD4 and anti-CD25 antibody and the top 1% expressing CD25+ cells were isolated by cell sorting. These cells were stimulated with either anti-CD3 and CD28 antibody coated beads or K32 cells loaded with anti-CD3 and CD28 antibody. Cell expansion was measured by culturing the T cells in the presence of 3000 U/ml of IL-2 and maintaining the T cell concentration between 0.8 and 2 million cells per milliliter. Cells were counted on Coulter Counter IIE every two to three days. As illustrated in FIG. 18, aAPC stimulation of Treg populations resulted in a greater increase in the number of cells when compared to bead stimulation. In addition, greater numbers of Treg cells are produced more quickly than with conventional means, such as beads.

To evaluate the functionality of Treg cells stimulated by aAPCs, CD4 and CD25 positive and CD4 CD25 negative cells were expanded for 17 days using K32 cells loaded with anti-CD3 and CD28 Ab and 3000 U/ml of IL-2. These cells were mixed with resting, CFSE stained cells from the same donor at a 1:4 ratio (1 expanded cell for every 4 resting cells). This mixture was placed on allogenic dendritic cells and CFSE dilution was measured by flow cytometry. As illustrated in FIG. 19, Treg cells expanded with aAPCs suppress an allogeneic mixed lymphocyte reaction and the expanded CD4-positive-CD25-positive suppressed T cell expansion whereas the CD25 negative population did not.

A similar experiment was performed using aAPCs expressing CD32 (K32 cells) expressing OX40L. As illustrated in FIG. 20, CD4+CD25+ Treg cells are rendered non suppressive after such treatment with aAPCs.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of expanding a population of CD25+CD4+ Treg cells, the method comprising:

contacting said population with: (i) an artificial antigen presenting cell (aAPC) comprising a K562 cell, wherein said aAPC comprises CD64 on its surface loaded with an anti-CD3 antibody and CD86, wherein said CD64 is expressed from an exogenous expression vector; and (ii) IL-2, wherein binding of said anti-CD3 antibody and said CD86 with said Treg cells induces proliferation of said Treg cells, thereby expanding said population of CD25+CD4+ Treg cells.

2. The method of claim 1, wherein said IL-2 is expressed from an exogenous expression vector, wherein said vector is in said aAPC.

* * * * *

SEQUENCE LISTING

<160> NUMBER OF SEQ ID NOS: 22

<210> SEQ ID NO 1
<211> LENGTH: 9
<212> TYPE: PRT
<213> ORGANISM: Influenza virus

<400> SEQUENCE: 1

Gly Ile Leu Gly Phe Val Phe Thr Leu
1               5

<210> SEQ ID NO 2
<211> LENGTH: 2230
<212> TYPE: DNA
<213> ORGANISM: Homo sapiens

<400> SEQUENCE: 2

```
cttggagaca acatgtggtt cttgacaact ctgctccttt gggttccagt tgatgggcaa      60
gtggacacca caaaggcagt gatcactttg cagcctccat gggtcagcgt gttccaagag     120
gaaaccgtaa ccttgcattg tgaggtgctc catctgcctg ggagcagctc tacacagtgg     180
tttctcaatg gcacagccac tcagacctcg accccagct acagaatcac ctctgccagt     240
gtcaatgaca gtggtgaata caggtgccag agaggtctct cagggcgaag tgaccccata     300
cagctggaaa tccacagagg ctggctacta ctgcaggtct ccagcagagt cttcacggaa     360
ggagaacctc tggccttgag gtgtcatgcg tggaaggata agctggtgta caatgtgctt     420
tactatcgaa atggcaaagc cttaagtttt ttccactgga attctaacct caccattctg     480
aaaaccaaca taagtcacaa tggcacctac cattgctcag gcatgggaaa gcatcgctac     540
acatcagcag gaatatctgt cactgtgaaa gagctatttc cagctccagt gctgaatgca     600
tctgtgacat ccccactcct ggagggaat ctggtcaccc tgagctgtga aacaaagttg     660
ctcttgcaga ggcctggttt gcagctttac ttctcctcct acatgggcag caagacccty     720
cgaggcagga acacatcctc tgaataccaa atactaactg ctagaagaga agactctggg     780
ttatactggt gcgaggctgc cacagaggat ggaaatgtcc ttaagcgcag ccctgagttg     840
gagcttcaag tgcttggcct ccagttacca actcctgtct ggtttcatgt cctttctat     900
```

```
ctggcagtgg gaataatgtt tttagtgaac actgttctct gggtgacaat acgtaaagaa    960
ctgaaaagaa agaaaaagtg ggatttagaa atctctttgg attctggtca tgagaagaag   1020
gtaatttcca gccttcaaga agacagacat ttagaagaag agctgaaatg tcaggaacaa   1080
aaagaagaac agctgcagga aggggtgcac cggaaggagc cccagggggc cacgtagcag   1140
cggctcagtg ggtggccatc gatctggacc gtcccctgcc cacttgctcc ccgtgagcac   1200
tgcgtacaaa catccaaaag ttcaacaaca ccagaactgt gtgtctcatg gtatgtaact   1260
cttaaagcaa ataaatgaac tgacttcaac tgggatacat ttggaaatgt ggtcatcaaa   1320
gatgacttga aatgaggcct actctaaaga attcttgaaa aacttacaag tcaagcctag   1380
cctgataatc ctattacata gtttgaaaaa tagtatttta tttctcagaa caaggtaaaa   1440
aggtgagtgg gtgcatatgt acagaagatt aagacagaga acagacaga aagagacaca    1500
cacacagcca ggagtgggta gatttcaggg agacaagagg gaatagtata gacaataagg   1560
aaggaaatag tacttacaaa tgactcctaa gggactgtga gactgagagg gctcacgcct   1620
ctgtgttcag gatacttagt tcatggcttt tctctttgac tttactaaaa gagaatgtct   1680
ccatacgcgt tctaggcata caggggggta actcatgatg agaaatggat gtgttattct   1740
tgccctctct tttgaggctc tctcataacc cctctatttc tagagacaac aaaaatgctg   1800
ccagtcctag gcccctgccc tgtaggaagg cagaatgtaa ctgttctgtt tgtttaacga   1860
ttaagtccaa atctccaagt gcggcactgc aaagagacgc ttcaagtggg gagaagcggc   1920
gataccatag agtccagatc ttgcctccag agatttgctt taccttcctg attttctggt   1980
tactaattag cttcaggata cgctgctctc atacttgggc tgtagtttgg agacaaaata   2040
ttttcctgcc actgtgtaac atagctgagg taaaaactga actatgtaaa tgactctact   2100
aaaagtttag ggaaaaaaaa caggaggagt atgacacaaa aaaaaaaaaa aaaaaaaaa    2160
aaaaaaaaaa aaaaaaaaaa aaaaaaaaaa aaaaaaaaaa aaaaaaaaaa aaaaaaaaaa   2220
aaaaaaaaaa                                                          2230
```

<210> SEQ ID NO 3
<211> LENGTH: 9
<212> TYPE: PRT
<213> ORGANISM: Human immunodeficiency virus

<400> SEQUENCE: 3

Ile Leu Lys Glu Pro Val His Gly Val
1               5

<210> SEQ ID NO 4
<211> LENGTH: 9
<212> TYPE: PRT
<213> ORGANISM: Epstein Barr Virus

<400> SEQUENCE: 4

Gly Leu Cys Thr Leu Val Ala Met Leu
1               5

<210> SEQ ID NO 5
<211> LENGTH: 9
<212> TYPE: PRT
<213> ORGANISM: Human cytomegalovirus

<400> SEQUENCE: 5

Asn Leu Val Pro Met Val Ala Thr Val
1               5

<210> SEQ ID NO 6
<211> LENGTH: 9
<212> TYPE: PRT
<213> ORGANISM: Human immunodeficiency virus

<400> SEQUENCE: 6

Ser Leu Tyr Asn Thr Val Ala Thr Leu
1               5

<210> SEQ ID NO 7
<211> LENGTH: 9
<212> TYPE: PRT
<213> ORGANISM: Human T-cell lymphotropic virus

<400> SEQUENCE: 7

Leu Leu Phe Gly Tyr Pro Val Tyr Val
1               5

<210> SEQ ID NO 8
<211> LENGTH: 1019
<212> TYPE: DNA
<213> ORGANISM: Homo sapiens

<400> SEQUENCE: 8

```
tgatgggaat cctgtcattc ttacctgtcc ttgccactga gagtgactgg gctgactgca      60
agtcccccca gccttggggt catatgcttc tgtggacagc tgtgctattc ctggctcctg     120
ttgctgggac acctgcagct cccccaaagg ctgtgctgaa actcgagccc cagtggatca     180
acgtgctcca agaggactct gtgactctga catgccgggg gactcacagc cctgagagcg     240
actccattca gtggttccac aatgggaatc tcattcccac ccacacgcag cccagctaca     300
ggttcaaggc caacaacaat gacagcgggg agtacacgtg ccagactggc cagaccagcc     360
tcagcgaccc tgtgcatctg actgtgcttt ctgagtggct ggtgctccag acccctcacc     420
tggagttcca ggagggagaa accatcgtgc tgaggtgcca cagctggaag acaagcctc      480
tggtcaaggt cacattcttc cagaatggaa aatccaagaa attttcccgt tcggatccca     540
acttctccat cccacaagca accacagtc acagtggtga ttaccactgc acaggaaaca     600
taggctacac gctgtactca tccaagcctg tgaccatcac tgtccaagct cccagctctt     660
caccgatggg gatcattgtg ctgtggtca ctggattgc tgtagcggcc attgttgctg       720
ctgtagtggc cttgatctac tgcaggaaaa agcggatttc agccaattcc actgatcctg     780
tgaaggctgc ccaatttgag atgctttcct gcagccacct ggacgtcaaa tgattgccat     840
cagaaagaga caacctgaag aaaccaacaa tgactatgaa acagctgacg gcggctacat     900
gactctgaac cccagggcac ctactgacga tgataaaaac atctacctga ctcttcctcc     960
caacgaccat gtcaacagta ataactaaag agtaacgtta tgccatgtgg tcatctaga    1019
```

<210> SEQ ID NO 9
<211> LENGTH: 1589
<212> TYPE: DNA
<213> ORGANISM: Homo sapiens

<400> SEQUENCE: 9

```
gaattcctct ggtcctcatc caggtgcgcg ggaagcaggt gcccaggaga gagggataa       60
tgaagattcc atgctgatga tcccaaagat tgaacctgca gaccaagcgc aaagtagaaa    120
ctgaaagtac actgctggcg gatcctacgg aagttatgga aaaggcaaag cgcagagcca    180
cgccgtagtg tgtgccgccc cccttgggat ggatgaaact gcagtcgcgg cgtgggtaag    240
```

```
aggaaccagc tgcagagatc accctgccca acacagactc ggcaactccg cggaagacca      300
gggtcctggg agtgactatg gcggtgaga  gcttgctcct gctccagttg cggtcatcat      360
gactacgccc gcctcccgca gaccatgttc catgtttctt ttaggtatat ctttggactt      420
cctcccctga tccttgttct gttgccagta gcatcatctg attgtgatat tgaaggtaaa      480
gatggcaaac aatatgagag tgttctaatg gtcagcatcg atcaattatt ggacagcatg      540
aaagaaattg gtagcaattg cctgaataat gaatttaact tttttaaaag acatatctgt      600
gatgctaata aggaaggtat gttttttattc cgtgctgctc gcaagttgag gcaatttctt      660
aaaatgaata gcactggtga ttttgatctc cacttattaa aagtttcaga aggcacaaca      720
atactgttga actgcactgg ccaggttaaa ggaagaaaac cagctgccct gggtgaagcc      780
caaccaacaa agagtttgga agaaaataaa tctttaaagg aacagaaaaa actgaatgac      840
ttgtgtttcc taagagagact attacaagag ataaaaactt gttggaataa aattttgatg      900
ggcactaaag aacactgaaa aatatggagt ggcaatatag aaacacgaac tttagctgca      960
tcctccaaga atctatctgc ttatgcagtt tttcagagtg gaatgcttcc tagaagttac     1020
tgaatgcacc atggtcaaaa cggattaggg catttgagaa atgcatattg tattactaga     1080
agatgaatac aaacaatgga aactgaatgc tccagtcaac aaactatttc ttatatatgt     1140
gaacatttat caatcagtat aattctgtac tgattttgt  aagacaatcc atgtaaggta     1200
tcagttgcaa taatacttct caaacctgtt taaatatttc aagacattaa atctatgaag     1260
tatataatgg tttcaaagat tcaaaattga cattgcttta ctgtcaaaat aattttatgg     1320
ctcactatga atctattata ctgtattaag agtgaaaatt gtcttcttct gtgctggaga     1380
tgttttagag ttaacaatga tatatggata atgccggtga gaataagaga gtcataaaacc    1440 ttaagtaagc aacagcataa caaggtccaa gatacctaaa agagatttca agagatttaa     1500
ttaatcatga atgtgtaaca cagtgccttc aataaatggt atagcaaatg ttttgacatg     1560
aaaaaaggac aatttcaaaa aaataaaat                                       1589
```

<210> SEQ ID NO 10
<211> LENGTH: 1969
<212> TYPE: DNA
<213> ORGANISM: Homo sapiens

<400> SEQUENCE: 10

```
gactccgggt ggcaggcgcc cgggggaatc ccagctgact cgctcactgc cttcgaagtc       60
cggcgccccc cggagggaa  ctgggtggcc gcaccctccc ggctgcggtg gctgtcgccc      120
cccaccctgc agccaggact cgatggaggt acagagctcg gcttctttgc cttgggaggg      180
gagtggtggt ggttgaaagg gcgatggaat tttccccgaa agcctacgcc cagggcccct      240
cccagctcca gcgttaccct ccggtctatc ctactggccg agctgccccg ccttctcatg      300
gggaaaactt agccgcaact tcaattttg  gttttttcctt taatgacact tctgaggctc      360
tcctagccat cctcccgctt ccggaggagc gcagatcgca ggtccctttg cccctggcgt      420
gcgactccct actgcgctgc gctcttacgg cgttccaggc tgctggctag cgcaaggcgg      480
gccgggcacc ccgcgctccg ctgggagggt gagggacgcg cgtctggcgg ccccagccaa      540
gctgcgggtt tctgagaaga cgctgtcccg cagccctgag ggctgagttc tgcacccagt      600
caagctcagg aaggccaaga aaagaatcca ttccaatata tggccatgtg gctctttgga      660
gcaatgttcc atcatgttcc atgctgctga cgtcacatgg agcacagaaa tcaatgttag      720
```

```
cagatagcca gcccatacaa gatcgtattg tattgtagga ggcatcgtgg atggatggct      780
gctggaaacc ccttgccata gccagctctt cttcaatact taaggattta ccgtggcttc      840
gagtaatgag aatttcgaaa ccacatttga gaagtatttc catccagtgc tacttgtgtt      900
tacttctaaa cagtcatttt ctaactgaag ctggcattca tgtcttcatt ttgggctgtt      960
tcagtgcagg gcttcctaaa acagaagcca actgggtgaa tgtaataagt gatttgaaaa     1020
aaattgaaga tcttattcaa tctatgcata ttgatgctac tttatatacg gaaagtgatg     1080
ttcaccccag ttgcaaagta acagcaatga agtgctttct cttggagtta caagttatt      1140 cacttgagtc cggagatgca agtattcatg atacagtaga aaatctgatc atcctagcaa     1200
acaacagttt gtcttctaat gggaatgtaa cagaatctgg atgcaaagaa tgtgaggaac     1260
tggaggaaaa aaatattaaa gaattttgc agagttttgt acatattgtc caatgttca      1320 tcaacacttc ttgattgcaa ttgattcttt ttaaagtgtt tctgttatta acaaacatca     1380
ctctgctgct tagacataac aaaacactcg gcatttcaaa tgtgctgtca aaacaagttt     1440
ttctgtcaag aagatgatca gaccttggat cagatgaact cttagaaatg aaggcagaaa     1500
aatgtcattg agtaatatag tgactatgaa cttctctcag acttacttta ctcattttt     1560 taatttatta ttgaaattgt acatatttgt ggaataatgt aaaatgttga ataaaaatat     1620
gtacaagtgt tgtttttaa gttgcactga tattttacct cttattgcaa aatagcattt     1680
gtttaagggt gatagtcaaa ttatgtattg gtggggctgg gtaccaatgc tgcaggtcaa     1740
cagctatgct ggtaggctcc tgccagtgtg gaaccactga ctactggctc tcattgactt     1800
ccttactaag catagcaaac agaggaagaa tttgttatca gtaagaaaaa gaagaactat     1860
atgtgaatcc tcttctttat actgtaattt agttattgat gtataaagca actgttatga     1920
aataaagaaa ttgcaataac tggcaaaaaa aaaaaaaaa aaaaaaaa                   1969

<210> SEQ ID NO 11
<211> LENGTH: 611
<212> TYPE: DNA
<213> ORGANISM: Homo sapiens

<400> SEQUENCE: 11
gtgaaaacga gaccaaggtc tagctctact gttggtactt atgagatcca gtcctggcaa       60
catggagagg attgtcatct gtctgatggt catcttcttg gggacactgg tccacaaatc      120
aagctcccaa ggtcaagatc gccacatgat tagaatgcgt caacttatag atattgttga      180
tcagctgaaa aattatgtga atgacttggt ccctgaattt ctgccagctc cagaagatgt      240
agagacaaac tgtgagtggt cagctttttc ctgctttcag aaggcccaac taaagtcagc      300
aaatacagga acaatgaaa ggataatcaa tgtatcaatt aaaaagctga gaggaaaacc      360
accttccaca aatgcaggga gaagacagaa acacagacta acatgcccctt catgtgattc      420 ttatgagaaa aaaccaccca agaattcct agaaagattc aaatcacttc tccaaaagat      480
gattcatcag catctgtcct ctagaacaca cggaagtgaa gattcctgag gatctaactt      540
gcagttggac actatgttac atactctaat atagtagtga aagtcatttc tttgtattcc      600
aagtggagga g                                                          611

<210> SEQ ID NO 12
<211> LENGTH: 1048
<212> TYPE: DNA
<213> ORGANISM: Homo sapiens

<400> SEQUENCE: 12
```

-continued

```
ggccctggga cctttgccta ttttctgatt gataggcttt gttttgtctt tacctccttc      60
tttctgggga aaacttcagt tttatcgcac gttcccettt tccatatctt catcttccct     120
ctacccagat tgtgaagatg gaaagggtcc aaccectgga agagaatgtg ggaaatgcag     180
ccaggccaag attcgagagg aacaagctat tgctggtggc ctctgtaatt cagggactgg     240
ggctgctcct gtgcttcacc tacatctgcc tgcacttctc tgctcttcag gtatcacatc     300
ggtatcctcg aattcaaagt atcaaagtac aatttaccga atataagaag agaaaggtt     360 tcatcctcac ttcccaaaag gaggatgaaa tcatgaaggt gcagacaac tcagtcatca     420 tcaactgtga tgggttttat ctcatctccc tgaagggcta cttctcccag gaagtcaaca     480
ttagccttca ttaccagaag gatgaggagc ccctcttcca actgaagaag gtcaggtctg     540
tcaactcctt gatggtggcc tctctgactt acaaagacaa agtctacttg aatgtgacca     600
ctgacaatac ctccctggat gacttccatg tgaatggcgg agaactgatt cttatccatc     660
aaaatcctgg tgaattctgt gtcctttgag gggctgatgg caatatctaa aaccaggcac     720
cagcatgaac accaagctgg gggtggacag ggcatggatt cttcattgca agtgaaggag     780
cctcccagct cagccacgtg ggatgtgaca agaagcagat cctggccctc ccgccccac     840 ccctcaggga tatttaaaac ttatttata taccagttaa tcttatttat ccttatattt     900
tctaaattgc ctagccgtca caccccaaga ttgccttgag cctactaggc acctttgtga     960
gaaagaaaaa atagatgcct cttcttcaag atgcattgtt tctattggtc aggcaattgt    1020
cataataaac ttatgtcatt gaaaacgg                                       1048

<210> SEQ ID NO 13
<211> LENGTH: 1645
<212> TYPE: DNA
<213> ORGANISM: Homo sapiens

<400> SEQUENCE: 13
agtctctcgt catggaatac gcctctgacg cttcactgga ccccgaagcc ccgtggcctc      60 ccgcgcccg cgctcgcgcc tgccgcgtac tgccttgggc cctggtcgcg gggctgctgc     120
tgctgctgct gctcgctgcc gctgcgccg tcttcctcgc ctgcccctgg gccgtgtccg     180
gggctcgcgc ctcgcccggc tccgcggcca gcccgagact ccgcgagggt cccgagcttt     240
cgcccgacga tcccgccggc ctcttggacc tgcggcaggg catgtttgcg cagctggtgg     300
cccaaaatgt tctgctgatc gatgggcccc tgagctggta cagtgaccca ggcctggcag     360
gcgtgtccct gacgggggc ctgagctaca agaggacac gaaggagctg gtggtggcca     420
aggctggagt ctactatgtc ttctttcaac tagagctgcg gcgcgtggtg gccggcgagg     480
gctcaggctc cgtttcactt gcgctgcacc tgcagccact gcgctctgct gctggggccg     540 ccgcctggc tttgaccgtg gacctgccac cgcctcctc cgaggctcgg aactcggcct     600 tcggttttcca gggccgcttg ctgcacctga gtgccggcca gcgcctgggc gtccatcttc     660
acactgaggc cagggcacgc catgcctggc agcttaccca gggcgccaca gtctgggac     720 tcttccgggt gaccccgaa atcccagccg gactcccttc accgaggtcg gaataacgcc     780
cagcctgggt gcagcccacc tggacagagt ccgaatccta ctccatcctt catggagacc     840
cctggtgctg ggtccctgct gctttctcta cctcaagggg cttggcaggg gtccctgctg     900
ctgacctccc cttgaggacc ctcctcaccc actccttccc caagttggac cttgatattt     960
attctgagcc tgagctcaga taatatatta tatatattat atatatatat atatttctat    1020
```

| | |
|---|---:|
| ttaaagagga tcctgagttt gtgaatggac ttttttagag gagttgtttt ggggggggggg | 1080 |
| tcttcgacat tgccgaggct ggtcttgaac tcctggactt agacgatcct cctgcctcag | 1140 |
| cctcccaagc aactgggatt catcctttct attaattcat tgtacttatt tgcctatttg | 1200 |
| tgtgtattga gcatctgtaa tgtgccagca ttgtgcccag gctaggggggc tatagaaaca | 1260 |
| tctagaaata gactgaaaga aaatctgagt tatggtaata cgtgaggaat ttaaagactc | 1320 |
| atccccagcc tccacctcct gtgtgatact tgggggctag cttttttctt tctttcttttt | 1380 |
| ttttgagatg gtcttgttct gtcaaccagg ctagaatgca gcggtgcaat catgagtcaa | 1440 |
| tgcagcctcc agcctcgacc tcccgaggct caggtgatcc tcccatctca gcctctcgag | 1500 |
| tagctgggac cacagttgtg tgccaccaca cttggctaac ttttttaattt ttttgcggag | 1560 |
| acggtattgc tatgttgcca aggttgttta catgccagta caatttataa taaacactca | 1620 |
| tttttcctca aaaaaaaaaa aaaaa | 1645 |

<210> SEQ ID NO 14
<211> LENGTH: 2824
<212> TYPE: DNA
<213> ORGANISM: Homo sapiens

<400> SEQUENCE: 14

| | |
|---|---:|
| aagtaacaga agttagaagg ggaaatgtcg cctctctgaa gattacccaa agaaaaagtg | 60 |
| atttgtcatt gctttataga ctgtaagaag agaacatctc agaagtggag tcttaccctg | 120 |
| aaatcaaagg atttaaagaa aaagtggaat ttttcttcag caagctgtga aactaaatcc | 180 |
| acaacctttg gagacccagg aacaccctcc aatctctgtg tgttttgtaa acatcactgg | 240 |
| agggtcttct acgtgagcaa ttggattgtc atcagccctg cctgttttgc acctgggaag | 300 |
| tgccctggtc ttacttgggt ccaaattgtt ggctttcact tttgacccta agcatctgaa | 360 |
| gccatgggcc acacacggag gcagggaaca tcaccatcca agtgtccata cctcaatttc | 420 |
| tttcagctct tggtgctggc tggtctttct cacttctgtt caggtgttat ccacgtgacc | 480 |
| aaggaagtga agaagtggc aacgctgtcc tgtggtcaca atgtttctgt tgaagagctg | 540 |
| gcacaaactc gcatctactg gcaaaaggag aagaaaatgg tgctgactat gatgtctggg | 600 |
| gacatgaata tatggcccga gtacaagaac cggaccatct ttgatatcac taataacctc | 660 |
| tccattgtga tcctggctct cgcgcccatct gacgagggca catacgagtg tgttgttctg | 720 |
| aagtatgaaa aagacgcttt caagcgggaa caccctggctg aagtgacgtt atcagtcaaa | 780 |
| gctgacttcc ctacacctag tatatctgac tttgaaaattc caacttctaa tattagaagg | 840 |
| ataaatttgct caacctctgg aggttttcca gagcctcacc tctcctggtt ggaaaatgga | 900 |
| gaagaattaa atgccatcaa cacaacagtt cccaagatcc tgaaactga gctctatgct | 960 |
| gttagcagca aactggattt caatatgaca accaaccaca gcttcatgtg tctcatcaag | 1020 |
| tatgacatt taagagtgaa tcagaccttc aactggaata caaccaagca agagcatttt | 1080 |
| cctgataacc tgctcccatc ctgggccatt accttaatct cagtaaatgg aattttttgtg | 1140 |
| atatgctgcc tgacctactg ctttgcccca agatgcagag agagaaggag gaatgagaga | 1200 |
| ttgagaaggg aaagtgtacg ccctgtataa cagtgtccgc agaagcaagg ggctgaaaag | 1260 |
| atctgaaggt ctcacctcca tttgcaattg acctcttctg ggaacttcct cagatggaca | 1320 |
| agattacccc accttgccct ttacgtatct gctcttaggt gcttcttcac ttcagttgct | 1380 |
| ttgcaggaag tgtctagagg aatatggtgg gcacagaagt agctctggtg accttgatca | 1440 |
| aggggttttg aaatgcagaa ttcttgagtt ctggaaggga ctttagagaa taccagtgtt | 1500 |

```
attaatgaca aaggcactga ggcccaggga ggtgacccga attataaagg ccagcgccag    1560
aacccagatt tcctaactct ggtgctcttt ccctttatca gtttgactgt ggcctgttaa    1620
ctggtatata catatatatg tcaggcaaag tgctgctgga agtagaattt gtccaataac    1680
aggtcaactt cagagactat ctgatttcct aatgtcagag tagaagattt tatgctgctg    1740
tttacaaaag cccaatgtaa tgcataggaa gtatggcatg aacatcttta ggagactaat    1800
ggaaatatta ttggtgttta cccagtattc cattttttc attgtgttct ctattgctgc     1860
tctctcactc ccccatgagg tacagcagaa aggagaacta tccaaaacta atttcctctg    1920
acatgtaaga cgaatgattt aggtacgtca aagcagtagt caaggaggaa agggatagtc    1980
caaagactta actggttcat attggactga taatctcttt aaatggcttt atgctagttt    2040
gacctcattt gtaaaatatt tatgagaaag ttctcattta aaatgagatc gttgtttaca    2100
gtgtatgtac taagcagtaa gctatcttca aatgtctaag gtagtaactt tccatagggc    2160
ctccttagat ccctaagatg gcttttctc cttggtattt ctgggtcttt ctgacatcag     2220
cagagaactg gaaagacata gccaactgct gttcatgtta ctcatgactc ctttctctaa    2280
aactgccttc cacaattcac tagaccagaa gtggacgcaa cttaagctgg gataatcaca    2340
ttatcatctg aaaatctgga gttgaacagc aaaagaagac aacatttctc aaatgcacat    2400
ctcatggcag ctaagccaca tggctgggat ttaaagcctt tagagccagc ccatggcttt    2460
agctacctca ctatgctgct tcacaaacct tgctcctgtg taaaactata ttctcagtgt    2520
agggcagaga ggtctaacac caacataagg tactagcagt gtttcccgta ttgacaggaa    2580
tacttaactc aataattctt ttcttttcca tttagtaaca gttgtgatga ctatgtttct    2640
attctaagta attcctgtat tctacagcag atactttgtc agcaatacta agggaagaaa    2700
caaagttgaa ccgtttcttt aataaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaa                                                                 2824

<210> SEQ ID NO 15
<211> LENGTH: 2410
<212> TYPE: DNA
<213> ORGANISM: Homo sapiens

<400> SEQUENCE: 15
gcttccgctg cccgccgggg aatccccgg gctggcgcgc agggaagttc ccgaacgcgc      60
gggcataaaa gggcagccgg cgcccgcgcg ccacagctct gcagctcgtg gcagcggcgc    120
agcgctccag ccatgtcgcg cggcctccag cttctgctcc tgagctgcgc ctacagcctg    180
gctcccgcga cgccggaggt gaaggtggct tgctccgaag atgtggactt gccctgcacc    240 gcccctggg atccgcaggt tccctacacg gtctcctggg tcaagttatt ggagggtggt    300
gaagagagga tggagacacc ccaggaagac cacctcaggg acagcactaa tcatcagaag    360
gggcaaaatg gttctttcga cgcccccaat gaaaggccct attccctgaa gatccgaaac    420
actaccagct gcaactcggg gacatacagg tgcactctgc aggacccgga tgggcagaga    480
aacctaagtg gcaaggtgat cttgagagtg acaggatgcc ctgcacagcg taaagaagag    540
acttttaaga aatacagagc ggagattgtc ctgctgctgg ctctggttat tttctactta    600
acactcatca ttttcactta taagtttgca cggctacaga gatcttccc agattttcct     660 aaagctggca tggaacgagc ttttctccca gttacctccc caaataagca tttagggcta    720
```

```
gtgactcctc acaagacaga actggtatga gcaggatttc tgcaggttct tcttcctgaa      780
gctgaggctc agggggtgtgc ctgtctgtta cactggagga gagaagaatg agcctacgct      840
gaagatggca tcctgtgaag tccttcacct cactgaaaac atctggaagg ggatcccacc      900
ccattttctg tgggcaggcc tcgaaaacca tcacatgacc acatagcatg aggccactgc      960
tgcttctcca tggccacctt ttcagcgatg tatgcagcta tctggtcaac ctcctggaca     1020
ttttttcagt catataaaag ctatggtgag atgcagctgg aaaagggtct tgggaaatat     1080
gaatgccccc agctggcccg tgacagactc ctgaggacag ctgtcctctt ctgcatcttg     1140
gggacatctc tttgaatttc ctgtgttttg ctgtaccagc ccagatgttt tacgtctggg     1200
agaaattgac agatcaagct gtgagacagt gggaaatatt tagcaataat ttcctggtgt     1260
gaaggtcctg ctattactaa ggagtaatct gtgtacaaaa aaataacaag tcgatgaact     1320
attccccagc agggtctttt catctgggaa agacatccat aaagaagcaa taagaagag      1380 tgccacattt atttttatat ctatatgtac ttgtcaaaga aggttgtgtt tttctgcttt     1440
tgaaatctgt atctgtagtg agatagcatt gtgaactgac aggcagcctg gacatagaga     1500
gggagaagaa gtcagagagg gtgacaagat agagagctat ttaatggccg gctggaaatg     1560
ctgggctgac ggtgcagtct gggtgctcgc ccacttgtcc cactatctgg gtgcatgatc     1620
ttgagcaagt tccttctggt gtctgctttc tccattgtaa accacaaggc tgttgcatgg     1680
gctaatgaag atcatatacg tgaaaattat ttgaaaacat ataaagcact atacagattc     1740
gaaactccat tgagtcatta tccttgctat gatgatggtg ttttggggat gagagggtgc     1800
tatccatttc tcatgttttc cattgtttga aacaagaag gttaccaaga agcctttcct      1860
gtagccttct gtaggaattc ttttggggaa gtgaggaagc caggtccacg gtctgttctt     1920
gaagcagtag cctaacacac tccaagatat ggacacacgg gagccgctgg cagaagggac     1980
ttcacgaagt gttgcatgga tgttttagcc attgttggct ttcccttatc aaacttgggc     2040
ccttcccttc ttggtttcca aaggcatttt attgcttgag ttatatgttc actgcccccc     2100
taatattagg gagtaaaacg gataccaagt tgatttagtg ttttttaccctc tgtcttggct     2160 ttcatgttat taaacgtatg catgtgaaga aagggtgttt ttctgtttta tattcaactc     2220
ataagacttt gggataggaa aaatgagtaa tggttactag gcttaatacc tgggtgatta     2280
cataatctgt acaacgaacc cccatgatgt aagtttacct atgtaacaaa cctgcactta     2340
tacccatgaa cttaaaatga aagttaaaaa taaaaaacat atacaaataa aaaaaaaaa      2400 aaaaaaaaa                                                             2410
```

<210> SEQ ID NO 16
<211> LENGTH: 2794
<212> TYPE: DNA
<213> ORGANISM: Homo sapiens

<400> SEQUENCE: 16

```
aggagcctta ggaggtacgg ggagctcgca aatactcctt ttggtttatt cttaccacct       60
tgcttctgtg ttccttggga atgctgctgt gcttatgcat ctggtctctt tttgagcta      120 cagtggacag gcatttgtga cagcactatg ggactgagta acattctctt tgtgatggcc     180
ttcctgctct ctggtgctgc tcctctgaag attcaagctt atttcaatga gactgcagac     240
ctgccatgcc aatttgcaaa ctctcaaaac caaagcctga gtgagctagt agtattttgg     300
caggaccagg aaaacttggt tctgaatgag gtatacttag gcaaagagaa atttgacagt     360
gttcattcca agtatatggg ccgcacaagt tttgattcgg acagttggac cctgagactt      420
```

```
cacaatcttc agatcaagga caagggcttg tatcaatgta tcatccatca caaaaagccc      480
acaggaatga ttcgcatcca ccagatgaat tctgaactgt cagtgcttgc taacttcagt      540
caacctgaaa tagtaccaat ttctaatata acagaaaatg tgtacataaa tttgacctgc      600
tcatctatac acggttaccc agaacctaag aagatgagtg ttttgctaag aaccaagaat      660
tcaactatcg agtatgatgg tattatgcag aaatctcaag ataatgtcac agaactgtac      720
gacgtttcca tcagcttgtc tgtttcattc cctgatgtta cgagcaatat gaccatcttc      780
tgtattctgg aaactgacaa gacgcggctt ttatcttcac ctttctctat agagcttgag      840
gaccctcagc ctcccccaga ccacattcct tggattacag ctgtacttcc aacagttatt      900
atatgtgtga tggttttctg tctaattcta tggaaatgga agaagaagaa gcggcctcgc      960
aactcttata aatgtggaac caacacaatg gagagggaag agagtgaaca gaccaagaaa     1020
agagaaaaaa tccatatacc tgaaagatct gatgaagccc agcgtgtttt taaaagttcg     1080
aagacatctt catgcgacaa aagtgataca tgttttaat taaagagtaa agcccataca      1140
agtattcatt ttttctaccc tttcctttgt aagttcctgg caaccttttt tgatttcttc     1200
cagaaggcaa aaagacatta ccatgagtaa taaggggggct ccaggactcc ctctaagtgg     1260
aatagcctcc ctgtaactcc agctctgctc cgtatgccaa gaggagactt taattctctt     1320
actgcttctt ttcacttcag agcacactta tgggccaagc ccagcttaat ggctcatgac     1380
ctggaaataa aatttaggac caatacctcc tccagatcag attcttctct taatttcata     1440
gattgtgttt ttttttaaat agacctctca atttctggaa aactgccttt tatctgccca     1500
gaattctaag ctggtgcccc actgaatctt gtgtacctgt gactaaacaa ctacctcctc     1560
agtctgggtg ggacttatgt atttatgacc ttatagtgtt aatatcttga aacatagaga     1620
tctatgtact gtaatagtgt gattactatg ctctagagaa aagtctaccc ctgctaagga     1680
gttctcatcc ctctgtcagg gtcagtaagg aaaacggtgg cctagggtac aggcaacaat     1740
gagcagacca acctaaattt ggggaaatta ggagaggcag agatagaacc tggagccact     1800
tctatctggg ctgttgctaa tattgaggag gcttgcccca cccaacaagc catagtggag     1860
agaactgaat aaacaggaaa atgccagagc ttgtgaaccc tgtttctctt gaagaactga     1920
ctagtgagat ggcctgggga agctgtgaaa gaaccaaaag agatcacaat actcaaagaa     1980
gagagagaga gaaaaagag agatcttgat ccacagaaat acatgaaatg tctggtctgt     2040 ccacccatc aacaagtctt gaaacaagca acagatggat agtctgtcca atggacata      2100 agacagacag cagtttccct ggtggtcagg gaggggtttt ggtgataccc aagttattgg     2160
gatgtcatct tcctggaagc agagctgggg agggagagcc atcaccttga taatgggatg     2220
aatggaagga ggcttaggac tttccactcc tggctgagag aggaagagct gcaacggaat     2280
taggaagacc aagacacaga tcacccgggg cttacttagc ctacagatgt cctacgggaa     2340
cgtgggctgg cccagcatag ggctagcaaa tttgagttgg atgattgttt ttgctcaagg     2400
caaccagagg aaacttgcat acagagacag atatactggg agaaatgact ttgaaaacct     2460
ggctctaagg tgggatcact aagggatggg gcagtctctg cccaaacata aagagaactc     2520
tggggagcct gagccacaaa aatgttcctt tattttatgt aaaccctcaa gggttataga     2580
ctgccatgct agacaagctt gtccatgtaa tattcccatg ttttaccct gcccctgcct      2640 tgattagact cctagcacct ggctagtttc taacatgttt tgtgcagcac agtttttaat     2700
aaatgcttgt tacattcaaa aaaaaaaaaa aaaaaaaaaa aaaaaaaaaa aaaaaaaaaa     2760
```

-continued

| | |
|---|---|
| aaaaaaaaaa aaaaaaaaaa aaaaaaaaaa aaaa | 2794 |

<210> SEQ ID NO 17
<211> LENGTH: 3239
<212> TYPE: DNA
<213> ORGANISM: Homo sapiens

<400> SEQUENCE: 17

| | |
|---|---|
| gcgggagcgc agttagagcc gatctcccgc gccccgaggt tgctcctctc cgaggtctcc | 60 |
| cgcggcccaa gttctccgcg ccccgaggtc tccgcgcccc gaggtctccg cggcccgagg | 120 |
| tctccgcccg caccatgcgg ctgggcagtc ctggactgct cttcctgctc ttcagcagcc | 180 |
| ttcgagctga tactcaggag aaggaagtca gagcgatggt aggcagcgac gtggagctca | 240 |
| gctgcgcttg ccctgaagga agccgttttg atttaaatga tgtttacgta tattggcaaa | 300 |
| ccagtgagtc gaaaaccgtg gtgacctacc acatcccaca gaacagctcc ttggaaaacg | 360 |
| tggacagccg ctaccggaac cgagccctga tgtcaccggc cggcatgctg cggggcgact | 420 |
| tctccctgcg cttgttcaac gtcacccccc aggacgagca gaagtttcac tgcctggtgt | 480 |
| tgagccaatc cctgggattc caggaggttt gagcgttga ggttacactg catgtggcag | 540 |
| caaacttcag cgtgcccgtc gtcagcgccc ccacagccc ctcccaggat gagctcacct | 600 |
| tcacgtgtac atccataaac ggctacccca ggcccaacgt gtactggatc aataagacgg | 660 |
| acaacagcct gctggaccag gctctgcaga tgacaccgt cttcttgaac atgcggggct | 720 |
| tgtatgacgt ggtcagcgtg ctgaggatcg cacggacccc cagcgtgaac attggctgct | 780 |
| gcatagagaa cgtgcttctg cagcagaacc tgactgtcgg cagccagaca ggaaatgaca | 840 |
| tcggagagag agacaagatc acagagaatc cagtcagtac cggcgagaaa aacgcggcca | 900 |
| cgtggagcat cctggctgtc ctgtgcctgc ttgtggtcgt ggcgtggc ataggctggg | 960 |
| tgtgcaggga ccgatgcctc caacacagct atgcaggtgc ctgggctgtg agtccggaga | 1020 |
| cagagctcac tggccacgtt tgaccggagc tcaccgccca gagcgtggac agggcttccg | 1080 |
| tgagacgcca ccgtgagagg ccaggtggca gcttgagcat ggactcccag actgcagggg | 1140 |
| agcacttggg gcagcccca gaaggaccac tgctggatcc cagggagaac ctgctggcgt | 1200 |
| tggctgtgat cctggaatga ggccctttca aaagcgtcat ccacaccaaa ggcaaatgtc | 1260 |
| cccaagtgag tgggctcccc gctgtcactg ccagtcaccc acaggaaggg actggtgatg | 1320 |
| ggctgtctct acccggagcg tgcgggattc agcaccaggc tcttcccagt accccagacc | 1380 |
| cactgtgggt cttcccgtgg gatgcgggat cctgagaccc aagggtgttt ggtttaaaaa | 1440 |
| gaagactggg cgtccgctct tccaggacgg cctctgtgct gctggggtca cgcgaggctg | 1500 |
| tttgcagggg acacggtcac aggagctctt ctgccctgaa cgctcccaac ctgcctcccg | 1560 |
| cccggaagcc acaggaccca ctcatgtgtg tgcccacaag tgtagttagc cgtccacacc | 1620 |
| gaggagcccc cggaagtccc cactgggctt cagtgtcctc tgccacattc cctgggagga | 1680 |
| acaatgtccc tcggctgttc cggtgaaaag ttgagccacc tttggaagac gcacgggtgg | 1740 |
| agtttgccag aagaaaggct gtgccagggc cgtgtttggc tacaggggct gccggggctc | 1800 |
| ttggctctgc agcgagaaag acacagccca gcagggctgg agacgcccat gtccagcagg | 1860 |
| cgcaggcctg caacacggt ccccagagtc ctgagcagca gttaggtgca tggagagggt | 1920 |
| atcacctggt ggccacagtc ccccttctca cctcagcaat gatcccaaa gtgagaggtg | 1980 |
| gctcccccgg ccccaccac cctcagcagc cccaccccac tcaaccctga gggtccccag | 2040 |
| ggtcctgatg aagacctccg accccagcgc caggctcctc ggagcccaac agtcccaagg | 2100 |

| | |
|---|---|
| gggcaggaga cggggtggtc cagtgctgag gggtacagcc ctgggccctg accagccccg | 2160 |
| gcacctgcca tgctggttcc cggaatgaat cagctgctga ctgtctccag aagggctgga | 2220 |
| aaggatgctg ccaggtgacc cgaggtgcac tcgccccagg gagatggagt agacagcctg | 2280 |
| gcctggccct cgggacacat tgtctgcccc ggggctatgg gcaaatgccc ctccttctta | 2340 |
| cttcccagaa tcccctgaca ttcccagggt cagccaggac ctgttacagc cctggtcact | 2400 |
| tggaactgac agctgtgtga ggcctgcact tctcagaccc agacttagaa caaaaggagg | 2460 |
| agtgaggact caaggctaca atgaggttcc agtacttgtt acaagaaatt ggttttctgc | 2520 |
| aaaaaaagtc cctacctgag cctttaggtg aatgtgggat ccactcccgc ttttaacatg | 2580 |
| aaagcattag aagatgtgtg gtgtttataa aagaacagtt gtcatcaccg ggcattgatt | 2640 |
| ggcagggaca aggagctgct tgggtgtgga agttggggc gttggaaagt gggctgtggt | 2700 |
| gcccatttgc agtgactgtg aagtgactcc aggacggacc tgcggggggca ccagagggtc | 2760 |
| ctaagcccca ggactgaggg tcgtgcatca ccactcgggt gtcccgggag gtgccctggg | 2820 |
| cccggggacc tcacaggcag gacggcgaca ctaatgcagg gagagggagt ctggccccag | 2880 |
| cttttcctat cagaggcgat tttccttcac caggggatgg gcaggaaaga ggcaggggcc | 2940 |
| ccagaagctt ctgtccctca tgcctgaggg cacgggggac acttggaggc tgctgtcacc | 3000 |
| actgtgcgtc caaggccatg ctctctgcgg gtcagtgcct gagtctcgcc tccctgctgg | 3060 |
| tccctgaagc ccctcagaa gccctgcctg tcacgtcggc atttgtgaga cctaccctgt | 3120 |
| aacgcctgcc cctctcagcc caacatcagc ttcctctttc tcccttgctg tagacaggct | 3180 |
| ggattccagt gttgggacag ccatctccag aaacctgact aagagagta agatgcaaa | 3239 |

<210> SEQ ID NO 18
<211> LENGTH: 629
<212> TYPE: DNA
<213> ORGANISM: Homo sapiens

<400> SEQUENCE: 18

| | |
|---|---|
| cgaggtcgaa acgtacgttc tctctatcgt cccgtcaggc cccctcaaag ccgagatcgc | 60 |
| gcagagactt gaagatgtct ttgcagggaa gaacacagat ctcgaggctc tcatggaatg | 120 |
| gctaaagaca agaccaatcc tgtcacctct gactaagggg attttagggt ttgtgttcac | 180 |
| gctcaccgtg cccagtgagc gaggactgca gcgtagacgc tttgtccaaa atgccctaaa | 240 |
| tggaaatgga gacccaaaca acatggacag ggcagtcaaa cttttataaga agctgaaaag | 300 |
| agagataaca ttccatggag ctaaggaggt tgcactcagc tactcaaccg gtgcacttgc | 360 |
| cagttgcatg ggtctcatat acaacaggat ggggacggta accacagaag tggcttttgg | 420 |
| cctagtgtgt gccacttgtg agcagattgc tgattcacag catcgatctc acagacagat | 480 |
| ggtgactaca accaacccac taattaggca tgaaaacagg atggtgctgg ccagcactac | 540 |
| ggctaaggct atggagcaga tggctggatc gagtgagcag gcagcggagg ccatggaggt | 600 |
| tgctagtcag gctaggcaga tggtgcagg | 629 |

<210> SEQ ID NO 19
<211> LENGTH: 1267
<212> TYPE: DNA
<213> ORGANISM: Homo sapiens

<400> SEQUENCE: 19

| | |
|---|---|
| acattctctt ttctttatt cttgtctgtt ctgcctcact cccgagctct actgactccc | 60 |

```
aacagagcgc ccaagaagaa aatggccata agtggagtcc ctgtgctagg attttcatc      120 atagctgtgc tgatgagcgc tcaggaatca tgggctatca agaagaaca tgtgatcatc       180 caggccgagt tctatctgaa tcctgaccaa tcaggcgagt ttatgtttga ctttgatggt      240
gatgagattt ccatgtgga tatggcaaag aaggagacgg tctggcggct tgaagaattt       300
ggacgatttg ccagctttga ggctcaaggt gcattggcca acatagctgt ggacaaagcc      360
aacctggaaa tcatgacaaa gcgctccaac tatactccga tcaccaatgt acctccagag      420
gtaactgtgc tcacgaacag ccctgtggaa ctgagagagc caacgtcct catctgtttc       480 atagacaagt tcaccccacc agtggtcaat gtcacgtggc ttcgaaatgg aaaacctgtc      540
accacaggag tgtcagagac agtcttcctg cccaggaag accaccttt ccgcaagttc        600 cactatctcc ccttcctgcc ctcaactgag gacgtttacg actgcagggt ggagcactgg      660
ggcttggatg agcctcttct caagcactgg gagtttgatg ctccaagccc tctcccagag     720
actacagaga acgtggtgtg tgccctgggc ctgactgtgg gtctggtggg catcattatt      780
gggaccatct tcatcatcaa gggattgcgc aaaagcaatg cagcagaacg caggggccct     840
ctgtaaggca catggaggtg atggtgttc ttagagagaa gatcactgaa gaaacttctg       900
ctttaatggc tttacaaagc tggcaatatt acaatccttg acctcagtga aagcagtcat      960
cttcagcatt ttccagccct atagccaccc caagtgtgga tatgcctctt cgattgctcc      1020
gtactctaac atctagctgg cttccctgtc tattgccttt tcctgtatct atttcctct      1080 atttcctatc attttattat caccatgcaa tgcctctgga ataaaacata caggagtctg      1140
tctctgctat ggaatgcccc atggggcatc tcttgtgtac ttattgttta aggtttcctc     1200
aaactgtgat ttttctgaac acaataaact attttgatga tcttgggtgg aaaaaaaaa     1260 aaaaaaa                                                                1267

<210> SEQ ID NO 20
<211> LENGTH: 1193
<212> TYPE: DNA
<213> ORGANISM: Homo sapiens

<400> SEQUENCE: 20 gggggggccat agttctccct gattgagact tgcctgctgc tgtgaccact ggtcttgtcc      60
tcttctccag catggtgtgt ctgaagctcc ctggaggctc ctgtatggca gcgctgacag      120
tgacattgac ggtgctgagc tccccactgg cttttggctgg gacacccaa ccacgttct       180 tggagcaggc taagtgtgag tgtcatttcc tcaatgggac ggagcgagtg tggaacctga     240
tcagatacat ctataaccaa gaggagtacg cgcgctacaa cagtgacctg ggggagtacc       300
aggcggtgac ggagctgggg cggcctgacg ctgagtactg gaacagccag aaggacctcc      360
tggagcggag gcgggccgag gtggacacct actgcagata caactacggg ttgtgggaga     420
gcttcacagt gcagcggcga gtccaaccta aggtgactgt gtatccttca aagacccagc       480
ccctgcagca ccacaacctc ctggtctgct ctgtgaatgg tttctatcca ggcagcattg     540
aagtcaggtg gttccggaac ggccaggaag agaaggctgg ggtggtgtcc acaggcctga      600
tccagaatgg agactggacc ttccagaccc tggtgatgct ggaaacagtt cctcggagtg     660
gagaggttta cacctgccaa gtggagcatc caagcatgat gagccctctc acggtgcaat      720
ggagtgcacg gtctgaatct gcacagagca agatgctgag tggagtcggg ggctttgtgc     780
tgggcctgct cttccttggg acagggctgt tcatctactt caggaatcag aaaggacact    840
ctggacttca gccaacagga ctcttgagct gaagtgcaga tgaccacatt caaggaagaa    900
```

-continued

```
ccttctgccc cagctttgca agatgaaaag ctttcccact tggctcttat tcttccacaa      960
gagctttgtc aggaccaggt tgttactggt tcagcaactc tgcagaaaat gtcctccctt     1020
gtggcttcct tagctcctgt tcttggcctg aagcctcaca gctttgatgg cagtgcctca     1080
tcttcaactt tgtgcttcc ctttacctaa actgtcctgc ctcccgtgca tctgtactcc      1140
ccttgtgcca cacattgcat tattaaatgt ttctcaaaca tggagttaaa aaa            1193
```

<210> SEQ ID NO 21
<211> LENGTH: 1396
<212> TYPE: DNA
<213> ORGANISM: Homo sapiens

<400> SEQUENCE: 21

```
atgatcccca ccttcacggc tctgctctgc ctcgggctga gtctgggccc caggacccac       60
atgcaggcag ggcccctccc caaacccacc tctgggctg agccaggctc tgtgatcagc       120
tgggggaact ctgtgaccat ctggtgtcag ggaccctgg aggctcggga gtaccgtctg       180
gataaagagg aaagcccagc accctgggac agacagaacc cactggagcc caagaacaag      240
gccagattct ccatcccatc catgacagag gactatgcag ggagataccg ctgttactat      300
cgcagccctg taggctggtc acagcccagt gaccccctgg agctggtgat gacaggagcc      360
tacagtaaac ccacccttc agccctgccg agtcctcttg tgacctcagg aaagagcgtg       420
accctgctgt gtcagtcacg gagcccaatg gacactttcc ttctgatcaa ggagcgggca      480
gcccatcccc tactgcatct gagatcagag cacggagctc agcagcacca ggctgaattc      540 ccatgagtc ctgtgacctc agtgcacggg gggacctaca ggtgcttcag ctcacacggc       600
ttctcccact acctgctgtc acaccccagt gacccctgg agctcatagt ctcaggatcc       660
ttggagggtc ccaggccctc acccacaagg tccgtctcaa cagctgcagg ccctgaggac      720
cagcccctca tgcctacagg gtcagtcccc cacagtggtc tgagaaggca ctgggaggta     780
ctgatcgggg tcttggtggt ctccatcctg cttctctccc tcctcctctt cctcctcctc      840
caacactggc gtcagggaaa acacaggaca ttggcccaga cagagctga tttccaacgt      900 cctccagggg ctgccgagcc agagcccaag gacggggcc tacagaggag gtccagccca      960
gctgctgacg tccagggaga aaacttctgt gctgccgtga agaacacaca gcctgaggac     1020
ggggtggaaa tggacactcg gagcccacac gatgaagacc cccaggcagt gacgtatgcc     1080
aaggtgaaac actccagacc taggagagaa atggcctctc ctccctcccc actgtctggg     1140
gaattcctgg acacaaagga cagacaggca gaagaggaca gacagatgga cactgaggct     1200
gctgcatctg aagcccccca ggatgtgacc tacgcccagc tgcacagctt taccctcaga     1260
cagaaggcaa ctgagcctcc tccatcccag gaagggggcct ctccagctga gcccagtgtc    1320
tatgccactc tggccatcca ctaatccagg ggggacccag accccacaag ccatggagac     1380
tcaggacccc agaagg                                                    1396
```

<210> SEQ ID NO 22
<211> LENGTH: 2221
<212> TYPE: DNA
<213> ORGANISM: Homo sapiens

<400> SEQUENCE: 22

```
gctcactgcc acacgcagct cagcctgggc ggcacagcca gatgcgagat gcgtctctgc       60
tgatctgagt ctgcctgcag catggacctg ggtcttccct gaagcatctc cagggctgga     120
```

```
gggacgactg ccatgcaccg agggctcatc catccgcaga gcagggcagt gggaggagac    180
gccatgaccc ccatcgtcac agtcctgatc tgtctcgggc tgagtctggg ccccaggacc    240
cacgtgcaga cagggaccat ccccaagccc accctgtggg ctgagccaga ctctgtgatc    300
acccagggga gtcccgtcac cctcagttgt caggggagcc ttgaagccca ggagtaccgt    360
ctatataggg agaaaaaatc agcatcttgg attacacgga tacgaccaga gcttgtgaag    420
aacggccagt tccacatccc atccatcacc tgggaacaca cagggcgata tggctgtcag    480
tattacagcc gcgctcggtg gtctgagctc agtgaccccc tggtgctggt gatgacagga    540
gcctacccaa aacccaccct ctcagcccag cccagccctg tggtgacctc aggaggaagg    600
gtgaccctcc agtgtgagtc acaggtggca tttggcggct tcattctgtg taaggaagga    660
gaagatgaac acccacaatg cctgaactcc cagccccatg cccgtgggtc gtcccgcgcc    720
atcttctccg tgggccccgt gagcccgaat cgcaggtggt cgcacaggtg ctatggttat    780
gacttgaact ctccctatgt gtggtcttca cccagtgatc tcctggagct cctggtccca    840
ggtgtttcta agaagccatc actctcagtg cagccgggtc ctgtcgtggc ccctggggaa    900
agcctgaccc tccagtgtgt ctctgatgtc ggctatgaca gatttgttct gtacaaggag    960
ggggaacgtg accttcgcca gctccctggc cggcagcccc aggctgggct ctcccaggcc   1020
aacttcaccc tgggccctgt gagccgctcc tacgggggcc agtacagatg ctacggtgca   1080
tacaacctct cctccgagtg gtcggccccc agcgaccccc tggacatcct gatcacagga   1140
cagatccatg gcacacccct catctcagtg cagccaggcc ccacagtggc ctcaggagag   1200
aacgtgaccc tgctgtgtca gtcatggcgg cagttccaca cttttccttct gaccaaggcg   1260
```